United States Patent
Beutler et al.

(10) Patent No.: US 11,365,250 B2
(45) Date of Patent: Jun. 21, 2022

(54) COMPOSITIONS AND METHODS FOR CANCER THERAPY

(71) Applicant: The Board of Regents of The University of Texas System, Austin, TX (US)

(72) Inventors: Bruce Beutler, Austin, TX (US); Evan Nair-Gill, Austin, TX (US); Xue Zhong, Austin, TX (US); Jinglei Zhang, Austin, TX (US); Pingping Wang, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/767,152

(22) PCT Filed: Nov. 29, 2018

(86) PCT No.: PCT/US2018/063082
§ 371 (c)(1),
(2) Date: May 27, 2020

(87) PCT Pub. No.: WO2019/108806
PCT Pub. Date: Jun. 6, 2019

(65) Prior Publication Data
US 2020/0385459 A1 Dec. 10, 2020

Related U.S. Application Data

(60) Provisional application No. 62/591,874, filed on Nov. 29, 2017.

(51) Int. Cl.
*C07K 16/28* (2006.01)

(52) U.S. Cl.
CPC .......... *C07K 16/28* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2004/0005334 A1 | 1/2004 | Seed et al. | |
| 2007/0105133 A1 | 5/2007 | Clarke et al. | |
| 2010/0210517 A1 | 8/2010 | Starr et al. | |
| 2013/0296302 A1* | 11/2013 | Hood | A61P 19/10 514/210.21 |
| 2015/0268241 A1* | 9/2015 | Egland | G01N 33/57415 514/789 |
| 2017/0319688 A1* | 11/2017 | Storm | C07K 16/2803 |
| 2017/0355756 A1* | 12/2017 | Julien | A61P 21/02 |

FOREIGN PATENT DOCUMENTS

| | | | |
|---|---|---|---|
| WO | WO2008068048 | * | 6/2008 |
| WO | 2017093478 A1 | | 6/2017 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Jeong "The low-density lipoprotein receptor-related protein 10 is a negative regulator of the canonical Wnt/b-catenin signaling pathway" Biochemical and Biophysical Research Communications 392 (2010) 495-499 (Year: 2010).*
Zhan "Wnt signaling in cancer" Oncogene (2017) 36, 1461-1473 (Year: 2017).*
Gonias et al., "Expression of LDL Receptor-Related Proteins (LRPs) In Common Solid Malignancies Correlates With Patient Survival.", PLoS ONE, Oct. 31, 2017, 12(10): e0186649, pp. 1-14; abstract, https://doi.org/10.1371/journal.pone.0186649.
International Search Report in PCT International Publication No. PCT/US2018/063082 dated Mar. 12, 2019.
Written Opinion in related International Application No. PCT/US2018/63082 dated Mar. 12, 2019.
International Preliminary Report on Patentability in related International Application No. PCT/US2018/063082 dated Mar. 12, 2019.
Extended European Search Report in related European Application No. 18882791.9 dated Jul. 30, 2021.
Jeong Y H. et al., "Molecular characterization and expression of the low-density lipoprotein receptor-related protein-10, a new member of the LDLR gene family," Biochemical and Biophysical Research Communications, Elsevier, Amsterdam NL, vol. 391, No. 1, Jan. 1, 2010 (Jan. 1, 2010), pp. 1110-1115, XP026908041, ISSN:0006-291X, DdOI: 10.1016/J.BBRC.2009.12.033.
Julie Brodeur et al., "LDLR-related protein 10 (LRP10) regulates amyloid precursor protein (APP) trafficking and processing: evidence for a role in Alzheimer's disease," Molecular Neurodegeneration, Biomed Central Ltd, LO, vol. 7, No. 1, Jun. 26, 2012 (Jun. 26, 2012), p. 31, XP021116917, ISSN: 1750-1326, DOI: 10.1186/1750-1326-7-31.

* cited by examiner

*Primary Examiner* — Adam Weidner
(74) *Attorney, Agent, or Firm* — Polsinelli PC

(57) ABSTRACT

The present disclosure generally relates to compositions and methods for cancer immunotherapy, as well as hematopoietic recovery following cancer treatment such as chemotherapy or irradiation.

17 Claims, 13 Drawing Sheets
Specification includes a Sequence Listing.

SEQUENCE LISTING

```
<160> NUMBER OF SEQ ID NOS: 74

<210> SEQ ID NO 1
<211> LENGTH: 108
<212> TYPE: PRT
<213> ORGANISM: Unknown
<220> FEATURE:
<223> OTHER INFORMATION: Synthetic

<400> SEQUENCE: 1

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Asn Ala Ser Asp Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Arg Thr Pro
                85                  90                  95

Thr Thr Phe Gly Gln Gly Thr Lys Val Glu Ile Lys
            100                 105

<210> SEQ ID NO 2
<211> LENGTH: 118
<212> TYPE: PRT
<213> ORGANISM: Unknown
<220> FEATURE:
<223> OTHER INFORMATION: Synthetic

<400> SEQUENCE: 2

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Gln Ala Met Ser Trp Val Arg Gln Ala Pro Gly Lys Gly Leu Glu
        35                  40                  45

Trp Val Ser Ser Ile Pro Pro Gly Gly Pro Asn Thr Lys Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Tyr Pro Ser Phe Asp Tyr Trp Gly Gln Gly Thr
            100                 105                 110

Leu Val Thr Val Ser Ser
```

<210> SEQ ID NO 3
<211> LENGTH: 324
<212> TYPE: DNA
<213> ORGANISM: Unknown
<220> FEATURE:
<223> OTHER INFORMATION: Synthetic

<400> SEQUENCE: 3

```
acggacatcc agatgaccca gtctccatcc tccctgtctg catctgtagg agacagagtc    60
accatcactt gccgggcaag tcagagcatt agcagctatt taaattggta tcagcagaaa   120
ccagggaaag cccctaagct cctgatctat aatgcatccg atttgcaaag tggggtccca   180
tcaaggttca gtggcagtgg atctgggaca gatttcactc tcaccatcag cagtctgcaa   240
cctgaagatt ttgcaactta ctactgtcaa cagtcgtcgc ggacgcctac gacgttcggc   300
caagggacca aggtggaaat caaa                                          324
```

<210> SEQ ID NO 4
<211> LENGTH: 354
<212> TYPE: DNA
<213> ORGANISM: Unknown
<220> FEATURE:
<223> OTHER INFORMATION: Synthetic

<400> SEQUENCE: 4

```
atggccgagg tgcagctgtt ggagtctggg ggaggcttgg tacagcctgg ggggtccctg    60
agactctcct gtgcagcctc tggattcacc tttagcagct aggccatgag ctgggtccgc   120
caggctccag ggaaggggct ggagtgggtc tcatctattc ctccgggtgg tcctaataca   180
aagtacgcag actccgtgaa gggccggttc accatctcca gagacaattc caagaacacg   240
ctgtatctgc aaatgaacag cctgagagcc gaggacacgg ccgtatatta ctgtgcgaaa   300
agttatcctt cttttgacta ctggggccag ggaaccctgg tcaccgtctc gagc         354
```

<210> SEQ ID NO 5
<211> LENGTH: 108
<212> TYPE: PRT
<213> ORGANISM: Unknown
<220> FEATURE:
<223> OTHER INFORMATION: Synthetic

<400> SEQUENCE: 5

Thr Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Ser Ile Ser Ser
            20                  25                  30
Tyr Leu Asn Trp Tyr Gln Gln Lys Pro Gly Lys Ala Pro Lys Leu Leu
        35                  40                  45
Ile Tyr Ala Ala Ser Pro Leu Gln Ser Gly Val Pro Ser Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Thr Tyr Tyr Cys Gln Gln Val Ala Arg Thr Pro
                85                  90                  95
Asn Thr Phe Gly Gln Gly Thr Lys Val Glu Ile Lys
            100                 105

<210> SEQ ID NO 6

<211> LENGTH: 324
<212> TYPE: DNA
<213> ORGANISM: Unknown
<220> FEATURE:
<223> OTHER INFORMATION: Synthetic

<400> SEQUENCE: 6

```
acggacatcc agatgaccca gtctccatcc tccctgtctg catctgtagg agacagagtc    60
accatcactt gccgggcaag tcagagcatt agcagctatt taaattggta tcagcagaaa   120
ccagggaaag cccctaagct cctgatctat gcggcatccc gttgcaaag tggggtccca   180
tcaaggttca gtggcagtgg atctgggaca gatttcactc tcaccatcag cagtctgcaa   240
cctgaagatt ttgcaactta ctactgtcaa caggtggctc gtacgcctaa tacgttcggc   300
caagggacca aggtggaaat caaa                                         324
```

<210> SEQ ID NO 7
<211> LENGTH: 108
<212> TYPE: PRT
<213> ORGANISM: Unknown
<220> FEATURE:
<223> OTHER INFORMATION: Synthetic

<400> SEQUENCE: 7

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Pro Thr Ser Leu Pro
                85                  90                  95

Leu Thr Phe Gly Gln Gly Thr Lys Val Glu Ile Lys
            100                 105

<210> SEQ ID NO 8
<211> LENGTH: 118
<212> TYPE: PRT
<213> ORGANISM: Unknown
<220> FEATURE:
<223> OTHER INFORMATION: Synthetic

<400> SEQUENCE: 8

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Gln Ile Gly Thr Met Gly Arg Pro Thr Thr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Gly Lys Lys Phe Asp Tyr Trp Gly Gln Gly Thr
            100                 105                 110

Leu Val Thr Val Ser Ser
        115

<210> SEQ ID NO 9
<211> LENGTH: 324
<212> TYPE: DNA
<213> ORGANISM: Unknown
<220> FEATURE:
<223> OTHER INFORMATION: Synthetic

<400> SEQUENCE: 9
acggacatcc agatgaccca gtctccatcc tccctgtctg catctgtagg agacagagtc    60
accatcactt gccgggcaag tcagagcatt agcagctatt taaattggta tcagcagaaa   120
ccagggaaag cccctaagct cctgatctat agggcatccc gtttgcaaag tggggtccca   180
tcaaggttca gtggcagtgg atctgggaca gatttcactc tcaccatcag cagtctgcaa   240
cctgaagatt ttgcaactta ctactgtcaa cagccgactt cgttgcctct gacgttcggc   300
caagggacca aggtggaaat caaa                                          324

<210> SEQ ID NO 10
<211> LENGTH: 354
<212> TYPE: DNA
<213> ORGANISM: Unknown
<220> FEATURE:
<223> OTHER INFORMATION: Synthetic

<400> SEQUENCE: 10
atggccgagg tgcagctgtt ggagtctggg ggaggcttgg tacagcctgg ggggtccctg    60
agactctcct gtgcagcctc tggattcacc tttagcagct atgccatgag ctgggtccgc   120
caggctccag ggaaggggct ggagtgggtc tcatagattg gacgatggg tcggccgaca   180 acttacgcag actccgtgaa gggccggttc accatctcca gagacaattc caagaacacg   240
ctgtatctgc aaatgaacag cctgagagcc gaggacacgg ccgtatatta ctgtgcgaaa   300
agtgggaaga gtttgactac tgggggccag ggaaccctgg tcaccgtctc gagc         354

<210> SEQ ID NO 11
<211> LENGTH: 108
<212> TYPE: PRT
<213> ORGANISM: Unknown
<220> FEATURE:
<223> OTHER INFORMATION: Synthetic

<400> SEQUENCE: 11

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ala Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Asp Ser Tyr Pro
                85                  90                  95

Thr Thr Phe Gly Gln Gly Thr Lys Val Glu Ile Lys

<210> SEQ ID NO 12
<211> LENGTH: 118
<212> TYPE: PRT
<213> ORGANISM: Unknown
<220> FEATURE:
<223> OTHER INFORMATION: Synthetic

<400> SEQUENCE: 12

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Leu Ala Pro Gly Lys Gly Leu Glu
        35                  40                  45

Trp Val Ser Ser Ile Ser Thr Thr Gly Asn Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ala Thr Ser Phe Asp Tyr Trp Gly Gln Gly Thr
            100                 105                 110

Leu Val Thr Val Ser Ser
        115

<210> SEQ ID NO 13
<211> LENGTH: 324
<212> TYPE: DNA
<213> ORGANISM: Unknown
<220> FEATURE:
<223> OTHER INFORMATION: Synthetic

<400> SEQUENCE: 13
acggacatcc agatgaccca gtctccatcc tccctgtctg catctgtagg agacagagtc     60
accatcactt gccgggcaag tcagagcatt agcagctatt taaattggta tcagcagaaa    120
ccagggaaag cccctaagct cctgatctat gctgcatccg cttttgcaaag tggggtccca   180 tcaaggttca gtggcagtgg atctgggaca gatttcactc tcaccatcag cagtctgcaa    240
cctgaagatt ttgcaactta ctactgtcaa caggctgatt cttatcctac tacgttcggc    300
caagggacca aggtggaaat caaa                                           324

<210> SEQ ID NO 14
<211> LENGTH: 354
<212> TYPE: DNA
<213> ORGANISM: Unknown
<220> FEATURE:
<223> OTHER INFORMATION: Synthetic

<400> SEQUENCE: 14
atggccgagg tgcagctgtt ggagtctggg ggaggcttgg tacagcctgg ggggtccctg     60
agactctcct gtgcagcctc tggattcacc tttagcagct atgccatgag ctgggtccgc    120
ctggctccag ggaaggggct ggagtgggtc tcatctattt ctactactgg taatagtaca    180
tattacgcag actccgtgaa gggccggttc accatctcca gagacaattc caagaacacg    240
ctgtatctgc aaatgaacag cctgagagcc gaggacacgg ccgtatatta ctgtgcgaaa    300
gatgctacta gttttgacta ctggggccag ggaaccctgg tcaccgtctc gagc          354

<210> SEQ ID NO 15
<211> LENGTH: 108
<212> TYPE: PRT
<213> ORGANISM: UNKNOWN
<220> FEATURE:
<223> OTHER INFORMATION: SYNTHETIC

<400> SEQUENCE: 15

```
Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Arg Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ile Lys Thr Arg Pro
                85                  90                  95

Thr Thr Phe Gly Gln Gly Thr Lys Val Glu Ile Lys
            100                 105
```

<210> SEQ ID NO 16
<211> LENGTH: 118
<212> TYPE: PRT
<213> ORGANISM: UNKNOWN
<220> FEATURE:
<223> OTHER INFORMATION: SYNTHETIC

<400> SEQUENCE: 16

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Gln Arg Gln Gly Thr Gly Thr Glu Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Ser Arg Thr Phe Asp Tyr Trp Gly Gln Gly Thr
            100                 105                 110

Leu Val Thr Val Ser Ser
        115
```

<210> SEQ ID NO 17
<211> LENGTH: 324
<212> TYPE: DNA
<213> ORGANISM: UNKNOWN
<220> FEATURE:
<223> OTHER INFORMATION: SYNTHETIC

<400> SEQUENCE: 17

```
acggacatcc agatgaccca gtctccatcc tccctgtctg catctgtagg agacagagtc    60
accatcactt gccgggcaag tcagagcatt agcagctatt taaattggta tcagcagaaa   120
```

```
ccagggaaag cccctaagct cctgatctat cgtgcatccc gtttgcaaag tggggtccca    180
tcaaggttca gtggcagtgg atctgggaca gatttcactc tcaccatcag cagtctgcaa    240
cctgaagatt ttgcaactta ctactgtcaa cagattaaga caaggcctac gacgttcggc    300
caagggacca aggtggaaat caaa                                            324
```

```
<210> SEQ ID NO 18
<211> LENGTH: 354
<212> TYPE: DNA
<213> ORGANISM: UNKNOWN
<220> FEATURE:
<223> OTHER INFORMATION: SYNTHETIC

<400> SEQUENCE: 18
atggccgagg tgcagctgtt ggagtctggg ggaggcttgg tacagcctgg ggggtccctg     60
agactctcct gtgcagcctc tggattcacc tttagcagct atgccatgag ctgggtccgc    120
caggctccag ggaaggggct ggagtgggtc tcagttattc agcgttaggg tactggtaca    180
gagtacgcag actccgtgaa gggccggttc accatctcca gagacaattc caagaacacg    240
ctgtatctgc aaatgaacag cctgagagcc gaggacacgg ccgtatatta ctgtgcaaaa    300
aattcgcgga cgtttgacta ctggggccag ggaaccctgg tcaccgtctc gagc          354
```

```
<210> SEQ ID NO 19
<211> LENGTH: 108
<212> TYPE: PRT
<213> ORGANISM: UNKNOWN
<220> FEATURE:
<223> OTHER INFORMATION: SYNTHETIC

<400> SEQUENCE: 19

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Asp Ala Ser Leu Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Ser Ala Gly Pro
                85                  90                  95

Gly Thr Phe Gly Gln Gly Thr Lys Val Glu Ile Lys
            100                 105
```

```
<210> SEQ ID NO 20
<211> LENGTH: 118
<212> TYPE: PRT
<213> ORGANISM: UNKNOWN
<220> FEATURE:
<223> OTHER INFORMATION: SYNTHETIC

<400> SEQUENCE: 20

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
```

```
                    35                  40                  45

Trp Val Ser Ser Ile Pro Ser Arg Gly Gln Ala Thr Lys Tyr Ala Asp
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Ser Arg His Thr Phe Asp Tyr Trp Gly Gln Gly Thr
            100                 105                 110

Leu Val Thr Val Ser Ser
            115

<210> SEQ ID NO 21
<211> LENGTH: 324
<212> TYPE: DNA
<213> ORGANISM: UNKNOWN
<220> FEATURE:
<223> OTHER INFORMATION: SYNTHETIC

<400> SEQUENCE: 21
acggacatcc agatgaccca gtctccatcc tccctgtctg catctgtagg agacagagtc     60
accatcactt gccgggcaag tcagagcatt agcagctatt taaattggta tcagcagaaa    120
ccagggaaag cccctaagct cctgatctat gatgcatccc ttttgcaaag tggggtccca    180
tcaaggttca gtggcagtgg atctgggaca gatttcactc tcaccatcag cagtctgcaa    240
cctgaagatt ttgcaactta ctactgtcaa cagacttctg cgggtcctgg tacgttcggc    300
caagggacca aggtggaaat caaa                                           324

<210> SEQ ID NO 22
<211> LENGTH: 354
<212> TYPE: DNA
<213> ORGANISM: UNKNOWN
<220> FEATURE:
<223> OTHER INFORMATION: SYNTHETIC

<400> SEQUENCE: 22
atggccgagg tgcagctgtt ggagtctggg ggaggcttgg tacagcctgg ggggtccctg     60
agactctcct gtgcagcctc tggattcacc tttagcagct atgccatgag ctgggtccgc    120
caggctccag gaaggggct ggagtgggtc tcaagtattc ctagtcgtgg ttaggcaaca    180
aagtacgcag actccgtgaa gggccggttc accatctcca gagacaattc caagaacacg    240
ctgtatctgc aaatgaacag cctgagagcc gaggacacgg ccgtatatta ctgcgcgaaa    300
tcgcgtcata cttttgacta ctggggccag ggaaccctgg tcaccgtctc gagc          354

<210> SEQ ID NO 23
<211> LENGTH: 108
<212> TYPE: PRT
<213> ORGANISM: UNKNOWN
<220> FEATURE:
<223> OTHER INFORMATION: SYNTHETIC

<400> SEQUENCE: 23

Thr Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser Ser
             20                  25                  30

Tyr Leu Asn Trp Tyr Gln Gln Lys Pro Gly Lys Ala Pro Lys Leu Leu
         35                  40                  45
```

Ile Tyr Ala Ala Ser Thr Leu Gln Ser Gly Val Pro Ser Arg Phe Ser
            50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Asn Asp Tyr Tyr Pro
                85                  90                  95

Thr Thr Phe Gly Gln Gly Thr Lys Val Glu Ile Lys
            100                 105

<210> SEQ ID NO 24
<211> LENGTH: 118
<212> TYPE: PRT
<213> ORGANISM: UNKNOWN
<220> FEATURE:
<223> OTHER INFORMATION: SYNTHETIC

<400> SEQUENCE: 24

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Ala Thr Thr Gly Asn Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Thr Ala Thr Phe Asp Tyr Trp Gly Gln Gly Thr
            100                 105                 110

Leu Val Thr Val Ser Ser
        115

<210> SEQ ID NO 25
<211> LENGTH: 324
<212> TYPE: DNA
<213> ORGANISM: UNKNOWN
<220> FEATURE:
<223> OTHER INFORMATION: SYNTHETIC

<400> SEQUENCE: 25
acggacatcc agatgaccca gtctccatcc tccctgtctg catctgtagg agacagagtc    60
accatcactt gccgggcaag tcagagcatt agcagctatt taaattggta tcagcagaaa   120
ccagggaaag cccctaagct cctgatctat gctgcatcca ctttgcaaag tggggtccca   180
tcaaggttca gtggcagtgg atctgggaca gatttcactc tcaccatcag cagtctgcaa   240
cctgaagatt ttgcaactta ctactgtcaa cagaatgatt attatcctac tacgttcggc   300
caagggacca aggtggaaat caaa                                           324

<210> SEQ ID NO 26
<211> LENGTH: 354
<212> TYPE: DNA
<213> ORGANISM: UNKNOWN
<220> FEATURE:
<223> OTHER INFORMATION: SYNTHETIC

<400> SEQUENCE: 26

```
atggccgagg tgcagctgtt ggagtctggg ggaggcttgg tacagcctgg ggggtccctg     60
agactctcct gtgcagcctc tggattcacc tttagcagct atgccatgag ctgggtccgc    120
caggctccag ggaaggggct ggagtgggtc tcatctattg ctactactgg taatactaca    180
tattacgcag actccgtgaa gggccggttc accatctcca gagacaattc caagaacacg    240
ctgtatctgc aaatgaacag cctgagagcc gaggacacgg ccgtatatta ctgtgcgaaa    300
aatactgcta cttttgacta ctggggccag ggaaccctgg tcaccgtctc gagc          354
```

```
<210> SEQ ID NO 27
<211> LENGTH: 118
<212> TYPE: PRT
<213> ORGANISM: UNKNOWN
<220> FEATURE:
<223> OTHER INFORMATION: SYNTHETIC

<400> SEQUENCE: 27

Met Ala Glu Val Gln Leu Leu Glu Ser Gly Gly Gly Leu Val Gln Leu
1               5                   10                  15

Gly Gly Ser Leu Arg Leu Ser Cys Ala Ala Ser Gly Phe Thr Phe Ser
            20                  25                  30

Ser Gln Ala Met Ser Trp Val Arg Gln Ala Pro Gly Lys Gly Leu Glu
        35                  40                  45

Trp Val Ser Ser Ile Pro Pro Gly Gly Pro Asn Thr Lys Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Tyr Pro Ser Phe Asp Tyr Trp Gly Gln Gly Thr
            100                 105                 110

Leu Val Thr Val Ser Ser
        115
```

```
<210> SEQ ID NO 28
<211> LENGTH: 354
<212> TYPE: DNA
<213> ORGANISM: UNKNOWN
<220> FEATURE:
<223> OTHER INFORMATION: SYNTHETIC

<400> SEQUENCE: 28
atggccgagg tgcagctgtt ggagtctggg ggaggcttgg tacagcttgg ggggtccctg     60
agactctcct gtgcagcctc tggattcacc tttagcagct aggccatgag ctgggtccgc    120
caggctccag ggaaggggct ggagtgggtc tcatctattc ctccgggtgg tcctaataca    180
aagtacgcag actccgtgaa gggccggttc accatctcca gagacaattc caagaacacg    240
ctgtatctgc aaatgaacag cctgagagcc gaggacacgg ccgtatatta ctgtgcgaaa    300
agttatcctt cttttgacta ctggggccag ggaaccctgg tcaccgtctc gagc          354
```

```
<210> SEQ ID NO 29
<211> LENGTH: 118
<212> TYPE: PRT
<213> ORGANISM: UNKNOWN
<220> FEATURE:
<223> OTHER INFORMATION: SYNTHETIC

<400> SEQUENCE: 29

Met Ala Glu Val Gln Leu Leu Glu Ser Gly Gly Gly Leu Val Gln Pro
```

```
              1               5                  10                 15
            Gly Gly Ser Leu Arg Leu Ser Cys Ala Ala Ser Gly Phe Thr Phe Ser
                            20                  25                 30

Ser Tyr Ala Met Ser Trp Val Arg Gln Ala Pro Gly Lys Gly Leu Glu
                            35                  40                 45

Trp Val Ser Ser Ile Tyr Thr Ser Gly Ala Ala Thr Thr Tyr Ala Asp
                    50                  55                  60

Ser Val Lys Gly Arg Phe Thr Ile Ser Arg Asp Asn Ser Lys Asn Thr
            65                  70                  75                 80

Leu Tyr Leu Gln Met Asn Ser Leu Arg Ala Glu Asp Thr Ala Val Tyr
                            85                  90                 95

Tyr Cys Ala Lys Ser Tyr Pro Ser Phe Asp Tyr Trp Gly Gln Gly Thr
                            100                 105                110

Leu Val Thr Val Ser Ser
                    115

<210> SEQ ID NO 30
<211> LENGTH: 354
<212> TYPE: DNA
<213> ORGANISM: Unknown
<220> FEATURE:
<223> OTHER INFORMATION: Synthetic

<400> SEQUENCE: 30
atggccgagg tgcagctgtt ggagtctggg ggaggcttgg tacagcctgg ggggtccctg      60
agactctcct gtgcagcctc tggattcacc tttagcagct atgccatgag ctgggtccgc     120
caggctccag ggaaggggct ggagtgggtc tcatctattt atacttctgg tgctgctaca     180
acttacgcag actccgtgaa gggccggttc accatctcca gagacaattc caagaacacg     240
ctgtatctgc aaatgaacag cctgagagcc gaggacacgg ccgtatatta ctgtgcgaaa     300
agttatcctt cttttgacta ctggggccag ggaaccctgg tcaccgtctc gagc          354

<210> SEQ ID NO 31
<211> LENGTH: 107
<212> TYPE: PRT
<213> ORGANISM: Homo sapiens

<400> SEQUENCE: 31

Arg Thr Val Ala Ala Pro Ser Val Phe Ile Phe Pro Pro Ser Asp Glu
            1               5                   10                 15

Gln Leu Lys Ser Gly Thr Ala Ser Val Val Cys Leu Leu Asn Asn Phe
                            20                  25                 30

Tyr Pro Arg Glu Ala Lys Val Gln Trp Lys Val Asp Asn Ala Leu Gln
                            35                  40                 45

Ser Gly Asn Ser Gln Glu Ser Val Thr Glu Gln Asp Ser Lys Asp Ser
                    50                  55                  60

Thr Tyr Ser Leu Ser Ser Thr Leu Thr Leu Ser Lys Ala Asp Tyr Glu
            65                  70                  75                 80

Lys His Lys Val Tyr Ala Cys Glu Val Thr His Gln Gly Leu Ser Ser
                            85                  90                 95

Pro Val Thr Lys Ser Phe Asn Arg Gly Glu Cys
                            100                 105

<210> SEQ ID NO 32
<211> LENGTH: 330
<212> TYPE: PRT
<213> ORGANISM: Homo sapiens
```

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 11
<212> TYPE: PRT
<213> ORGANISM: Unknown
<220> FEATURE:
<223> OTHER INFORMATION: Synthetic

<400> SEQUENCE: 33

Arg Ala Ser Gln Ser Ile Ser Ser Tyr Leu Asn
1               5                   10

<210> SEQ ID NO 34
<211> LENGTH: 7
<212> TYPE: PRT
<213> ORGANISM: Unknown
<220> FEATURE:
<223> OTHER INFORMATION: Synthetic

<400> SEQUENCE: 34

Asn Ala Ser Asp Leu Gln Ser
1               5

<210> SEQ ID NO 35
<211> LENGTH: 7
<212> TYPE: PRT
<213> ORGANISM: Unknown
<220> FEATURE:
<223> OTHER INFORMATION: Synthetic

<400> SEQUENCE: 35

Ala Ala Ser Pro Leu Gln Ser
1               5

<210> SEQ ID NO 36
<211> LENGTH: 7
<212> TYPE: PRT
<213> ORGANISM: Unknown
<220> FEATURE:
<223> OTHER INFORMATION: Synthetic

<400> SEQUENCE: 36

Arg Ala Ser Arg Leu Gln Ser
1               5

<210> SEQ ID NO 37
<211> LENGTH: 7
<212> TYPE: PRT
<213> ORGANISM: Unknown
<220> FEATURE:
<223> OTHER INFORMATION: Synthetic

<400> SEQUENCE: 37

Ala Ala Ser Ala Leu Gln Ser
1               5

<210> SEQ ID NO 38
<211> LENGTH: 7
<212> TYPE: PRT
<213> ORGANISM: Unknown
<220> FEATURE:
<223> OTHER INFORMATION: Synthetic

<400> SEQUENCE: 38

Asp Ala Ser Leu Leu Gln Ser
1               5

<210> SEQ ID NO 39
<211> LENGTH: 7
<212> TYPE: PRT
<213> ORGANISM: Unknown
<220> FEATURE:
<223> OTHER INFORMATION: Synthetic

<400> SEQUENCE: 39

Ala Ala Ser Thr Leu Gln Ser
1               5

```
<210> SEQ ID NO 40
<211> LENGTH: 9
<212> TYPE: PRT
<213> ORGANISM: Unknown
<220> FEATURE:
<223> OTHER INFORMATION: Synthetic

<400> SEQUENCE: 40

Gln Gln Ser Ser Arg Thr Pro Thr Thr
1               5

<210> SEQ ID NO 41
<211> LENGTH: 9
<212> TYPE: PRT
<213> ORGANISM: Unknown
<220> FEATURE:
<223> OTHER INFORMATION: Synthetic

<400> SEQUENCE: 41

Gln Gln Val Ala Arg Thr Pro Asn Thr
1               5

<210> SEQ ID NO 42
<211> LENGTH: 9
<212> TYPE: PRT
<213> ORGANISM: Unknown
<220> FEATURE:
<223> OTHER INFORMATION: Synthetic

<400> SEQUENCE: 42

Gln Gln Pro Thr Ser Leu Pro Leu Thr
1               5

<210> SEQ ID NO 43
<211> LENGTH: 9
<212> TYPE: PRT
<213> ORGANISM: unknown
<220> FEATURE:
<223> OTHER INFORMATION: synthetic

<400> SEQUENCE: 43

Gln Gln Ala Asp Ser Tyr Pro Thr Thr
1               5

<210> SEQ ID NO 44
<211> LENGTH: 9
<212> TYPE: PRT
<213> ORGANISM: Unknown
<220> FEATURE:
<223> OTHER INFORMATION: synthetic

<400> SEQUENCE: 44

Gln Gln Ile Lys Thr Arg Pro Thr Thr
1               5

<210> SEQ ID NO 45
<211> LENGTH: 9
<212> TYPE: PRT
<213> ORGANISM: unknown
<220> FEATURE:
<223> OTHER INFORMATION: synthetic

<400> SEQUENCE: 45

Gln Gln Thr Ser Ala Gly Pro Gly Thr
1               5

<210> SEQ ID NO 46
```

```
<211> LENGTH: 9
<212> TYPE: PRT
<213> ORGANISM: unknown
<220> FEATURE:
<223> OTHER INFORMATION: synthetic

<400> SEQUENCE: 46

Gln Gln Asn Asp Tyr Tyr Pro Thr Thr
1               5

<210> SEQ ID NO 47
<211> LENGTH: 5
<212> TYPE: PRT
<213> ORGANISM: Unknown
<220> FEATURE:
<223> OTHER INFORMATION: synthetic

<400> SEQUENCE: 47

Ser Gln Ala Met Ser
1               5

<210> SEQ ID NO 48
<211> LENGTH: 5
<212> TYPE: PRT
<213> ORGANISM: unknown
<220> FEATURE:
<223> OTHER INFORMATION: synthetic

<400> SEQUENCE: 48

Ser Tyr Ala Met Ser
1               5

<210> SEQ ID NO 49
<211> LENGTH: 17
<212> TYPE: PRT
<213> ORGANISM: unknown
<220> FEATURE:
<223> OTHER INFORMATION: synthetic

<400> SEQUENCE: 49

Gln Ile Gly Thr Met Gly Arg Pro Thr Thr Tyr Ala Asp Ser Val Lys
1               5                   10                  15

Gly

<210> SEQ ID NO 50
<211> LENGTH: 17
<212> TYPE: PRT
<213> ORGANISM: unknown
<220> FEATURE:
<223> OTHER INFORMATION: synthetic

<400> SEQUENCE: 50

Ser Ile Ser Thr Thr Gly Asn Ser Thr Tyr Tyr Ala Asp Ser Val Lys
1               5                   10                  15

Gly

<210> SEQ ID NO 51
<211> LENGTH: 17
<212> TYPE: PRT
<213> ORGANISM: unknown
<220> FEATURE:
<223> OTHER INFORMATION: synthetic

<400> SEQUENCE: 51

Val Ile Gln Arg Gln Gly Thr Gly Thr Glu Tyr Ala Asp Ser Val Lys
1               5                   10                  15
```

Gly

<210> SEQ ID NO 52
<211> LENGTH: 17
<212> TYPE: PRT
<213> ORGANISM: UNKNOWN
<220> FEATURE:
<223> OTHER INFORMATION: SYNTHETIC

<400> SEQUENCE: 52

Ser Ile Pro Ser Arg Gly Gln Ala Thr Lys Tyr Ala Asp Ser Val Lys
1               5                   10                  15

Gly

<210> SEQ ID NO 53
<211> LENGTH: 17
<212> TYPE: PRT
<213> ORGANISM: UNKNOWN
<220> FEATURE:
<223> OTHER INFORMATION: SYNTHETIC

<400> SEQUENCE: 53

Ser Ile Ala Thr Thr Gly Asn Thr Thr Tyr Tyr Ala Asp Ser Val Lys
1               5                   10                  15

Gly

<210> SEQ ID NO 54
<211> LENGTH: 17
<212> TYPE: PRT
<213> ORGANISM: UNKNOWN
<220> FEATURE:
<223> OTHER INFORMATION: SYNTHETIC

<400> SEQUENCE: 54

Ser Ile Pro Pro Gly Gly Pro Asn Thr Lys Tyr Ala Asp Ser Val Lys
1               5                   10                  15

Gly

<210> SEQ ID NO 55
<211> LENGTH: 17
<212> TYPE: PRT
<213> ORGANISM: UNKNOWN
<220> FEATURE:
<223> OTHER INFORMATION: SYNTHETIC

<400> SEQUENCE: 55

Ser Ile Tyr Thr Ser Gly Ala Ala Thr Thr Tyr Ala Asp Ser Val Lys
1               5                   10                  15

Gly

<210> SEQ ID NO 56
<211> LENGTH: 7
<212> TYPE: PRT
<213> ORGANISM: UNKNOWN
<220> FEATURE:
<223> OTHER INFORMATION: SYNTHETIC

<400> SEQUENCE: 56

Ser Tyr Pro Ser Phe Asp Tyr
1               5

<210> SEQ ID NO 57
<211> LENGTH: 7

```
<212> TYPE: PRT
<213> ORGANISM: UNKNOWN
<220> FEATURE:
<223> OTHER INFORMATION: SYNTHETIC

<400> SEQUENCE: 57

Ser Gly Lys Lys Phe Asp Tyr
1               5

<210> SEQ ID NO 58
<211> LENGTH: 7
<212> TYPE: PRT
<213> ORGANISM: UNKNOWN
<220> FEATURE:
<223> OTHER INFORMATION: SYNTHETIC

<400> SEQUENCE: 58

Asp Ala Thr Ser Phe Asp Tyr
1               5

<210> SEQ ID NO 59
<211> LENGTH: 7
<212> TYPE: PRT
<213> ORGANISM: UNKNOWN
<220> FEATURE:
<223> OTHER INFORMATION: SYNTHETIC

<400> SEQUENCE: 59

Asn Ser Arg Thr Phe Asp Tyr
1               5

<210> SEQ ID NO 60
<211> LENGTH: 7
<212> TYPE: PRT
<213> ORGANISM: UNKNOWN
<220> FEATURE:
<223> OTHER INFORMATION: SYNTHETIC

<400> SEQUENCE: 60

Ser Arg His Thr Phe Asp Tyr
1               5

<210> SEQ ID NO 61
<211> LENGTH: 7
<212> TYPE: PRT
<213> ORGANISM: UNKNOWN
<220> FEATURE:
<223> OTHER INFORMATION: SYNTHETIC

<400> SEQUENCE: 61

Asn Thr Ala Thr Phe Asp Tyr
1               5

<210> SEQ ID NO 62
<211> LENGTH: 7
<212> TYPE: PRT
<213> ORGANISM: UNKNOWN
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: X=N, A, R, D
<220> FEATURE:
<221> NAME/KEY: MISC_FEATURE
<222> LOCATION: (4)..(4)
<223> OTHER INFORMATION: X=D, P, R, A, L, T

<400> SEQUENCE: 62
```

```
Xaa Ala Ser Xaa Leu Gln Ser
1               5

<210> SEQ ID NO 63
<211> LENGTH: 9
<212> TYPE: PRT
<213> ORGANISM: UNKNOWN
<220> FEATURE:
<223> OTHER INFORMATION: SYNTHETIC
<220> FEATURE:
<221> NAME/KEY: MISC_FEATURE
<222> LOCATION: (3)..(3)
<223> OTHER INFORMATION: X=S, V, P, A, I, T, N
<220> FEATURE:
<221> NAME/KEY: MISC_FEATURE
<222> LOCATION: (4)..(4)
<223> OTHER INFORMATION: X=S, A, T, D, K
<220> FEATURE:
<221> NAME/KEY: MISC_FEATURE
<222> LOCATION: (5)..(5)
<223> OTHER INFORMATION: X=R, S, T, A, Y
<220> FEATURE:
<221> NAME/KEY: MISC_FEATURE
<222> LOCATION: (6)..(6)
<223> OTHER INFORMATION: X=T, L, Y, R, G
<220> FEATURE:
<221> NAME/KEY: MISC_FEATURE
<222> LOCATION: (8)..(8)
<223> OTHER INFORMATION: X=T, N, L, G

<400> SEQUENCE: 63

Gln Gln Xaa Xaa Xaa Xaa Pro Xaa Thr
1               5

<210> SEQ ID NO 64
<211> LENGTH: 5
<212> TYPE: PRT
<213> ORGANISM: UNKNOWN
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: X=Q, Y

<400> SEQUENCE: 64

Ser Xaa Ala Met Ser
1               5

<210> SEQ ID NO 65
<211> LENGTH: 17
<212> TYPE: PRT
<213> ORGANISM: UNKNOWN
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: X=S, Q, V
<220> FEATURE:
<221> NAME/KEY: MISC_FEATURE
<222> LOCATION: (3)..(3)
<223> OTHER INFORMATION: X=P, G, S, Q, A, Y
<220> FEATURE:
<221> NAME/KEY: MISC_FEATURE
<222> LOCATION: (4)..(4)
<223> OTHER INFORMATION: X=P, T, R, S
<220> FEATURE:
<221> NAME/KEY: MISC_FEATURE
<222> LOCATION: (5)..(5)
<223> OTHER INFORMATION: X=G, M, T, Q, R, S
<220> FEATURE:
<221> NAME/KEY: MISC_FEATURE
```

```
<222> LOCATION: (7)..(7)
<223> OTHER INFORMATION: X=P, R, N, T, Q, A
<220> FEATURE:
<221> NAME/KEY: MISC_FEATURE
<222> LOCATION: (8)..(8)
<223> OTHER INFORMATION: X=N, P, S, G, A, T
<220> FEATURE:
<221> NAME/KEY: MISC_FEATURE
<222> LOCATION: (10)..(10)
<223> OTHER INFORMATION: X=K, T, Y, E

<400> SEQUENCE: 65

Xaa Ile Xaa Xaa Xaa Gly Xaa Xaa Thr Xaa Tyr Ala Asp Ser Val Lys
 1               5                  10                  15

Gly

<210> SEQ ID NO 66
<211> LENGTH: 7
<212> TYPE: PRT
<213> ORGANISM: UNKNOWN
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: X=S, D, N
<220> FEATURE:
<221> NAME/KEY: MISC_FEATURE
<222> LOCATION: (2)..(2)
<223> OTHER INFORMATION: X=Y, G, A, S, R, T
<220> FEATURE:
<221> NAME/KEY: MISC_FEATURE
<222> LOCATION: (3)..(3)
<223> OTHER INFORMATION: X=P, K, T, R, H, A
<220> FEATURE:
<221> NAME/KEY: MISC_FEATURE
<222> LOCATION: (4)..(4)
<223> OTHER INFORMATION: X=S, K, T

<400> SEQUENCE: 66

Xaa Xaa Xaa Xaa Phe Asp Tyr
 1               5

<210> SEQ ID NO 67
<211> LENGTH: 232
<212> TYPE: PRT
<213> ORGANISM: Homo sapiens

<400> SEQUENCE: 67

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

```
Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 68
<211> LENGTH: 326
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 69
<211> LENGTH: 228
<212> TYPE: PRT
<213> ORGANISM: Homo sapiens

<400> SEQUENCE: 69

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 70
<211> LENGTH: 228
<212> TYPE: PRT
<213> ORGANISM: Homo sapiens

<400> SEQUENCE: 70

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

```
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val Val His Gln Asp Trp Leu Asn
                85                  90                  95
Gly Lys Glu Tyr Lys Cys Lys Val Ser Asn Lys Gly Leu Pro Ser Ser
            100                 105                 110
Ile Glu Lys Thr Ile Ser Lys Thr Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys
225

<210> SEQ ID NO 71
<211> LENGTH: 20
<212> TYPE: DNA
<213> ORGANISM: unknown
<220> FEATURE:
<223> OTHER INFORMATION: synthetic

<400> SEQUENCE: 71
agtcccccag gaagaggcaa                                                     20

<210> SEQ ID NO 72
<211> LENGTH: 25
<212> TYPE: DNA
<213> ORGANISM: unknown
<220> FEATURE:
<223> OTHER INFORMATION: synthetic

<400> SEQUENCE: 72
tcacctaggt tctcactagc cccgt                                               25

<210> SEQ ID NO 73
<211> LENGTH: 30
<212> TYPE: DNA
<213> ORGANISM: unknown
<220> FEATURE:
<223> OTHER INFORMATION: synthetic

<400> SEQUENCE: 73
cctggacttg agttacggag atgcagtgca                                          30

<210> SEQ ID NO 74
<211> LENGTH: 440
```

<212> TYPE: PRT
<213> ORGANISM: Homo sapiens

<400> SEQUENCE: 74

```
Met Leu Leu Ala Thr Leu Leu Leu Leu Leu Gly Gly Ala Leu Ala
1               5                   10                  15

His Pro Asp Arg Ile Ile Phe Pro Asn His Ala Cys Glu Asp Pro Pro
            20                  25                  30

Ala Val Leu Leu Glu Val Gln Gly Thr Leu Gln Arg Pro Leu Val Arg
        35                  40                  45

Asp Ser Arg Thr Ser Pro Ala Asn Cys Thr Trp Leu Ile Leu Gly Ser
    50                  55                  60

Lys Glu Gln Thr Val Thr Ile Arg Phe Gln Lys Leu His Leu Ala Cys
65                  70                  75                  80

Gly Ser Glu Arg Leu Thr Leu Arg Ser Pro Leu Gln Pro Leu Ile Ser
                85                  90                  95

Leu Cys Glu Ala Pro Pro Ser Pro Leu Gln Leu Pro Gly Gly Asn Val
            100                 105                 110

Thr Ile Thr Tyr Ser Tyr Ala Gly Ala Arg Ala Pro Met Gly Gln Gly
        115                 120                 125

Phe Leu Leu Ser Tyr Ser Gln Asp Trp Leu Met Cys Leu Gln Glu Glu
130                 135                 140

Phe Gln Cys Leu Asn His Arg Cys Val Ser Ala Val Gln Arg Cys Asp
145                 150                 155                 160

Gly Val Asp Ala Cys Gly Asp Gly Ser Asp Glu Ala Gly Cys Ser Ser
                165                 170                 175

Asp Pro Phe Pro Gly Leu Thr Pro Arg Pro Val Pro Ser Leu Pro Cys
            180                 185                 190

Asn Val Thr Leu Glu Asp Phe Tyr Gly Val Phe Ser Ser Pro Gly Tyr
        195                 200                 205

Thr His Leu Ala Ser Val Ser His Pro Gln Ser Cys His Trp Leu Leu
    210                 215                 220

Asp Pro His Asp Gly Arg Arg Leu Ala Val Arg Phe Thr Ala Leu Asp
225                 230                 235                 240

Leu Gly Phe Gly Asp Ala Val His Val Tyr Asp Gly Pro Gly Pro Pro
                245                 250                 255

Glu Ser Ser Arg Leu Leu Arg Ser Leu Thr His Phe Ser Asn Gly Lys
            260                 265                 270

Ala Val Thr Val Glu Thr Leu Ser Gly Gln Ala Val Val Ser Tyr His
        275                 280                 285

Thr Val Ala Trp Ser Asn Gly Arg Gly Phe Asn Ala Thr Tyr His Val
    290                 295                 300

Arg Gly Tyr Cys Leu Pro Trp Asp Arg Pro Cys Gly Leu Gly Ser Gly
305                 310                 315                 320

Leu Gly Ala Gly Glu Gly Leu Gly Glu Arg Cys Tyr Ser Glu Ala Gln
                325                 330                 335

Arg Cys Asp Gly Ser Trp Asp Cys Ala Asp Gly Thr Asp Glu Glu Asp
            340                 345                 350

Cys Pro Gly Cys Pro Pro Gly His Phe Pro Cys Gly Ala Ala Gly Thr
        355                 360                 365

Ser Gly Ala Thr Ala Cys Tyr Leu Pro Ala Asp Arg Cys Asn Tyr Gln
    370                 375                 380

Thr Phe Cys Ala Asp Gly Ala Asp Glu Arg Arg Cys Arg His Cys Gln
385                 390                 395                 400
```

```
Pro Gly Asn Phe Arg Cys Arg Asp Glu Lys Cys Val Tyr Glu Thr Trp
            405                 410                 415

Val Cys Asp Gly Gln Pro Asp Cys Ala Asp Gly Ser Asp Glu Trp Asp
            420                 425                 430

Cys Ser Tyr Val Leu Pro Arg Lys
            435         440
```

COMPOSITIONS AND METHODS FOR CANCER THERAPY

CROSS REFERENCE TO RELATED APPLICATIONS

This application is a U.S. national phase application of PCT International Patent Application No. PCT/US2018/063082, filed on Nov. 29, 2018, which claims claims priority to and the benefit of U.S. Provisional Patent Application No. 62/591,874 filed Nov. 29, 2017, the disclosure of each of which is incorporated herein by reference in its entirety.

GOVERNMENT SUPPORT

This invention was made with government support under grant number AI125581 awarded by The National Institutes of Health. The government has certain rights in the invention.

FIELD

The present disclosure generally relates to compositions and methods for cancer immunotherapy, as well as hematopoietic recovery following cancer treatment such as chemotherapy or irradiation.

BACKGROUND

Despite multiple preventative and therapeutic approaches, cancer is one of the major causes of death worldwide. Between 2010 and 2020, the number of new cancer cases in the United States is expected to increase by about 24% in men to more than 1 million cases per year, and by about 21% in women to more than 900.000 cases per year. The types of cancer that are expected to increase the most are melanoma in both men and women; prostate, kidney, liver, and bladder cancers in men; and lung, breast, uterine, and thyroid cancers in women. Cancer remains the second most common cause of death in the US, accounting for nearly 1 of every 4 deaths. Many cancers are difficult or impossible to treat with current approaches. Many cancers evade current treatment regimens, become resistant to treatment, or reoccur after treatment. For example, cytotoxic chemotherapy, one of the most common systemic treatment options for cancer, has limited efficacy, especially in the treatment of solid tumors.

Hematopoietic recovery is one of the key factors affecting the outcome of chemotherapy. Faster bone marrow recovery leads to fewer adverse consequences and enables patients to proceed with further courses of chemotherapy without delay. A delayed bone marrow recovery can lead to an uncontrolled infection that results in treatment failure. The hematopoietic toxicity of chemotherapy is an important factor in determining the doses for treatment regimens. Drugs such as NEULASTA® and NEUPOGEN® (G-CSF) are currently used to assist in hematopoietic recovery after chemotherapy. However, these drugs are neutrophil boosters. There is currently no drug that encourages lymphoid recovery. As such, a need exists for effective methods and compositions to promote hematopoietic recovery, preferably all hematopoietic lineages including lymphoid cells, after chemotherapy.

SUMMARY

Provided herein are compositions and methods for cancer immunotherapy, as well as hematopoietic recovery following cancer treatment such as chemotherapy.

In one aspect, a method of providing cancer immunotherapy is provided, comprising inhibiting LRP10 in a subject in need thereof. In some embodiments, said inhibiting enhances tumor infiltration of lymphocytes, preferably CD8+ T cells and cytotoxic T lymphocytes, thereby providing cancer immunotherapy.

Another aspect relates to a method of enhancing hematopoietic recovery, comprising inhibiting LRP10 in a subject in need thereof. In various embodiments, said inhibiting enhances recovery of all hematopoietic lineages, preferably lymphoid lineages. In some embodiments, the subject has received chemotherapy and/or radiotherapy.

In various embodiments, methods and use disclosed herein can include administering to the subject an effective amount of anti-LRP10 antibody or antigen-binding fragment thereof, or a soluble receptor for one or more LRP10 ligands (e.g., an LRP10-Fc chimera).

Another aspect relates to use of an LRP10 inhibitor or competitor for the manufacture of a medicament for cancer immunotherapy. In some embodiments, said LRP10 inhibitor or competitor enhances tumor infiltration of lymphocytes, preferably CD8+ T cells and cytotoxic T lymphocytes, thereby providing cancer immunotherapy.

A further aspect relates to use of an LRP10 inhibitor or competitor for the manufacture of a medicament for hematopoietic recovery. In some embodiments, said LRP10 inhibitor or competitor enhances recovery of all hematopoietic lineages, preferably lymphoid lineages, in a patient who has received chemotherapy and/or radiotherapy.

In certain embodiments, said LRP10 inhibitor is anti-LRP10 antibody or antigen-binding fragment thereof, preferably binding to LRP10 ectodomain. In some embodiments, said LRP10 competitor is an engineered, soluble receptor for one or more LRP10 ligands, wherein said receptor competes for binding with endogenous LRP10 (e.g., an LRP10-Fc chimera).

Also disclosed herein is an anti-LRP10 antibody, or antigen binding fragment thereof, optionally for use in cancer immunotherapy and/or hematopoietic recovery, comprising one or more of the following CDRs:

```
VL CDR1 (SEQ ID NO: 33):
RASQSISSYLN

VL CDR2 (SEQ ID NO: 62):
X1ASX2LQS (X1 = N, A, R, D; X2 = D, P. R, A, L, T)

VL CDR3 (SEQ ID NO: 63):
QQX3X4X5X6PX7T (X3 = S, V, P, A, I, T, N; X4 = S,
A, T, D, K; X5 = R, S, T, A, Y; X6 = T, L, Y, R,
G; X7 = T, N, L, G)

VH CDR1 (SEQ ID NO: 64):
SX8AMS (X8 = Q, Y)

VH CDR2 (SEQ ID NO: 65):
X9IX10X11X12GX13X14TX15YADSVKG (X9 = S, Q, V;

X10 = P, G, S, Q, A, Y; X11 = P, T, R, S; X12 = G,

M, T, Q, R, S; X13 = P, R, N, T, Q, A; X14 = N, P,

S, G, A, T; X15 = K, T, Y, E)

VH CDR3 (SEQ ID NO: 66):
X16X17X18X19FDY (X16 = S, D, N; X17 = Y, G, A, S,
R, T; X18 = P, K, T, R, H, A; X19 = S, K, T)
```

In some embodiments, the antibody or fragment thereof can include one or more of the following CDRs:

```
VL CDR1 (SEQ ID NO: 33):
RASQSISSYLN

VL CDR2 (SEQ ID NO: 34):
NASDLQS

VL CDR2 (SEQ ID NO: 35):
AASPLQS

VL CDR2 (SEQ ID NO: 36):
RASRLQS

VL CDR2 (SEQ ID NO: 37):
AASALQS

VL CDR2 (SEQ ID NO: 38):
DASLLQS

VL CDR2 (SEQ ID NO: 39):
AASTLQS

VL CDR3 (SEQ ID NO: 40):
QQSSRTPTT

VL CDR3 (SEQ ID NO: 41):
QQVARTPNT

VL CDR3 (SEQ ID NO: 42):
QQPTSLPLT

VL CDR3 (SEQ ID NO: 43):
QQADSYPTT

VL CDR3 (SEQ ID NO: 44):
QQIKTRPTT

VL CDR3 (SEQ ID NO: 45):
QQTSAGPGT

VL CDR3 (SEQ ID NO: 46):
QQNDYYPTT

VH CDR1 (SEQ ID NO: 47):
SQAMS

VH CDR1 (SEQ ID NO: 48):
SYAMS

VH CDR2 (SEQ ID NO: 49):
QIGTMGRPTTYADSVKG

VH CDR2 (SEQ ID NO: 50):
SISTTGNSTYYADSVKG

VH CDR2 (SEQ ID NO: 51):
VIQRQGTGTEYADSVKG

VH CDR2 (SEQ ID NO: 52):
SIPSRGQATKYADSVKG

VH CDR2 (SEQ ID NO: 53):
SIATTGNTTYYADSVKG

VH CDR2 (SEQ ID NO: 54):
SIPPGGPNTKYADSVKG

VH CDR2 (SEQ ID NO: 55):
SIYTSGAATTYADSVKG

VH CDR3 (SEQ ID NO: 56):
SYPSFDY

VH CDR3 (SEQ ID NO: 57):
SGKKFDY

VH CDR3 (SEQ ID NO: 58):
DATSFDY

VH CDR3 (SEQ ID NO: 59):
NSRTFDY

VH CDR3 (SEQ ID NO: 60):
SRHTFDY

VH CDR3 (SEQ ID NO: 61):
NTATFDY
```

In some embodiments, the antibody or fragment thereof can have a VL sequence selected from the group consisting of SEQ ID NOS: 1, 5, 7, 11, 15, 19, and 23 and a VH sequence selected from the group consisting of SEQ ID NOS: 2, 8, 12, 16, 20, 24, 27, and 29.

A further aspect relates to a soluble receptor for one or more LRP10 ligands, wherein said soluble receptor competes with endogenous LRP10 for binding with the one or more LRP10 ligands. In some embodiments, the soluble receptor is an LRP10-Fc chimera.

In some embodiments, in a migration assay, a cell (e.g., hematopoietic stem cell or T cell) contacted with the antibody or fragment thereof or the soluble receptor for one or more LRP10 ligands (e.g., an LRP10-Fc chimera) migrates toward a chemotactic stimulus more rapidly than a control cell that is not contacted with the antibody or fragment thereof or the soluble receptor, wherein preferably the chemotactic stimulus is selected from C-X-C motif chemokine 12 (CXCL12), C-X-C motif chemokine 10 (CXCL10), sphingosine-1-phosphate (S1P), C-C motif ligand 2 (CCL2), and/or C-C motif ligand 21 (CCL21).

In certain embodiments, a cell (e.g., hematopoietic stem cell or T cell) contacted with the antibody or fragment thereof or the soluble receptor for one or more LRP10 ligands (e.g., an LRP10-Fc chimera) shows increased expression of Frizzled and/or P21 compared to a control cell that is not contacted with the antibody or fragment thereof or the soluble receptor.

Also provided herein is a pharmaceutical composition for cancer immunotherapy and/or hematopoietic recovery, comprising the antibody or fragment thereof and/or the soluble receptor for one or more LRP10 ligands (e.g., an LRP10-Fc chimera) disclosed herein and a pharmaceutically acceptable carrier. Use of the antibody or fragment thereof and/or the soluble receptor for one or more LRP10 ligands (e.g., an LRP10-Fc chimera) disclosed herein, for the manufacture of a medicament for cancer immunotherapy and/or hematopoietic recovery, is also provided.

A method for identifying an LRP10 inhibitor is also provided, comprising contacting a cell (e.g., hematopoietic stem cell or T cell) with a test agent, wherein an increase in migration toward a chemotactic stimulus compared to a control cell that is not contacted with the test agent indicates that the test agent is an LRP10 inhibitor, wherein preferably the chemotactic stimulus is selected from C-X-C motif chemokine 12 (CXCL12), C-X-C motif chemokine 10 (CXCL10), sphingosine-1-phosphate (SIP), C-C motif ligand 2 (CCL2), and/or C-C motif ligand 21 (CCL21). In some embodiments, the test agent is an antibody or antigen-binding fragment thereof, or a soluble receptor for one or more LRP10 ligands (e.g., an LRP10-Fc chimera).

Another method for identifying an LRP10 inhibitor is also provided, which includes contacting a cell (e.g., hematopoietic stem cell or T cell) with a test agent, wherein an increase in expression of p21 compared to a control cell that is not contacted with the test agent indicates that the test agent is an LRP10 inhibitor. In some embodiments, the test agent is an antibody or antigen-binding fragment thereof, or a soluble receptor for one or more LRP10 ligands (e.g., an LRP0-Fc chimera).

DETAILED DESCRIPTION

Figure 1:
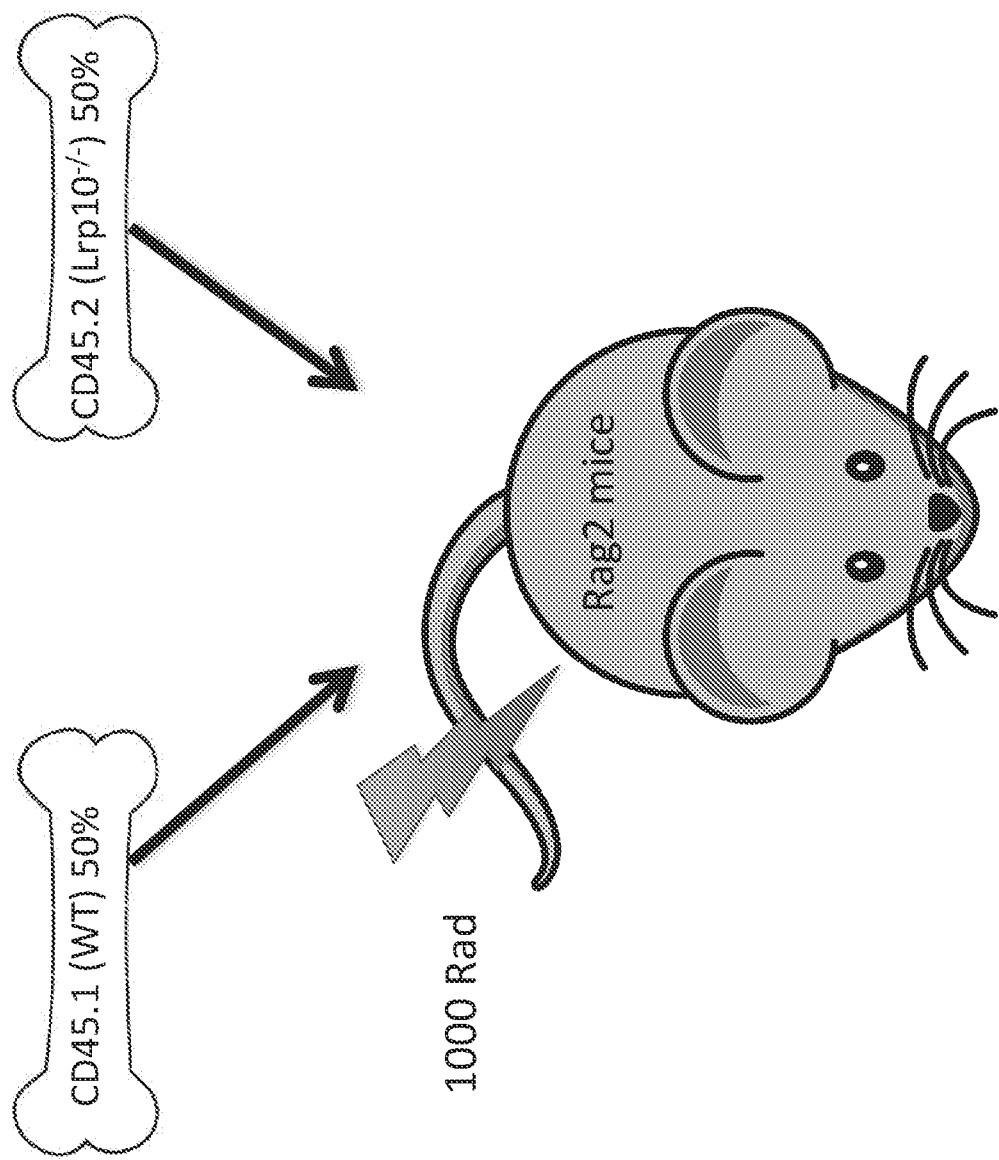
FIG. 1 is a schematic showing transplantation of bone marrow cells from C57BL/6 mice (CD45.1), CRISPR-Lrp10 KO mice (CD45.2), or a 1:1 mixture into irradiated Rag2$^{-/-}$ recipient mice.

It is to be understood that both the foregoing general description and the following detailed description are exemplary and explanatory only and are not restrictive of the compositions and methods of the present disclosure.

Disclosed herein are compositions and methods related to inhibiting LRP10, enhancing hematopoietic recovery in a subject after chemotherapy or irradiation, and/or improving cancer immunotherapy, as well as kits that can be used in such methods. One aspect of the present disclosure relates to the surprising discovery that a mutation in Lrp10, or knockout of Lrp10, causes a phenotype characterized by increased speed of hematopoietic recovery, and in the case of mixed chimeras, out-competition of the wild-type (WT) cells by mutant cells. As such, an inhibitor of LRP10, such as an antibody, can be used to promote hematopoietic recovery in a subject after, e.g., chemotherapy or irradiation. In addition, without wishing to be bound by theory, it is believed that LRP10 blockade may be equivalent to a checkpoint blockade, allowing CD8+ T cells to infiltrate tumors more effectively than they otherwise would. As such, LRP10 inhibition can also be used to augment immunotherapy treatment of a cancer (e.g., by increasing the number of tumor infiltrating T lymphocytes).

LRP10 is a single-spanning plasma membrane receptor, previously of unknown function. Unexpectedly. Lrp10 KO T cells migrate toward a chemotactic stimulus more rapidly than WT cells. Furthermore, Lrp10 KO T cells show high expression of Fizzled and p21, p21 being an end-product of the non-canonical Wnt signaling pathway. In some embodiments, in a chemotaxis migration assay, Frizzled expression and/or p21 expression can be used as a marker in screening for inhibitors of LRP10.

Therefore, LRP10 inhibitors such as the antibodies and soluble receptors disclosed herein, can be used to treat a subject, by improving hematopoietic recovery after chemotherapy or irradiation, and/or improving cancer immunotherapy.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein, the term "about" means acceptable variations within 20%, more preferably within 10% and most preferably within 5% of the stated value.

"Lrp10" and "LRP10," also known as LRP9, LRP-10, MST087, or MSTP087 are used interchangeably and refer to LDL receptor related protein 10, with "Lrp10" generally referring to the gene or mRNA and "LRP10" the protein product unless otherwise noted. It should be understood that the terms include the complete gene, the cDNA sequence, the complete amino acid sequence, or any fragment or variant thereof. In some embodiments, the LRP10 is human LRP10.

As used herein, the term "LRP10 inhibitor" is intended to include therapeutic agents that inhibit, down-modulate, suppress or down-regulate LRP10 activity. The term is intended to include chemical compounds, such as small molecule inhibitors and biologic agents (e.g., antibodies), interfering RNA (shRNA, siRNA), soluble antagonists, gene editing/silencing tools (CRISPR/Cas9, TALENs) and the like.

An "anti-LRP10 antibody" is an antibody that immunospecifically binds to LRP10 (e.g., its extracellular domain). The antibody may be an isolated antibody. Such binding to LRP10 exhibits a K$_d$ with a value of, e.g., no greater than 1 µM, no greater than 100 nM or no greater than 50 nM. Kd can be measured by any methods known to one skilled in the art, such as a surface plasmon resonance assay or a cell binding assay. An anti-LRP10 antibody may be a monoclonal antibody, or antigen-binding fragments thereof. Exemplary anti-LRP10 antibodies may inhibit LRP10 binding with its ligand(s) (e.g., an endogenous ligand).

An "antibody," as used herein is a protein consisting of one or more polypeptides comprising binding domains that bind to a target epitope. The term antibody includes monoclonal antibodies comprising immunoglobulin heavy and light chain molecules, single heavy chain variable domain antibodies, and variants and derivatives thereof, including chimeric variants of monoclonal and single heavy chain variable domain antibodies. Binding domains are substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. For most vertebrate organisms, including humans and murine species, the typical immunoglobulin structural unit comprises a tetramer that is composed of two identical pairs of polypeptide chains, each pair having one "light" (about 25 kD) and one "heavy" chain (about 50-70 kD). "$V_L$" and "$V_H$" refer to the variable domains of these light and heavy chains respectively. "$C_L$" and "$C_H$" refer to the constant domains of the light and heavy chains. Loops of β-strands, three each on the $V_L$ and $V_H$ are responsible for binding to the antigen, and are referred to as the "complementarity determining regions" or "CDRs". The "Fab" (fragment, antigen-binding) region includes one constant and one variable domain from each heavy and light chain of the antibody, i.e., $V_L$, $C_L$, $V_H$ and $C_H1$.

Antibodies include intact immunoglobulins as well as antigen-binding fragments thereof. The term "antigen-binding fragment" refers to a polypeptide fragment of an antibody which binds antigen or competes with intact antibody (i.e., with the intact antibody from which they were derived) for antigen binding (i.e., specific binding). Antigen binding fragments can be produced by recombinant or biochemical methods that are well known in the art. Exemplary antigen-binding fragments include Fv, Fab, Fab', (Fab')$_2$, CDR, paratope and single chain Fv antibodies (scFv) in which a $V_H$ and a $V_L$ chain are joined together (directly or through a peptide linker) to form a continuous polypeptide.

Another class of antibodies known as heavy chain antibodies (HCA, also referred to as two-chain or two-chain heavy chain antibodies) have been reported in camelids such as dromedary camels, Bactrian camels, wild Bactrian camels, llamas, alpacas, vicuflas, and guanacos (Hamers-Casterman et al., Nature, 363, 446-448 (1993); Wesolowski et al., Med. Microbiol. Immunol (2009) 198:157-174; see also U.S. Pat. Nos. 5,759,808; 5,800,988; 5,840,526; and 5,874,541). Compared with conventional four-chain immunoglobulins of IgG-type, which are also produced by camelids, these antibodies lack the light chains and CH1 domains of conventional immunoglobulins, and their variable domains are sometimes designated "$V_HH$". $V_HH$ can include four framework regions or "FR", FR1, FR2, FR3 and FR4. The framework regions are interrupted by three CDRs, CDR1, CDR2 and CDR3. One of the salient features of these naturally occurring heavy chain antibodies is the predominant presence of Glu, Arg and Gly at VL interface positions 44, 45 and 47 (Kabat numbering), respectively, of their $V_HH$. The same positions in the VH of conventional four-chain antibodies (are almost exclusively occupied by Gly, Leu and Trp. These differences are thought to be responsible for the high solubility and stability of camelid HCA variable domain ($V_HH$), as compared with the relative insolubility of VH domain of the conventional four-chain antibodies. Two more salient features of camelid $V_HH$ domains are their comparatively longer CDR3 and high incidence of cysteine pairs in CDRs. It appears that cysteine pairs mediate the formation of a disulfide bridge and are therefore involved in modulating the surface topology of the antibody combining site. In the crystal structure of a camel sdAb-lysozyme complex, a rigid loop protruding from the sdAb and partly stabilized by a CDR disulfide linkage extends out of the combining site and penetrates deeply into the lysozyme active site (Desmyter et al., Nature Struct. Biol., 3, 803-811 (1996)).

Antibodies also include variants, chimeric antibodies and humanized antibodies. The term "antibody variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

As described herein, the amino acid residues of an antibody, including VHH, can be numbered according to the general numbering of Kabat (Kabat, et al. (1991) Sequences of Proteins of Immunological Interest, 5th edition. Public Health Service, NIH, Bethesda, Md.).

The term "binding" as used herein in the context of binding between an antibody, such as a VHH, and an epitope of LRP10 as a target, refers to the process of a non-covalent interaction between molecules. Preferably, said binding is specific. The specificity of an antibody can be determined based on affinity. A specific antibody can have a binding affinity or dissociation constant Kd for its epitope of less than $10^{-7}$ M preferably less than $10^{-8}$ M.

The term "affinity" refers to the strength of a binding reaction between a binding domain of an antibody and an epitope. It is the sum of the attractive and repulsive forces operating between the binding domain and the epitope. The term affinity, as used herein, refers to the dissociation constant, $K_d$.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "cancer" broadly refers to an uncontrolled, abnormal growth of a host's own cells leading to invasion of surrounding tissue and potentially tissue distal to the initial site of abnormal cell growth in the host. Major classes include carcinomas which are cancers of the epithelial tissue (e.g., skin, squamous cells); sarcomas which are cancers of the connective tissue (e.g., bone, cartilage, fat, muscle, blood vessels, etc.); leukemias which are cancers of blood forming tissue (e.g., bone marrow tissue); lymphomas and myelomas which are cancers of immune cells; and central nervous system cancers which include cancers from brain and spinal tissue. "Cancer(s)," "neoplasm(s)," and "tumor(s)" are used herein interchangeably. As used herein, "cancer" refers to all types of cancer or neoplasm or malignant tumors including leukemias, carcinomas and sarcomas, whether new or recurring. Specific examples of cancers are: carcinomas, sarcomas, myelomas, leukemias, lymphomas and mixed type tumors. Non-limiting examples of cancers are new or recurring cancers of the brain, melanoma, bladder, breast, cervix, colon, head and neck, kidney, lung, non-small cell lung, mesothelioma, ovary, prostate, sarcoma, stomach, uterus and medulloblastoma.

The term "cellular augmentation" or "immunotherapy augmentation" broadly refers to the influx of cells or expansion of cells in an environment that are not substantially present in the environment prior to administration of a composition and not present in the composition itself. Cells that augment the environment include immune cells, stromal cells, bacterial and fungal cells. Environments of particular interest are the microenvironments where cancer cells reside or locate. In some instances, the microenvironment is a tumor microenvironment or a tumor draining lymph node. In other instances, the microenvironment is a pre-cancerous tissue site or the site of local administration of a composition or a site where the composition will accumulate after remote administration.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. Methods for epitope mapping are well known in the art, such as X-ray co-crystallography, array-based oligo-peptide scanning, site-directed mutagenesis, high throughput mutagenesis mapping and hydrogen-deuterium exchange.

The site on the antibody that binds the epitope is referred to as "paratope," which typically include amino acid residues that are in close proximity to the epitope once bound. See Sela-Culang et al., Front Immunol. 2013; 4: 302.

"Immunohistochemistry" or "IHC" refers to the process of detecting an antigen in cells of a tissue section allowing the binding and subsequent detection of antibodies immunospecifically recognizing the antigen of interest in a biological tissue. For a review of the IHC technique, see, e.g., Ramos-Vara et al., Veterinary Pathology January 2014 vol. 51 no. 1, 42-87, incorporated herein by reference in its entirety. To evaluate IHC results, different qualitative and semi-quantitative scoring systems have been developed. See, e.g., Fedchenko et al., Diagnostic Pathology, 2014; 9: 221, incorporated herein by reference in its entirety. One example is the H-score, determined by adding the results of multiplication of the percentage of cells with staining intensity ordinal value (scored from 0 for "no signal" to 3 for "strong signal") with 300 possible values.

"Immunospecific" or "immunospecifically" (sometimes used interchangeably with "specifically") refer to antibodies that bind via domains substantially encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds immunospecifically to a cognate antigen with a $K_d$ with a value of no greater than 50 nM, as measured by a surface plasmon resonance assay or a cell binding assay. The use of such assays is well known in the art.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

"Immunotherapy" is treatment that uses a subject's immune system to treat cancer and includes, for example innate immunotherapy, adoptive transfer of tumor infiltrating lymphocytes ("IL"), active specific immunotherapy ("ASI"), adoptive cellular immunotherapy ("AC"), adoptive immunotherapy, cancer antigen immunotherapy ("CAI"), cytokine-expressing cancer immunotherapy, monoclonal antibodies, therapeutic cancer vaccines, oncolytic virus immunotherapy, adoptive T cell transfer, cytokine immunotherapy, adjuvant immunotherapy.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The terms "cross-compete", "cross-competition", "cross-block", "cross-blocked" and "cross-blocking" are used interchangeably herein to mean the ability of an antibody or fragment thereof to interfere with the binding directly or indirectly through allosteric modulation of the anti-LRP10 antibodies of the present disclosure to the target LRP10. The extent to which an antibody or fragment thereof is able to interfere with the binding of another to the target, and therefore whether it can be said to cross-block or cross-compete according to the present disclosure, can be determined using competition binding assays. One particularly suitable quantitative cross-competition assay uses a FACS- or an AlphaScreen-based approach to measure competition between the labelled (e.g. His tagged, biotinylated or radio-active labelled) an antibody or fragment thereof and the other an antibody or fragment thereof in terms of their binding to the target. In general, a cross-competing antibody or fragment thereof is for example one which can bind to the target in the cross-competition assay such that, during the assay and in the presence of a second antibody or fragment thereof, the recorded displacement of the immunoglobulin single variable domain or polypeptide according to the disclosure is up to 100% (e.g., in FACS based competition assay) of the maximum theoretical displacement (e.g., displacement by cold (e.g., unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% to 100%.

The terms "suppress", "suppression", "inhibit", "inhibition", "neutralize" and "neutralizing" as used interchangeably herein, refer to any statistically significant decrease in biological activity (e.g., LRP10 activity or tumor cell growth), including full blocking of the activity. For example, "inhibition" can refer to a decrease of about 10%, 20%, 30%, 40%, 50%, 60%, 70%, 80%, 90%, or 100% in biological activity.

The term "subject" or "patient" includes a human or other mammalian animal that receives either prophylactic or therapeutic treatment.

The terms "treat," "treating," and "treatment," as used herein, refer to therapeutic or preventative measures such as those described herein. The methods of "treatment" employ administration to a patient a LRP10 inhibitor provided herein, for example, a patient having a cancer, in order to prevent, cure, delay, reduce the severity of, or ameliorate one or more symptoms of the cancer or recurring cancer, or in order to prolong the survival of a patient beyond that expected in the absence of such treatment. The methods of "treatment" also employ administration to a patient a LRP10 inhibitor provided herein (e.g., an antibody) to enhance hematopoietic recovery after chemotherapy or irradiation, and/or improving cancer immunotherapy in a patient beyond that expected in the absence of such treatment.

The term "effective amount," as used herein, refers to that amount of an agent, such as a LRP10 inhibitor, for example an anti-LRP10 antibody, which is sufficient to promote hematopoietic recovery in a subject after chemotherapy or irradiation, and/or effect treatment (e.g., immunotherapy), prognosis or diagnosis of a cancer, when administered to a patient. A therapeutically effective amount will vary depending upon the patient and disease condition being treated, the weight and age of the patient, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, as provided herein. Dosing may be, e.g., every week, every 2 weeks, every three weeks, every 4 weeks, every 5 weeks or every 6 weeks. Dosage regimens may be adjusted to provide the optimum therapeutic response. An effective amount is also one in which any toxic or detrimental effects (side effects) of the agent are minimized and/or outweighed by the beneficial effects. Administration may be intravenous at exactly or about 6 mg/kg or 12 mg/kg weekly, or 12 mg/kg or 24 mg/kg biweekly. Additional dosing regimens are described below.

Other terms used in the fields of recombinant nucleic acid technology, microbiology, immunology, antibody engineering, and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, *Molecular Cloning: A Laboratory Manual.* 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Various aspects and embodiments are described in further detail in the following subsections.

LRP10

The low-density lipoprotein receptor (LDLR) is a cell surface receptor that mediates lipoprotein metabolism in the body. In humans, the LDLR gene resides on chromosome 19 at the band 19p13.2 and is split into 18 exons. Genetic deficiencies of the LDLR gene give rise to familial hypercholesterolemia, one of the most common genetic diseases in humans (Goldstein, J. L. et al. The Metabolic Basis of Inherited Disease, sixth ed., McGraw-Hill, New York, 1989, pp. 1215-1250). The LDLR gene encodes a single transmembrane protein that consists of five functional domains: a ligand binding domain composed of multiple cysteine-rich repeats; an epidermal growth factor (EGF) precursor homology domain with the sequence Tyr-Trp-Thr-Asp (YWTD) that forms a β-propeller structure; an O-linked sugar domain; a transmembrane domain; and a cytoplasmic domain with a coated pit targeting signal (H. Tolleshaug, J. L. et al., Cell, 30 (1982), pp. 715-724). In addition to LDLR, the following receptors are considered to be part of the LDLR gene family in mammals: very low-density lipoprotein receptor (VLDLR); apolipoprotein E receptor 2 (ApoER2 also known as LRP8); LDLR-related protein-1 (LRP1 also known as CD91, or α2macroglobulin receptor, α2MR); LRP2 (also known as megalin, or glycoprotein 330, GP330); LRP3 (closely resembles ST7 and LRP9); LRP4 (also known as corin); LRP5 (also known as LRP7); LRP6 (also known as ADCAD2 or STHAG7); LRP10 (also known as LRP9, LRP-10, MST087, or MSTP087), and LR11 (also known as sorLA) (Jeong, Y. H. Biochem Biophys Res Commun. 2010 Jan. 1; 391(1):1110-5). Most of the LDLR gene family is structurally similar to LDLR, so it has been thought that most members of this family play a primary role in lipoprotein metabolism. Other roles for the LDLR gene family are the following: (1) VLDLR and ApoER2 transmit the extracellular Reelin signal to migrating neurons, which governs neuronal layering of the brain during embryonic brain development (Trommsdorff, M. et al., Cell, 97 (1999), pp. 689-701); (2) LRP1 regulates cellular entry of viruses and toxins and protects from atherosclerosis by modulating plate-derived growth factor receptor-β signaling in the vascular wall (Herz, J. et al., Curr. Opin. Lipidol., 15 (2004), pp. 175-181); (3) LRP2 acts as an endocytic receptor that mediates the availability of several extracellular signaling molecules such as vitamin D, vitamin A and sex steroids (Hammes, A. et al., Cell, 122 (2005), pp. 751-762); (4) LRP3 modulates cellular uptake of β-VLDL; (5) LRP4 serves as a type II transmembrane serine protease, and as a pro-atrial natriuretic peptide-converting enzyme that regulates blood pressure (Yan, W. et al., Proc. Nat. Acad. Sci. USA, 97 (2000), pp. 8525-8529); (6) LRP5 and LRP6 bind Wnt and Frizzled proteins, and activate the Wnt signaling pathway involved in cell proliferation, cell polarity and cell fate determination (Tami, K. et al., Nature, 407 (2000), pp. 530-535), and (7) LR11 may participate in the development of Alzheimer's disease by modulating endocytosis of the amyloid precursor protein, which generates the amyloid 0 peptide (Herz, J. et al., Curr. Opin. Lipidol., 15 (2004), pp. 175-181).

LRP10 is a single-spanning plasma membrane receptor and consists of five functional domains characteristic of the LDLR gene family. The structural organization of LRP10 predicts that LRP10 may bind ligands similarly to the LDLR gene family, and that LRP10 likely acts as an endocytic receptor or a signal transducer (Jeong, Y. H. Biochem Biophys Res Commun. 2010 Jan. 1; 391(1):1110-5). Prior to the present disclosure, the function of LRP10 had not been elucidated.

The full gene sequence of human Lrp10 is 9,968 bp in length (GenBank ID No. NC_000014.9). The mature type I membrane protein contains 6% amino acids and has a calculated molecular mass of 74.8 kD (Sugiyama, T. et al., Biochemistry 39: 15817-15825, 2000). The human cDNA sequence of low-density lipoprotein receptor-related protein 10 isoform 2 precursor is 4,785 bp in length (GenBank ID No. NM_001329226), and the human cDNA sequence of low-density lipoprotein receptor-related protein 10 isoform 1 precursor 6,930 bp in length (GenBank ID No. NM_014045). The full gene sequence of mouse Lrp10 gene is 7,334 bp in length (GenBank ID No. NC_000080.6).

Compositions for inhibiting LRP10 and thus, enhancing hematopoietic recovery in a subject after chemotherapy or irradiation, and/or improving cancer immunotherapy in a subject are also provided. The composition can include one or more anti-LRP10 antibody disclosed herein, or antigen binding fragment thereof. In some embodiments, the anti-LRP10 antibodies disclosed herein can inhibit a LRP10 ligand (e.g., in circulation) from binding with LRP10. In some embodiments, other LRP10 inhibitors such as small molecule compounds can also be used to inhibit one or more activities of LRP10, including binding between LRP10 and its ligand. In certain embodiments, a soluble version of LRP10 can be engineered which can act to compete with the endogenous, membrane protein LRP10 to bind to LRP10 ligand, thereby indirectly inhibit binding between endogenous LRP10 and its ligand.

LRP10 Inhibitor

Inhibition of LRP10 can enhance hematopoietic recovery in a subject, e.g., after chemotherapy or irradiation, and/or provide cancer immunotherapy in a subject. As such, LRP10 inhibitors can be used as an effective agent in cancer therapeutics.

Various LRP10 inhibitors are included in the present disclosure. Examples include chemical compounds, such as small molecule inhibitors and biologic agents (e.g., antibodies) that can bind LRP10 and inhibit or decrease its activity, e.g., in a chemotaxis migration assay or Frizzled and/or p21 expression assay. Another exemplary LRP10 inhibitor is a soluble, decoy receptor that binds to one or more LRP10 ligands. Agents that regulate Lrp10 gene expression level are also included, such as interfering RNA (shRNA, siRNA) and gene editing/silencing tools (CRISPR/Cas9, TALENs, zinc finger nucleases) that are designed specifically to target the Lrp10 gene or a regulatory sequence thereto.

In some embodiments, a method for identifying an LRP10 inhibitor is provided, which can include contacting a cell with a test agent, wherein an increase in migration toward a chemotactic stimulus compared to a control cell that is not contacted with the antibody or fragment thereof indicates that the test agent is an LRP10 inhibitor, wherein preferably the chemotactic stimulus is selected from C-X-C motif chemokine 12 (CXCL12), C-X-C motif chemokine 10 (CXCL10), sphingosine-1-phosphate (SIP), C-C motif ligand 2 (CCL2), and/or C-C motif ligand 21 (CCL21).

Another method for identifying an LRP10 inhibitor can include contacting a cell with a test agent, wherein an increase in expression of Frizzled and/or P21 compared to a control cell that is not contacted with the antibody or fragment thereof indicates that the test agent is an LRP10 inhibitor.

The LRP10 inhibitor can be characterized by at least partial inhibition of proliferation (e.g., by at least 10% relative to control) of cancer cells or by at least partial inhibition of tumor growth (e.g., volume and/or metastasis) in vivo in the patient. Without wishing to be bound by theory, it is believed that in cancer, one of the major problems is a failure of CD8 T cells and their descendants, cytotoxic T lymphocytes, to infiltrate tumor masses in order to kill tumor cells. The failure to do so may depend on signaling via LRP10. Thus, functional inhibition of LRP10 using, e.g., an antibody or antigen-binding fragment thereof that binds to LRP10 can allow such infiltration to occur.

In certain embodiments, the LRP10 inhibitor is an anti-LRP10 antibody, e.g., a monoclonal antibody, or an antigen-binding fragment thereof. In certain embodiments, the anti-LRP10 antibody can be a modified, e.g., chimeric or humanized antibody derived from a mouse anti-LRP10 antibody. Methods for making modified antibodies are known in the art. In some embodiments, the anti-LRP10 antibody is an antibody or antigen binding fragment thereof which binds to an epitope present on the human LRP10 protein, e.g., the extracellular ectodomain, or a portion thereof.

In some embodiment, the anti-LRP10 antibody or antigen-binding fragment thereof can comprise one or more of the following VL (SEQ ID NOS: 1, 5, 7, 11, 15, 19, 23) and VH sequences (SEQ ID NOS: 2, 8, 12, 16, 20, 24, 27, 29). Note that for the full antibody sequence, each VL can be linked to a light chain constant region such as Ck (SEQ ID NO: 31) to form a full light chain, and each VH can be linked to a heavy chain constant region such as human IgG1 CH123 (SEQ ID NO: 32) to form a full heavy chain.

```
VL (SEQ ID NO: 1):
TDIQMTQSPSSLSASVGDRVTITCRASQSISSYLNWYQQKPGKAPKLLIY
NASDLQSGVPSRFSGSGSGTDFTLTISSLQPEDFATYYCQQSSRTPTTFG
QGTKVEIK

VL (SEQ ID NO: 5):
TDIQMTQSPSSLSASVGDRVTITCRASQSISSYLNWYQQKPGKAPKLLIY
AASPLQSGVPSRFSGSGSGTDFTLTISSLQPEDFATYYCQQVARTPNTFG
QGTKVEIK

VL (SEQ ID NO: 7):
TDIQMTQSPSSLSASVGDRVTITCRASQSISSYLNWYQQKPGKAPKLLIY
RASRLQSGVPSRFSGSGSGTDFTLTISSLQPEDFATYYCQQPTSLPLTFG
QGTKVEIK

VL (SEQ ID NO: 11):
TDIQMTQSPSSLSASVGDRVTITCRASQSISSYLNWYQQKPGKAPKLLIY
AASALQSGVPSRFSGSGSGTDFTLTISSLQPEDFATYYCQQADSYPTTFG
QGTKVEIK

VL (SEQ ID NO: 15):
TDIQMTQSPSSLSASVGDRVTITCRASQSISSYLNWYQQKPGKAPKLLIY
RASRLQSGVPSRFSGSGSGTDFTLTISSLQPEDFATYYCQQIKTRPTTFG
QGTKVEIK

VL (SEQ ID NO: 19):
TDIQMTQSPSSLSASVGDRVTITCRASQSISSYLNWYQQKPGKAPKLLIY
DASLLQSGVPSRFSGSGSGTDFTLTISSLQPEDFATYYCQQTSAGPGTFG
QGTKVEIK

VL (SEQ ID NO: 23):
TDIQMTQSPSSLSASVGDRVTITCRASQSISSYLNWYQQKPGKAPKLLIY
AASTLQSGVPSRFSGSGSGTDFTLTISSLQPEDFATYYCQQNDYYPTTFG
QGTKVEIK

VH (SEQ ID NO: 2):
MAEVQLLESGGGLVQPGGSLRLSCAASGFTFSSQAMSWVRQAPGKGLEWV
SSIPPGGPNTKYADSVKGRFTISRDNSKNTLYLQMNSLRAEDTAVYYCAK
SYPSFDYWGQGTLVTVSS

VH (SEQ ID NO: 8):
MAEVQLLESGGGLVQPGGSLRLSCAASGFTFSSYAMSWVRQAPGKGLEWV
SQIGTMGRPTTYADSVKGRFTISRDNSKNTLYLQMNSLRAEDTAVYYCAK
SGKKFDYWGQGTLVTVSS

VH (SEQ ID NO: 12):
MAEVQLLESGGGLVQPGGSLRLSCAASGFTFSSYAMSWVRLAPGKGLEWV
SSISTTGNSTYYADSVKGRFTISRDNSKNTLYLQMNSLRAEDTAVYYCAK
DATSFDYWGQGTLVTVSS

VH (SEQ ID NO: 16):
MAEVQLLESGGGLVQPGGSLRLSCAASGFTFSSYAMSWVRQAPGKGLEWV
SVIQRQGTGTEYADSVKGRFTISRDNSKNTLYLQMNSLRAEDTAVYYCAK
NSRTFDYWGQGTLVTVSS

VH (SEQ ID NO: 20):
MAEVQLLESGGGLVQPGGSLRLSCAASGFTFSSYAMSWVRQAPGKGLEWV
SSIPSRGQATKYADSVKGRFTISRDNSKNTLYLQMNSLRAEDTAVYYCAK
SRHTFDYWGQGTLVTVSS

VH (SEQ ID NO: 24):
MAEVQLLESGGGLVQPGGSLRLSCAASGFTFSSYAMSWVRQAPGKGLEWV
SSIATTGNTTYYADSVKGRFTISRDNSKNTLYLQMNSLRAEDTAVYYCAK
NTATFDYWGQGTLVTVSS

VH (SEQ ID NO: 27):
MAEVQLLESGGGLVQLGGSLRLSCAASGFTFSSQAMSWVRQAPGKGLEWV
SSIPPGGPNTKYADSVKGRFTISRDNSKNTLYLQMNSLRAEDTAVYYCAK
SYPSFDYWGQGTLVTVSS

VH (SEQ ID NO: 29):
MAEVQLLESGGGLVQPGGSLRLSCAASGFTFSSYAMSWVRQAPGKGLEWV
SSIYTSGAATTYADSVKGRFTISRDNSKNTLYLQMNSLRAEDTAVYYCAK
SYPSFDYWGQGTLVTVSS

Ck amino acid sequence (SEQ ID NO: 31):
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC IgG1 CH123 amino acid sequence (SEQ ID NO: 32):
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the anti-LRP10 antibody or antigen-binding fragment thereof can comprise one or more of the following CDRs:

```
VL CDR1 (SEQ ID NO: 33):
RASQSISSYLN

VL CDR2 (SEQ ID NO: 34):
NASDLQS

VL CDR2 (SEQ ID NO: 35):
AASPLQS
```

VL CDR2 (SEQ ID NO: 36):
RASRLQS

VL CDR2 (SEQ ID NO: 37):
AASALQS

VL CDR2 (SEQ ID NO: 38):
DASLLQS

VL CDR2 (SEQ ID NO: 39):
AASTLQS

VL CDR3 (SEQ ID NO: 40):
QQSSRTPTT

VL CDR3 (SEQ ID NO: 41):
QQVARTPNT

VL CDR3 (SEQ ID NO: 42):
QQPTSLPLT

VL CDR3 (SEQ ID NO: 43):
QQADSYPTT

VL CDR3 (SEQ ID NO: 44):
QQIKTRPTT

VL CDR3 (SEQ ID NO: 45):
QQTSAGPGT

VL CDR3 (SEQ ID NO: 46):
QQNDYYPTT

VH CDR1 (SEQ ID NO: 47):
SQAMS

VH CDR1 (SEQ ID NO: 48):
SYAMS

VH CDR2 (SEQ ID NO: 49):
QIGTMGRPTTYADSVKG

VH CDR2 (SEQ ID NO: 50):
SISTTGNSTYYADSVKG

VH CDR2 (SEQ ID NO: 51):
VIQRQGTGTEYADSVKG

VH CDR2 (SEQ ID NO: 52):
SIPSRGQATKYADSVKG

VH CDR2 (SEQ ID NO: 53):
SIATTGNTTYYADSVKG

VH CDR2 (SEQ ID NO: 54):
SIPPGGPNTKYADSVKG

VH CDR2 (SEQ ID NO: 55):
SIYTSGAATTYADSVKG

VH CDR3 (SEQ ID NO: 56):
SYPSFDY

VH CDR3 (SEQ ID NO: 57):
SGKKFDY

VH CDR3 (SEQ ID NO: 58):
DATSFDY

VH CDR3 (SEQ ID NO: 59):
NSRTFDY

VH CDR3 (SEQ ID NO: 60):
SRHTFDY

VH CDR3 (SEQ ID NO: 61):
NTATFDY

Alignments of the CDR sequences are shown in Tables 1-6.

TABLE 1

Alignment of VL CDR1 sequences

| Clone No. | Amino acid position (Kabat numbering) | | | | | | | | | | | |
|---|---|---|---|---|---|---|---|---|---|---|---|---|
| | L24 | L25 | L26 | L27 | L27A | L28 | L29 | L30 | L31 | L32 | L33 | L34 |
| AB1: L1 + H1 | R | A | S | Q | — | S | I | S | S | Y | L | N |
| AB2: L2 + H1 | R | A | S | Q | — | S | I | S | S | Y | L | N |
| AB3: L3 + H2 | R | A | S | Q | — | S | I | S | S | Y | L | N |
| AB4: L4 + H3 | R | A | S | Q | — | S | I | S | S | Y | L | N |
| AB5: L5 + H4 | R | A | S | Q | — | S | I | S | S | Y | L | N |
| AB6: L6 + H5 | R | A | S | Q | — | S | I | S | S | Y | L | N |
| AB7: L7 + H6 | R | A | S | Q | — | S | I | S | S | Y | L | N |
| AB8: L1 + H7 | R | A | S | Q | — | S | I | S | S | Y | L | N |
| AB9: L1 + H8 | R | A | S | Q | — | S | I | S | S | Y | L | N |
| Conserved sequence | R | A | S | Q | — | S | I | S | S | Y | L | N |

TABLE 2

Alignment of VL CDR2 sequences

| Clone No. | L50 | L51 | L52 | L53 | L54 | L55 | L56 |
|---|---|---|---|---|---|---|---|
| AB1: L1 + H1 | N | A | S | D | L | Q | S |
| AB2: L2 + H1 | A | A | S | P | L | Q | S |
| AB3: L3 + H2 | R | A | S | R | L | Q | S |
| AB4: L4 + H3 | A | A | S | A | L | Q | S |
| AB5: L5 + H4 | R | A | S | R | L | Q | S |
| AB6: L6 + H5 | D | A | S | L | L | Q | S |
| AB7: L7 + H6 | A | A | S | T | L | Q | S |
| AB8: L1 + H7 | N | A | S | D | L | Q | S |
| AB9: L1 + H8 | N | A | S | D | L | Q | S |
| Conserved sequence | X1 | A | S | X2 | L | Q | S |

(X1 = N, A, R, D; X2 = D, P, R, A, L, T)

TABLE 3

Alignment of VL CDR3 sequences

| Clone No. | L89 | L90 | L91 | L92 | L93 | L94 | L95 | L95A | L96 | L97 |
|---|---|---|---|---|---|---|---|---|---|---|
| AB1: L1 + H1 | Q | Q | S | S | R | T | P | — | T | T |
| AB2: L2 + H1 | Q | Q | V | A | R | T | P | — | N | T |
| AB3: L3 + H2 | Q | Q | P | T | S | L | P | — | L | T |
| AB4: L4 + H3 | Q | Q | A | D | S | Y | P | — | T | T |
| AB5: L5 + H4 | Q | Q | I | K | T | R | P | — | T | T |
| AB6: L6 + H5 | Q | Q | T | S | A | G | P | — | G | T |
| AB7: L7 + H6 | Q | Q | N | D | Y | Y | P | — | T | T |
| AB8: L1 + H7 | Q | Q | S | S | R | T | P | — | T | T |
| AB9: L1 + H8 | Q | Q | S | S | R | T | P | — | T | T |
| Conserved sequence | Q | Q | X3 | X4 | X5 | X6 | P | — | X7 | T |

(X3 = S, V, P, A, I, T, N; X4 = S, A, T, D, K; X5 = R, S, T, A, Y; X6 = T, L, Y, R, G; X7 = T, N, L, G)

Alignment of VH CDR1 sequences

| Clone No. | H31 | H32 | H33 | H34 | H35 | H35A |
|---|---|---|---|---|---|---|
| AB1: L1 + H1 | S | Q | A | M | S | — |
| AB2: L2 + H1 | S | Q | A | M | S | — |
| AB3: L3 + H2 | S | Y | A | M | S | — |
| AB4: L4 + H3 | S | Y | A | M | S | — |
| AB5: L5 + H4 | S | Y | A | M | S | — |
| AB6: L6 + H5 | S | Y | A | M | S | — |
| AB7: L7 + H6 | S | Y | A | M | S | — |
| AB8: L1 + H7 | S | Q | A | M | S | — |
| AB9: L1 + H8 | S | Y | A | M | S | — |
| Conserved sequence | S | X8 | A | M | S | — |

(X8 = Q, Y)

TABLE 5

Alignment of VH CDR2 sequences

| Clone No. | H50 | H51 | H52 | H52A | H53 | H54 | H55 | H56 | H57 | H58 | H59 | H60 | H61 | H62 | H63 | H64 | H65 |
|---|---|---|---|---|---|---|---|---|---|---|---|---|---|---|---|---|---|
| AB1: L1 + H1 | S | I | P | P | G | G | P | N | T | K | Y | A | D | S | V | K | G |
| AB2: L2 + H1 | S | I | P | P | G | G | P | N | T | K | Y | A | D | S | V | K | G |
| AB3: L3 + H2 | Q | I | G | T | M | G | R | P | T | T | Y | A | D | S | V | K | G |
| AB4: L4 + H3 | S | I | S | T | T | G | N | S | T | Y | Y | A | D | S | V | K | G |
| AB5: L5 + H4 | V | I | Q | R | Q | G | I | G | T | E | Y | A | D | S | V | K | G |
| AB6: L6 + H5 | S | I | P | S | R | G | Q | A | T | K | Y | A | D | S | V | K | G |
| AB7: L7 + H6 | S | I | A | T | T | G | N | T | T | Y | Y | A | D | S | V | K | G |
| AB8: L1 + H7 | S | I | P | P | G | G | P | N | T | K | Y | A | D | S | V | K | G |

TABLE 5-continued

Alignment of VH CDR2 sequences

| | Amino acid position (Kabat numbering) | | | | | | | | | | | | | | | |
|---|---|---|---|---|---|---|---|---|---|---|---|---|---|---|---|---|
| Clone No. | H50 | H51 | H52 | H52A | H53 | H54 | H55 | H56 | H57 | H58 | H59 | H60 | H61 | H62 | H63 | H64 | H65 |
| AB9: L1 + H8 | S | I | Y | T | S | G | A | A | T | T | Y | A | D | S | V | K | G |
| Conserved sequence | X9 | I | X10 | X11 | X12 | G | X13 | X14 | T | X15 | Y | A | D | S | V | K | G |

(X9 = S, Q, V; X10 = P, G, S, Q, A, Y; X11 = P, T, R, S; X12 = G, M, T, Q, R, S; X13 = P, R, N, T, Q, A; X14 = N, P, S, G, A, T; X15 = K, T, Y, E)

TABLE 6

Alignment of VH CDR3 sequences

| | Amino acid position (Kabat numbering) | | | | | | | |
|---|---|---|---|---|---|---|---|---|
| Clone No. | H95 | H96 | H97 | H98 | H99 | H100 | H100A | H101 | H102 |
| AB1: L1 + H1 | S | Y | P | S | F | — | — | D | Y |
| AB2: L2 + H1 | S | Y | P | S | F | — | — | D | Y |
| AB3: L3 + H2 | S | G | K | K | F | — | — | D | Y |
| AB4: L4 + H3 | D | A | T | S | F | — | — | D | Y |
| AB5: L5 + H4 | N | S | R | T | F | — | — | D | Y |
| AB6: L6 + H5 | S | R | H | T | F | — | — | D | Y |
| AB7: L7 + H6 | N | T | A | T | F | — | — | D | Y |
| AB8: L1 + H7 | S | Y | P | S | F | — | — | D | Y |
| AB9: L1 + H8 | S | Y | P | S | F | — | — | D | Y |
| Conserved sequence | X16 | X17 | X18 | X19 | F | — | — | D | Y |

(X16 = S, D, N; X17 = Y, G, A, S, R, T; X18 = P, K, T, R, H, A; X19 = S, K, T)

In some embodiments, the anti-LRP10 antibody or antigen-binding fragment thereof can comprise one or more of the following CDRs:

```
VL CDR1 (SEQ ID NO: 33):
RASQSISSYLN

VL CDR2 (SEQ ID NO: 62):
X1ASX2LQS (X1 = N, A, R, D; X2 = D, P. R, A, L, T)

VL CDR3 (SEQ ID NO: 63):
QQX3X4X5X6PX7T (X3 = S, V, P, A, I, T, N; X4 = S,
A, T, D, K; X5 = R, S, T, A, Y; X6 = T, L, Y, R,
G; X7 = T, N, L, G)

VH CDR1 (SEQ ID NO: 64):
SX8AMS (X8 = Q, Y)

VH CDR2 (SEQ ID NO: 65):
X9IX10X11X12GX13X14TX15YADSVKG (X9 = S, Q, V;

X10 = P, G, S, Q, A, Y; X11 = P, T, R, S; X12 = G,

M, T, Q, R, S; X13 = P, R, N, T, Q, A; X14 = N, P,

S, G, A, T; X15 = K, T, Y, E)

VH CDR3 (SEQ ID NO: 66):
X16X17X18X19FDY (X16 = S, D, N; X17 = Y, G, A, S,
R, T; X18 = P, K, T, R, H, A; X19 = S, K, T)
```

Antibodies or fragments thereof that cross-compete with any of the anti-LRP10 antibody or antigen-binding fragment thereof disclosed herein in a competition binding assay are also included in the present disclosure. In some embodiments, such cross-competing antibodies can bind to the same epitope as the anti-LRP10 antibody or antigen-binding fragment thereof disclosed herein.

In certain embodiment, the anti-LRP10 antibody can comprise a mixture, or cocktail, of two or more anti-LRP10 antibodies, each of which binds to the same or a different epitope on LRP10. In one embodiment, the mixture, or cocktail, comprises three anti-LRP10 antibodies, each of which binds to the same or a different epitope on LRP10.

In another embodiment, the LRP10 inhibitor can include a nucleic acid molecule, such as an RNA molecule, that inhibits the expression or activity of LRP10. Interfering RNAs specific for Lrp10, such as shRNAs or siRNAs that specifically inhibits the expression and/or activity of Lrp10, can be designed in accordance with methods known in the art.

LRP10 Competitor

In some embodiments, the LRP10 competitor can be a soluble, decoy receptor that can bind to one or more LRP10 ligands, thereby competing with and inhibiting or decreasing the binding of the ligand to endogenous LRP10. For example, the decoy receptor may contain an amino acid sequence corresponding to all or a part of the ectodomain of LRP10 and devoid of a transmembrane region. The amino acid sequence can contain one or more substitutions, deletions, and/or additions compared to the wild-type sequence, while retaining or enhancing its binding activity with one or more LRP10 ligands. The amino acid sequence can be fused or grafted to the constant end of an antibody (e.g., IgG1) and thus, become soluble in circulation. In some embodiments, the decoy receptor can be a human LRP10-antibody Fc fragment (LRP10-Fc) chimera.

In some embodiments, the Fc domain is an IgG domain, e.g., an IgG1, IgG2, IgG3, or IgG4 Fc domain. In some embodiments, the Fc domain comprises a CH2 domain and a CH3 domain. In some embodiments, the Fc domain has dimerization activity.

In some embodiments, the Fc domain comprises an IgG1 Fc domain of SEQ ID NO: 67 or an amino acid sequence having at least 80%, 85%, 90%, 95%, 96%, 97%, 98%, or 99% identity thereto.

(SEQ ID NO: 67)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In embodiments, the Fc domain is an effector-attenuated Fc domain. In embodiments, the effector-attenuated Fc domain has reduced effector activity, e.g., compared to a wild-type IgG1 Fc domain, e.g., compared to a wild-type IgG1 Fc domain of SEQ ID NO: 67. In some embodiments, effector activity comprises antibody-dependent cellular toxicity (ADCC). In embodiments, the effector activity is reduced by 10%, 20%, 30%, 40%, 50%, 60%, 70%, 80%, 90%, 95%, or 99% in an ADCC assay, e.g., compared to a wild-type IgG1 Fc domain of SEQ ID NO: 67. In some embodiments, effector activity comprises complement dependent cytotoxicity (CDC). In embodiments, the effector activity is reduced by 10%, 20%, 30%, 40%, 50%, 60%, 70%, 80%, 90%, 95%, or 99% in a CDC assay such as a CDC assay described in Armour et al., "Recombinant human IgG molecules lacking Fc gamma receptor I binding and monocyte triggering activities." Eur J Immunol (1999) 29:2613-24" e.g., compared to a wild-type IgG1 Fc domain of SEQ ID NO: 67.

In some embodiments, the Fc domain comprises an IgG2 constant region of SEQ ID NO: 68 or fragment thereof, or an amino acid sequence having at least 80%, 85%, 90%, 95%, 96%, 97%, 98%, or 99% identity thereto.

(SEQ ID NO: 68)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

In some embodiments, the Fc domain comprises a human IgG2 Fc domain, e.g., a human IgG2 domain of SEQ ID NO: 69 or an amino acid sequence having at least 80%, 85%, 90%, 95%, 96%, 97%, 98%, or 99% identity thereto.

(SEQ ID NO: 69)
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQ

GNVFSCSVMHEALHNHYTQKSLSLSPGK

In some embodiments, the Fc domain comprises an IgG2 Da Fc domain of SEQ ID NO: 80 or an amino acid sequence having at least 80%, 85%, 90%, 95%, 96%, 97%, 98%, or 99% identity thereto. In embodiments, the Fc domain comprises one or both of A330S and P331S mutations using Kabat numbering system. In embodiments, the Fc domain is one described in Armour et al. "Recombinant human IgG molecules lacking Fc gamma receptor I binding and monocyte triggering activities." Eur J Immunol (1999) 29:2613-24.

(SEQ ID NO: 70)
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPssIEKTISKTKGQPREPQVYTLPPSREEMTKNQVSLTCLV

KGFYPSDIAVEWESNGQPENNYKTTPPMLDSDGSFFLYSKLTVDKSRWQQ

GNVFSCSVMHEALHNHYTQKSLSLSPGK

In various embodiments, the decoy receptor can be prepared such that it is stable in circulation. In some embodiments, the decoy receptor neutralizes and/or inhibits one or more LRP10 ligands, e.g., by competing with, thereby decreasing or preventing binding of the LRP10 ligands with endogenous LRP10. In certain embodiments, the decoy receptor may act more effectively than the LRP10 ectodomain alone.

The soluble receptor can be prepared by methods known in the art such as producing a fusion protein by recombinant DNA technology. The LRP10 ectodomain or a functional portion thereof (e.g., the ligand-binding fragment) can be fused to the constant end of an antibody (e.g., IgG1). For example, the DNA sequence that codes the human LRP10 ectodomain or a functional portion thereof, can be engineered to link to, optionally through a linker, the DNA sequence that codes the human gene for the Fc end of IgG1. The engineered DNA can then be expressed to produce a protein that links the LRP10 ectodomain to IgG1 Fc.

Preparation of Anti-LRP10 Antibodies

Anti-LRP10 antibodies can be made using various methods generally known in the art. For example, phage display technology can be used to screen a human antibody library, to produce a fully human monoclonal antibody for therapy. High affinity binders can be considered candidates for neutralization studies. Alternatively, a conventional monoclonal approach can be used, in which mice or rabbits can be immunized with the human protein, candidate binders identified and tested, and a humanized antibody ultimately produced by engrafting the combining sites of heavy and light chains into a human antibody encoding sequence.

Antibodies typically comprise two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of *Kabat Sequences of Proteins of Immunological Interest* (1987 and 1991, National Institutes of Health, Bethesda, Md.), Chothia & Lesk, 1987, *J. Mol. Biol.* 196: 901-917, or Chothia et al., 1989, Nature 342:878-883).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, *Nature* 256:495-497) and the human B-cell hybridoma method (Kozbor, 1984, *J. Immunol.* 133:3001; and Brodeur et al., 1987, *Monoclonal Antibody Production Techniques and Applications*, Marcel Dekker, Inc., New York, pp. 51-63).

Monoclonal antibodies may be modified for use as therapeutics. One example is a "chimeric" antibody in which a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Other examples are fragments of such antibodies, so long as they exhibit the desired biological activity. See, U.S. Pat. No. 4,816,567; and Morrison et al. (1985), *Proc. Natl. Acad. Sci. USA* 81:6851-6855. A related development is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass.

Another development is the "humanized" antibody. Methods for humanizing non-human antibodies are well known in the art (see U.S. Pat. Nos. 5,585,089, and 5,693,762; see also Cécile Vincke et al. J. Biol. Chem. 2009; 284:3273-3284 for humanization of llama antibodies). Generally, a humanized antibody is produced by a non-human animal, and then certain amino acid residues, typically from non-antigen recognizing portions of the antibody, are modified to be homologous to said residues in a human antibody of corresponding isotype. Humanization can be performed, for example, using methods described in the art (Jones et al., 1986, *Nature* 321:522-525; Riechmann et al., 1988, *Nature* 332:323-327; Verhoeyen et al., 1988, *Science* 239:1534-1536), by substituting at least a portion of a rodent variable region for the corresponding regions of a human antibody.

More recent is the development of human antibodies without exposure of antigen to human beings ("fully human antibodies"). Using transgenic animals (e.g., mice) that are capable of producing a repertoire of human antibodies in the absence of endogenous mouse immunoglobulin production, such antibodies are produced by immunization with an antigen (typically having at least 6 contiguous amino acids), optionally conjugated to a carrier. See, for example, Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of these methods, transgenic animals are produced by incapacitating the endogenous mouse immunoglobulin loci encoding the mouse heavy and light immunoglobulin chains therein, and inserting loci encoding human heavy and light chain proteins into the genome thereof. Partially modified animals, which have less than the full complement of modifications, are then cross-bred to obtain an animal having all of the desired immune system modifications. When administered an immunogen, these transgenic animals produce antibodies that are immunospecific for these antigens having human (rather than murine) amino acid sequences, including variable regions. See PCT Publication Nos. WO96/33735 and WO94/02602, incorporated by reference. Additional methods are described in U.S. Pat. No. 5,545,807, PCT Publication Nos. WO91/10741, WO90/04036, and in EP 546073B1 and EP 546073A1, incorporated by reference. Human antibodies may also be produced by the expression of recombinant DNA in host cells or by expression in hybridoma cells as described herein.

In some embodiments, phage display technology may be used to screen for therapeutic antibodies. In phage display, antibody repertoires can be displayed on the surface of filamentous bacteriophage, and the constructed library may be screened for phages that bind to the immunogen. Antibody phage is based on genetic engineering of bacteriophages and repeated rounds of antigen-guided selection and phage propagation. This technique allows in vitro selection of LRP10 monoclonal antibodies. The phage display process begins with antibody-library preparation followed by ligation of the variable heavy (VH) and variable light (VL) PCR products into a phage display vector, culminating in analysis of clones of monoclonal antibodies. The VH and VL PCR products, representing the antibody repertoire, are ligated into a phage display vector (e.g., the phagemid pComb3X) that is engineered to express the VH and VL as an scFv fused to the pIII minor capsid protein of a filamentous bacteriophage of *Escherichia coli* that was originally derived from the M13 bacteriophage. However, the phage display vector pComb3X does not have all the other genes necessary to encode a full bacteriophage in *E. coli*. For those genes, a helper phage is added to the *E. coli* that are transformed with the phage display vector library. The result is a library of phages, each expressing on its surface a LRP10 monoclonal antibody and harboring the vector with the respective nucleotide sequence within. The phage display can also be used to produce the LRP10 monoclonal antibody itself (not attached to phage capsid proteins) in certain strains of *E. Coli*. Additional cDNA is engineered, in the phage display vector, after the VL and VH sequences to allow characterization and purification of the mAb produced. Specifically, the recombinant antibody may have a hemagglutinin (HA) epitope tag and a polyhistidine to allow easy purification from solution.

Diverse antibody phage libraries are produced from ~$10^8$ independent *E. coli* transformants infected with helper phage. Using bio-panning, a library can screened for phage binding to the immunogen sequence listed above, or a fragment thereof, through the expressed surface of the monoclonal antibody. Cyclic panning allows for pulling out potentially very rare antigen-binding clones and consists of multiple rounds of phage binding to antigen (immobilized on ELISA plates or in solution on cell surfaces), washing, elution, and reamplification of the phage binders in *E. coli*. During each round, specific binders are selected out from the pool by washing away non-binders and selectively eluting binding phage clones. After three or four rounds, highly specific binding of phage clones through their surface LRP10 monoclonal antibody is characteristic for directed selection on the immobilized immunogen.

Another method is to add a C-terminal His tag, suitable for purification by affinity chromatography, to the immunogen sequence listed above. Purified protein can be inoculated into mice together with a suitable adjuvant. Monoclonal antibodies produced in hybridomas can be tested for binding to the immunogen, and positive binders can be screened as described in the assays herein.

Fully human antibodies can also be produced from phage-display libraries (as disclosed in Hoogenboom et al., 1991, *J. Mol. Biol.* 227:381; and Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT Publication No. WO99/10494, incorporated by reference, which describes the isolation of high affinity and functional agonistic antibodies for MPL- and msk-receptors using such an approach.

In some embodiments, the human LRP10 ectodomain, consisting of amino acids 18-713 of the 713 amino acid human LRP10 protein sequence, can be used as the immunogen. A fragment or portion of the LRP10 ectodomain can also be used as the immunogen. Monoclonal antibodies can be raised using one or more immunogens. Potential therapeutic anti-LRP10 antibodies can be generated.

In one example, using a mouse model having the human LRP10 ectodomain knocked into the mouse Lrp10 gene, and human T cells (Jurkat or primary T cells from human donors), monoclonal antibodies that phenocopy the knockout mutation could be tested and identified as potential anti-LRP10 antibody candidates. Monoclonal antibodies that phenocopy the knockout mutation include those that have elevated number of T cells (e.g., CD4+ and CD8+) in blood, low B:T cell ratio, and/or low NK cell count. Such tests include screening endpoint(s), such as the augmentation of Frizzled and/or P21 protein expression detected on, e.g., Western blot, and secondarily, augmentation of T cell migration and enhanced hematopoietic reconstitution after irradiation or chemotherapy. After the screening, fully human monoclonal antibodies can be developed for preclinical testing and then tested in clinical human trials for safety and efficacy. Such antibodies can be clinical candidates that can enhance the hematopoietic recovery in a subject after chemotherapy or irradiation, and/or improve cancer immunotherapy (e.g., by increasing the number of tumor infiltrating lymphocytes).

Nucleotide sequences encoding the above antibodies can be determined. Thereafter, chimeric, CDR-grafted, humanized, and fully human antibodies also may be produced by recombinant methods. Nucleic acids encoding the antibodies can be introduced into host cells and expressed using materials and procedures generally known in the art.

The disclosure provides one or more monoclonal antibodies against LRP10. Preferably, the antibodies bind LRP10 ectodomain. In preferred embodiments, the disclosure provides nucleotide sequences encoding, and amino acid sequences comprising, heavy and light chain immunoglobulin molecules, particularly sequences corresponding to the variable regions thereof. In preferred embodiments, sequences corresponding to CDRs, specifically from CDR1 through CDR3, are provided. In additional embodiments, the disclosure provides hybridoma cell lines expressing such immunoglobulin molecules and monoclonal antibodies produced therefrom, preferably purified human monoclonal antibodies against human LRP10.

The CDRs of the light and heavy chain variable regions of anti-LRP10 antibodies of the disclosure can be grafted to framework regions (FRs) from the same, or another, species. In certain embodiments, the CDRs of the light and heavy chain variable regions of anti-LRP10 antibody may be grafted to consensus human FRs. To create consensus human FRs, FRs from several human heavy chain or light chain amino acid sequences are aligned to identify a consensus amino acid sequence. The FRs of the anti-LRP10 antibody heavy chain or light chain can be replaced with the FRs from a different heavy chain or light chain. Rare amino acids in the FRs of the heavy and light chains of anti-LRP10 antibody typically are not replaced, while the rest of the FR amino acids can be replaced. Rare amino acids are specific amino acids that are in positions in which they are not usually found in FRs. The grafted variable regions from anti-LRP10 antibodies of the disclosure can be used with a constant region that is different from the constant region of anti-LRP10 antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

In some embodiments, antibodies of the disclosure can be produced by hybridoma lines. In these embodiments, the antibodies of the disclosure bind to LRP10 with a dissociation constant ($K_d$) of between approximately 4 pM and 1 µM. In certain embodiments of the disclosure, the antibodies bind to LRP10 with a $K_d$ of less than about 100 nM, less than about 50 nM or less than about 10 nM.

In preferred embodiments, the antibodies of the disclosure are of the IgG1, IgG2, or IgG4 isotype, with the IgG1 isotype most preferred. In preferred embodiments of the disclosure, the antibodies comprise a human kappa light chain and a human IgG1, IgG2, or IgG4 heavy chain. In particular embodiments, the variable regions of the antibodies are ligated to a constant region other than the constant region for the IgG1, IgG2, or IgG4 isotype. In certain embodiments, the antibodies of the disclosure have been cloned for expression in mammalian cells.

In alternative embodiments, antibodies of the disclosure can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Such procedures are exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene-mediated transfection, protoplast fusion, electroporation, encapsulation of the polynucleotide(s) in liposomes, and direct microinjection of the DNA into nuclei.

According to certain embodiments of the methods of the disclosure, a nucleic acid molecule encoding the amino acid sequence of a heavy chain constant region, a heavy chain variable region, a light chain constant region, or a light chain variable region of a LRP10 antibody of the disclosure is inserted into an appropriate expression vector using standard ligation techniques. In a preferred embodiment, the LRP10 heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, *Meth. Enzymol. Vol.* 185, Academic Press. N.Y.

Typically, expression vectors used in any of the host cells can contain sequences for plasmid maintenance and for cloning and expression of exogenous nucleotide sequences. Such sequences typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These sequences are well known in the art.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an anti-LRP10 antibody has been inserted into the proper site of the vector, the completed vector may be inserted into a suitable host cell for amplification and/or polypeptide expression. The transformation of an expression vector for an anti-LRP10 antibody into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes an anti-LRP10 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, one may select cell lines by determining which cell lines have high expression levels and produce antibodies with constitutive LRP10 binding properties. In another embodiment, one may select a cell line from the B cell lineage that does not make its own antibody but has a capacity to make and secrete a heterologous antibody (e.g., mouse myeloma cell lines NS0 and SP2/0).

Pharmaceutical Compositions and Use Thereof

In one aspect, use of LRP10 inhibitor or competitor for the manufacture of a medicament for cancer immunotherapy and/or hematopoietic recovery is provided. In another aspect, a method of suppressing tumor growth in a patient is provided, the method comprising administering to the patient an effective amount of an LRP10 inhibitor or competitor.

In another aspect, pharmaceutical compositions are provided that can be used in the methods disclosed herein, i.e., pharmaceutical compositions for enhancing hematopoietic recovery in a subject, e.g., after chemotherapy or irradiation, and/or providing cancer immunotherapy.

In some embodiments, the pharmaceutical composition comprises an LRP10 inhibitor or competitor and a pharmaceutically acceptable carrier. The LRP10 inhibitor or competitor can be formulated with the pharmaceutically acceptable carrier into a pharmaceutical composition. Additionally, the pharmaceutical composition can include, for example, instructions for use of the composition for the treatment of patients to enhance hematopoietic recovery in a subject after chemotherapy or irradiation, and/or provide cancer immunotherapy.

In one embodiment, the LRP10 inhibitor can be an anti-LRP10 antibody or antigen-binding fragment thereof.

As used herein, "pharmaceutically acceptable carrier" includes any and all solvents, dispersion media, coatings, antibacterial and antifungal agents, isotonic and absorption delaying agents, buffers, and other excipients that are physiologically compatible. Preferably, the carrier is suitable for parenteral, oral, or topical administration. Depending on the route of administration, the active compound, e.g., small molecule or biologic agent, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion, as well as conventional excipients for the preparation of tablets, pills, capsules and the like. The use of such media and agents for the formulation of pharmaceutically active substances is known in the art. Except insofar as any conventional media or agent is incompatible with the active compound, use thereof in the pharmaceutical compositions provided herein is contemplated. Supplementary active compounds can also be incorporated into the compositions.

A pharmaceutically acceptable carrier can include a pharmaceutically acceptable antioxidant. Examples of pharmaceutically-acceptable antioxidants include. (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, and injectable organic esters, such as ethyl oleate. When required, proper fluidity can be maintained, for example, by the use of coating materials, such as lecithin, by the maintenance of the required particle size in the case of dispersions, and by the use of surfactants. In many cases, it may be useful to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

These compositions may also contain functional excipients such as preservatives, wetting agents, emulsifying agents and dispersing agents.

Therapeutic compositions typically must be sterile, non-phylogenic, and stable under the conditions of manufacture and storage. The composition can be formulated as a solution, microemulsion, liposome, or other ordered structure suitable to high drug concentration.

Sterile injectable solutions can be prepared by incorporating the active compound in the required amount in an appropriate solvent with one or a combination of ingredients enumerated above, as required, followed by sterilization, e.g., by microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include vacuum drying and freeze-drying (lyophilization) that yield a powder of the active ingredient plus any additional desired ingredient from a previously sterile-filtered solution thereof. The active agent(s) may be mixed under sterile conditions with additional pharmaceutically acceptable carrier(s), and with any preservatives, buffers, or propellants which may be required.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions comprising an LRP10 inhibitor can be administered alone or in combination therapy. For example, the combination therapy can include a composition provided herein comprising an LRP10 inhibitor and at least one or more additional therapeutic agents, such as one or more chemotherapeutic agents known in the art, discussed in further detail below. Pharmaceutical compositions can also be administered in conjunction with radiation therapy and/or surgery.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Exemplary dosage ranges for administration of an antibody include: 10-1000 mg (antibody)/kg (body weight of the patient), 10-800 mg/kg, 10-600 mg/kg, 10-400 mg/kg, 10-200 mg/kg, 30-1000 mg/kg, 30-800 mg/kg, 30-600 mg/kg, 30-400 mg/kg, 30-200 mg/kg, 50-1000 mg/kg, 50-800 mg/kg, 50-600 mg/kg, 50-400 mg/kg, 50-200 mg/kg, 100-1000 mg/kg, 100-900 mg/kg, 100-800 mg/kg, 100-700 mg/kg, 100-600 mg/kg, 100-500 mg/kg, 100-400 mg/kg, 100-300 mg/kg and 100-200 mg/kg. Exemplary dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

It may be advantageous to formulate parenteral compositions in unit dosage form for ease of administration and uniformity of dosage. Unit dosage form as used herein refers to physically discrete units suited as unitary dosages for the patients to be treated; each unit contains a predetermined quantity of active agent calculated to produce the desired therapeutic effect in association with any required pharmaceutical carrier. The specification for unit dosage forms are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions disclosed herein may be varied so as to obtain an amount of the active ingredient which is effective to achieve the desired therapeutic response for a particular patient, composition, and mode of administration, without being toxic to the patient. "Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Intravenous injection and infusion are often (but not exclusively) used for antibody administration.

When agents provided herein are administered as pharmaceuticals, to humans or animals, they can be given alone or as a pharmaceutical composition containing, for example, 0.001 to 90% (e.g., 0.005 to 70%, e.g., 0.01 to 30%) of active ingredient in combination with a pharmaceutically acceptable carrier.

In certain embodiments, the methods and uses provided herein for enhancing hematopoietic recovery in a subject after chemotherapy or irradiation, and/or improving cancer immunotherapy, can comprise administration of an LRP10 inhibitor and at least one additional anti-cancer agent that is not an LRP10 inhibitor.

In one embodiment, the at least one additional anti-cancer agent comprises at least one chemotherapeutic drug. Non-limiting examples of such chemotherapeutic drugs include platinum-based chemotherapy drugs (e.g., cisplatin, carboplatin), taxanes (e.g., paclitaxel (Taxol®), docetaxel (Taxotere®), EndoTAG-1™ (a formulation of paclitaxel encapsulated in positively charged lipid-based complexes: MediGene), Abraxane® (a formulation of paclitaxel bound to albumin)), tyrosine kinase inhibitors (e.g., imatinib/Gleevec®, sunitinib/Sutent®, dasatinib/Sprycel®), and combinations thereof.

In another embodiment, the at least one additional anti-cancer agent comprises an EGFR inhibitor, such as an anti-EGFR antibody or a small molecule inhibitor of EGFR signaling. An exemplary anti-EGFR antibody is cetuximab (Erbitux®). Cetuximab is commercially available from ImClone Systems Incorporated. Other examples of anti-EGFR antibodies include matuzumab (EMD72000), panitumumab (Vectibix®; Amgen); nimotuzumab (TheraCIM™) and mAb 806. An exemplary small molecule inhibitor of the EGFR signaling pathway is gefitinib (Iressa®), which is commercially available from AstraZeneca and Teva. Other examples of small molecule inhibitors of the EGFR signaling pathway include erlotinib HCL (OSI-774; Tarceva®, OSI Pharma); lapatinib (Tykerb®, GlaxoSmithKline); canertinib (canertinib dihydrochloride, Pfizer): pelitinib (Pfizer); PKI-166 (Novartis); PD158780: and AG 1478 (4-(3-Chloroanillino)-6,7-dimethoxyquinazoline).

In yet another embodiment, the at least one additional anti-cancer agent comprises a VEGF inhibitor. An exemplary VEGF inhibitor comprises an anti-VEGF antibody, such as bevacizumab (Avastatin®; Genentech).

In still another embodiment, the at least one additional anti-cancer agent comprises an anti-ErbB2 antibody. Suitable anti-ErbB2 antibodies include trastuzumab and pertuzumab.

In one aspect, the improved effectiveness of a combination according to the disclosure can be demonstrated by achieving therapeutic synergy.

The term "therapeutic synergy" is used when the combination of two products at given doses is more efficacious than the best of each of the two products alone at the same doses. In one example, therapeutic synergy can be evaluated by comparing a combination to the best single agent using estimates obtained from a two-way analysis of variance with repeated measurements (e.g., time factor) on parameter tumor volume.

The term "additive" refers to when the combination of two or more products at given doses is equally efficacious than the sum of the efficacies obtained with of each of the two or more products, whilst the term "superadditive" refers to when the combination is more efficacious than the sum of the efficacies obtained with of each of the two or more products.

Another measure by which effectiveness (including effectiveness of combinations) can be quantified is by calculating the $\log_{10}$ cell kill, which is determined according to the following equation: $\log_{10}$ cell kill=T−C(days)/3.32×$T_d$ in which T−C represents the delay in growth of the cells, which is the average time, in days, for the tumors of the treated group (T) and the tumors of the control group (C) to have reached a predetermined value (1 g, or 10 mL, for example), and T represents the time, in days necessary for the volume of the tumor to double in the control animals. When applying this measure, a product is considered to be active if $\log_{10}$ cell kill is greater than or equal to 0.7 and a product is considered to be very active if $\log_{10}$ cell kill is greater than 2.8.

Using this measure, a combination, used at its own maximum tolerated dose, in which each of the constituents is present at a dose generally less than or equal to its maximum tolerated dose, exhibits therapeutic synergy when the $\log_{10}$ cell kill is greater than the value of the $\log_{10}$ cell kill of the best constituent when it is administered alone. In an exemplary case, the $\log_{10}$ cell kill of the combination exceeds the value of the $\log_{10}$ cell kill of the best constituent of the combination by at least one log cell kill.

Disclosed herein are compositions and methods for providing cancer immunotherapy. The method can include inhibiting LRP10 or competing for binding with endogenous LRP10 in a subject in need thereof. In certain embodiments, inhibiting LRP10 or competing for binding with endogenous LRP10 can enhance tumor infiltration of lymphocytes, preferably CD8+ T cells and cytotoxic T lymphocytes, thereby providing cancer immunotherapy. LRP10 inhibition (e.g., an anti-LRP10 antibody) can be used as a stand-alone cancer immunotherapy by, e.g., enhancing cytotoxic T lymphocytes tumor infiltration. In some embodiments, LRP10 inhibition can be used in conjunction with other cancer immunotherapy.

Also provided herein is a method of enhancing hematopoietic recovery, comprising inhibiting LRP10 or competing for binding with endogenous LRP10 in a subject in need thereof. In certain embodiments, said inhibiting enhances recovery of all hematopoietic lineages, preferably lymphoid lineages. In some embodiments, the subject has received chemotherapy and/or radiotherapy.

In various embodiments, the methods disclosed herein can include administering to the subject an effective amount of anti-LRP10 antibody or antigen-binding fragment thereof, or a decoy, soluble LRP10. In general, the effective amount can be administered therapeutically and/or prophylactically.

Treatment can be suitably administered to subjects, particularly humans, suffering from, having, susceptible to, or at risk of developing such cancer. Determination of those subjects "at risk" can be made by any objective or subjective determination by a diagnostic test or opinion of a subject or health care provider (e.g., genetic test, enzyme or protein marker, family history, and the like). Identifying a subject in need of such treatment can be in the judgment of a subject or a health care professional and can be subjective (e.g. opinion) or objective (e.g. measurable by a test or diagnostic method).

Administration of the Formulation

The formulations of the present disclosure, including but not limited to reconstituted and liquid formulations, are administered to a mammal in need of treatment with the anti-LRP10 antibodies, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e., beneath the skin) administration. For such purposes, the formulation may be injected using a syringe. However, other devices for administration of the formulation are available such as injection devices (e.g., the INJECT-EASE™ and GENJECT™ devices); injector pens (such as the GENPEN™); auto-injector devices, needleless devices (e.g., MEDIJECTOR™ and BIOJECTOR™); and subcutaneous patch delivery systems.

In a specific embodiment, the present disclosure is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to anti-LRP10 antibody, the format of the formulation used, and the discretion of the attending physician. The anti-LRP10 antibody is suitably administered to the patient at one time or over a series of treatments and may be administered to the patient at any time from diagnosis onwards. The anti-LRP10 antibody may be administered as the sole treatment or in conjunction with other drugs or therapies useful in treating the condition in question.

For anti-LRP10 antibodies, an initial candidate dosage can range from about 0.1-20 mg/kg for administration to the patient, which can take the form of one or more separate administrations. However, other dosage regimens may be useful. The progress of such therapy is easily monitored by conventional techniques.

According to certain embodiments of the present disclosure, multiple doses of an anti-LRP10 antibody (or a pharmaceutical composition comprising a combination of an anti-LRP10 antibody and any of the additional therapeutically active agents mentioned herein) may be administered to a subject over a defined time course. The methods according to this aspect of the disclosure comprise sequentially administering to a subject multiple doses of an anti-LRP10 antibody of the disclosure. As used herein, "sequentially administering" means that each dose of anti-LRP10 antibody is administered to the subject at a different point in time, e.g., on different days separated by a predetermined interval (e.g., hours, days, weeks or months). The present disclosure includes methods which comprise sequentially administering to the patient a single initial dose of an anti-LRP10 antibody, followed by one or more secondary doses of the anti-LRP10 antibody, and optionally followed by one or more tertiary doses of the anti-LRP10 antibody. The anti-LRP10 antibody may be administered at a dose of between 0.1 mg/kg to about 100 mg/kg.

The terms "initial dose," "secondary doses," and "tertiary doses," refer to the temporal sequence of administration of the anti-LRP10 antibody of the disclosure. Thus, the "initial dose" is the dose which is administered at the beginning of the treatment regimen (also referred to as the "baseline dose"); the "secondary doses" are the doses which are administered after the initial dose: and the "tertiary doses" are the doses which are administered after the secondary doses. The initial, secondary, and tertiary doses may all contain the same amount of anti-LRP10 antibody, but generally may differ from one another in terms of frequency of administration. In certain embodiments, however, the amount of anti-LRP10 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-LRP10 antibody which is administered to a patient prior to the administration of the very next dose in the sequence with no intervening doses.

The methods according to this aspect of the disclosure may comprise administering to a patient any number of secondary and/or tertiary doses of an anti-LRP10 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of, e.g., once a month (e.g., two, three, four, or more loading doses administered once a month), then the maintenance doses may be administered to the patient once every five weeks, once every six weeks, once every seven weeks, once every eight weeks, once every ten weeks, once every twelve weeks, etc.).

EXAMPLES

The following examples, including the experiments conducted and results achieved are provided for illustrative purposes only and are not to be construed as limiting the disclosure.

Example 1. Discovery of LRP10 as an Antibody Target for Use in Humans

Summary

Using ENU mutagenesis we have created random germline mutations and to date, have screened a total of 65,130 G3 mutant mice from 2,289 pedigrees for unusual flow cytometry phenotypes in peripheral blood. These mice have been carriers of a total of 126,220 point mutations affecting coding or splicing across the proteome. One pedigree (R0765) showed a phenotype in which elevated numbers of T cells (both CD4 and CD8 cells) were present in blood. Other abnormalities included a low B:T cell ratio, and a low NK cell count. The causative mutation was identified in Lrp10 (aka Lrp9), a gene encoding a member of the LDL receptor family. Similar findings were observed subsequently with other mutant alleles of the gene, and CRISPR/Cas9 targeting verified the effect with an 8 bp frameshifting deletion mutation.

Using the CRISPR knockout mice, homozygous mutant T cells were examined for migratory activity in response to stimulation with a chemokine, CXCL12. The cells showed greatly enhanced migration toward this stimulus.

When mixed with WT bone marrow at a 50:50 ratio and transplanted into irradiated WT mice, it was observed that mutant cells greatly outgrew the WT cells, suggesting much stronger proliferative activity.

We propose that neutralizing LRP10 with a suitable monoclonal antibody would assist in hematopoietic recovery after chemotherapy or irradiation, as required during cancer chemotherapy. We further propose that LRP10 blockade might be equivalent to a checkpoint blockade, allowing CD8 T cells to infiltrate tumors much more effectively than they otherwise would.

Mutant Mice and Screening

Eight- to ten-week old pure C57BL/6J background males purchased from The Jackson Laboratory were mutagenized with N-ethyl-N-nitrosourea (ENU) to create random germline mutations, as described previously (Wang T. et al., Proc Natl Acad Sci USA. 2015 Feb. 3; 112(5), PMID: 25605905). Mutagenized G0 males were bred to C57BL/6J females, and the resulting G1 males were crossed to C57BL/6J females to produce G2 mice. G2 females were backcrossed to their G1 sires to yield G3 mice. The G3 mice were screened for unusual flow cytometry phenotypes in the peripheral blood. To date, a total of 65,130 G3 mutant mice have been screened from 2,289 pedigrees. These mice have been carriers of a total of 126,220 point mutations affecting coding or splicing across the proteome.

FACS Analysis

Mutant G3 mice were generated through (N-ethyl-N-nitrosourea) ENU-mutagenesis and strategic breeding as described above. Peripheral blood was collected from G3 mice >6 weeks old by cheek bleeding. RBCs were lysed with hypotonic buffer (ebiosceince, #00-4300-54). Samples were washed with FACs staining buffer (PBS with 1% (w/v) BSA) one time at 500×g for 6 minutes. The RBC-depleted samples were stained for 1 hour at 4° C., in 100 µl 1:200 cocktail of fluorescence-conjugated antibodies to 15 cell surface markers encompassing the major immune lineages: B220 (BD Pharmingen, #557957); CD19 (BD Bioseince, #563557); IgM (BD Pharmingen, #550881); IgD, CD3ε (BD Horizon, #553062); CD4 (BD Horizon, #562464); CD8α (Biolegend, #100752); CD11b (Biolegend, #101237); CD11c (BD Horizon, #563048); F4/80 (Tonbo Bioscience, #50-4801-U100); CD44 (BD Horizon, #562464); CD62L (Tonbo Bioscience, #60-0621-U100); CD5 (BD Horizon, #562739); CD43 (BD Pharmingen, #560663); NK 1.1 (Biolegend, #564143), and 1:200 Fc block (Fisher Scientific, #352235). Flow cytometry data was collected on a BD LSR Fortessa cell analyzer and the proportions of immune cell populations in each G3 mouse were analyzed with FlowJo software. The resulting screening data were uploaded to Mutagenetix for automated mapping of causative alleles.

Discovery of LRP10 as a Modulator of Immunity

Using the above screening method, multiple G3 mice from pedigree R0765 of ENU-mutagenized mice showed an increased proportion of peripheral blood $CD4^+$ and $CD8^+$ T cells. Other abnormalities included a low B:T cell ratio, and a low NK cell count. This phenotype was named chowmein and mapped to a likely damaging missense mutation in the coding sequence of the gene encoding low-density lipoprotein related receptor 10 (Lrp10), a gene encoding a member of the LDL receptor family. Similar findings were observed subsequently with other mutant alleles of the gene, and CRISPR/Cas9 targeting verified the effect with an 8 bp frameshifting deletion mutation. The ENU allele resulted in a change of aspartic acid to tyrosine at position 246 of the polypeptide chain (D246Y), within the ectodomain of the single spanning receptor protein.

To confirm cause and effect, female C57BL/6J mice were superovulated by injection with 6.5 U pregnant mare serum gonadotropin (PMSG; Millipore, #367222), then 6.5 U human chorionic gonadotropin (hCG; Sigma-Aldrich, #C1063) 48 hours later. The superovulated mice were subsequently mated with C57BL/6J male mice overnight. The following day, fertilized eggs were collected from the oviducts and in vitro transcribed Cas9 mRNA (50 ng/µl) and Lrp10 small base-pairing guide RNA (50 ng/µl; 5'-ACAGCCCTGGACTGAGTA-3') were injected into the cytoplasm or pronucleus of the embryos. The PCR primers were:

```
(Forward)
                                       (SEQ ID NO: 71)
AGTCCCCCAGGAAGAGGCAA (Reverse)
                                       (SEQ ID NO: 72)
TCACCTAGGTTCTCACTAGCCCC GT
```

The sequencing primer was tgggagttctggcacttccctg. The injected embryos were cultured in M16 medium (Sigma-Aldrich, #M7292) at 37° C. and 95% air/5% CO2. For the production of mutant mice, 2-cell stage embryos were transferred into the ampulla of the oviduct (10-20 embryos per oviduct) of pseudopregnant Hsd:ICR (CD-1) (Harlan Laboratories, #030) females. The founder $Lrp10^{-/-}$ mice have a 8-bp deletion in the fifth exon (CCTGGACTTGAG(TACGGAG)ATGCAGTGCA) (SEQ ID NO: 73) with 8-bp deletion denoted in parenthesis), resulting in a frameshift predicted to cause premature termination after 117 amino acids compared to the 713 amino acid wild type LRP10 protein. The CRISPR Lrp10 KO strain was subjected to the FACS screen and recapitulated the increased peripheral $CD4^+$ and $CD8^+$ T cells observed in chowmein.

Bone Marrow Chimeras

Recipient mice were given a 6 Gy exposure by X-ray irradiator twice at a 5-hour interval. Antibiotic water was provided to the recipients after irradiation.

Figure 2:
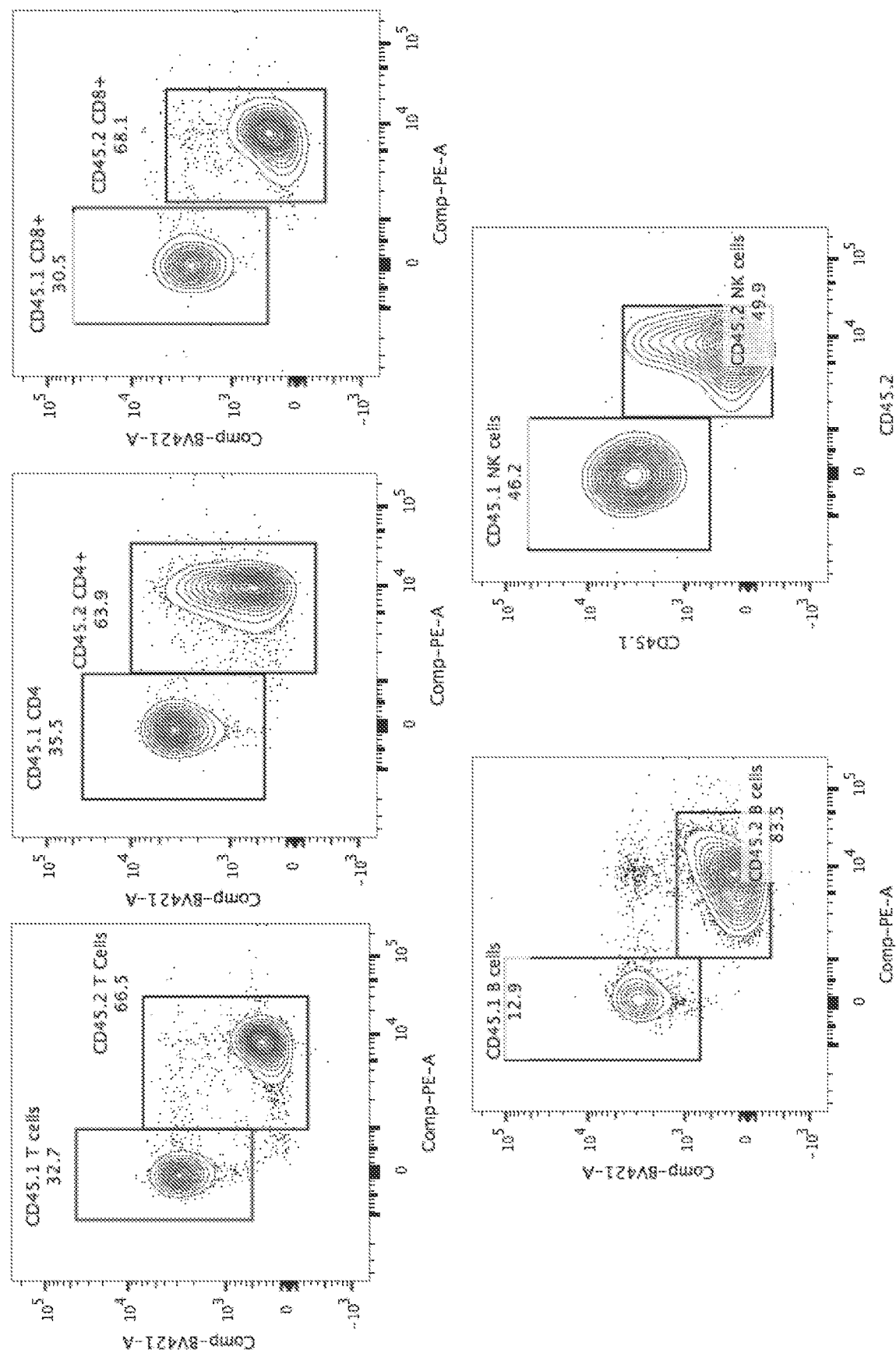
FIG. 2 shows flow cytometry results of T cells, CD4+ cells, CD8+ cells, B cells, and NK cells in peripheral blood from donor chimeras (1:1 mixture of CD45.1 and CD45.2) in irradiated Rag2$^{-/-}$ mice post-transplantation.
Figure 3:
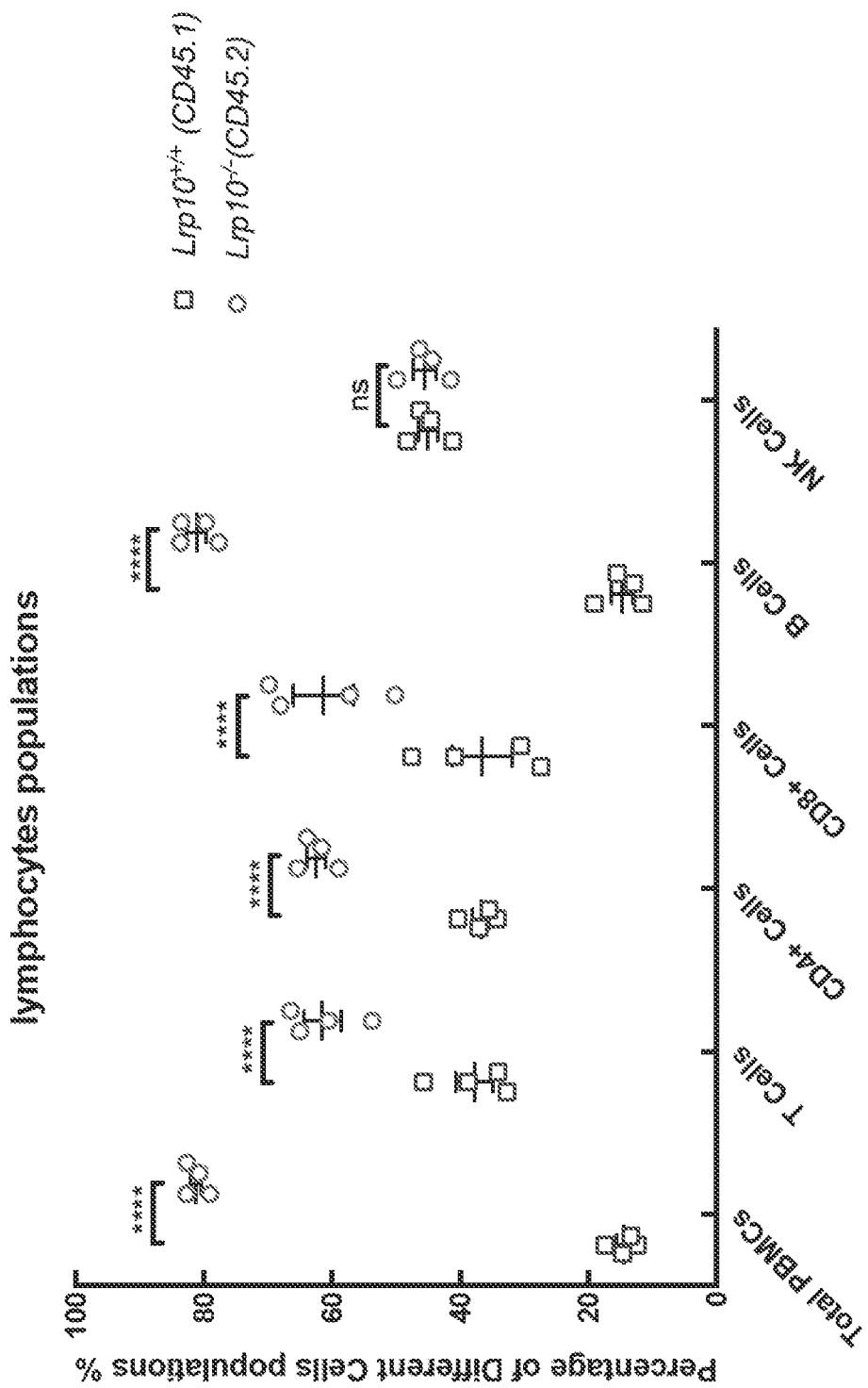
FIG. 3 shows the percentage of different lymphocytes populations (T cells, CD4+ cells, CD8+ cells, B cells, and NK cells) in peripheral blood from donor chimeras (1:1 mixture of CD45.1 and CD45.2) in irradiated Rag2$^{-/-}$ mice post-transplantation, suggesting that chowmein homozygotes display an increase in the competitive potential of hematopoietic stem cells.
Figure 4:
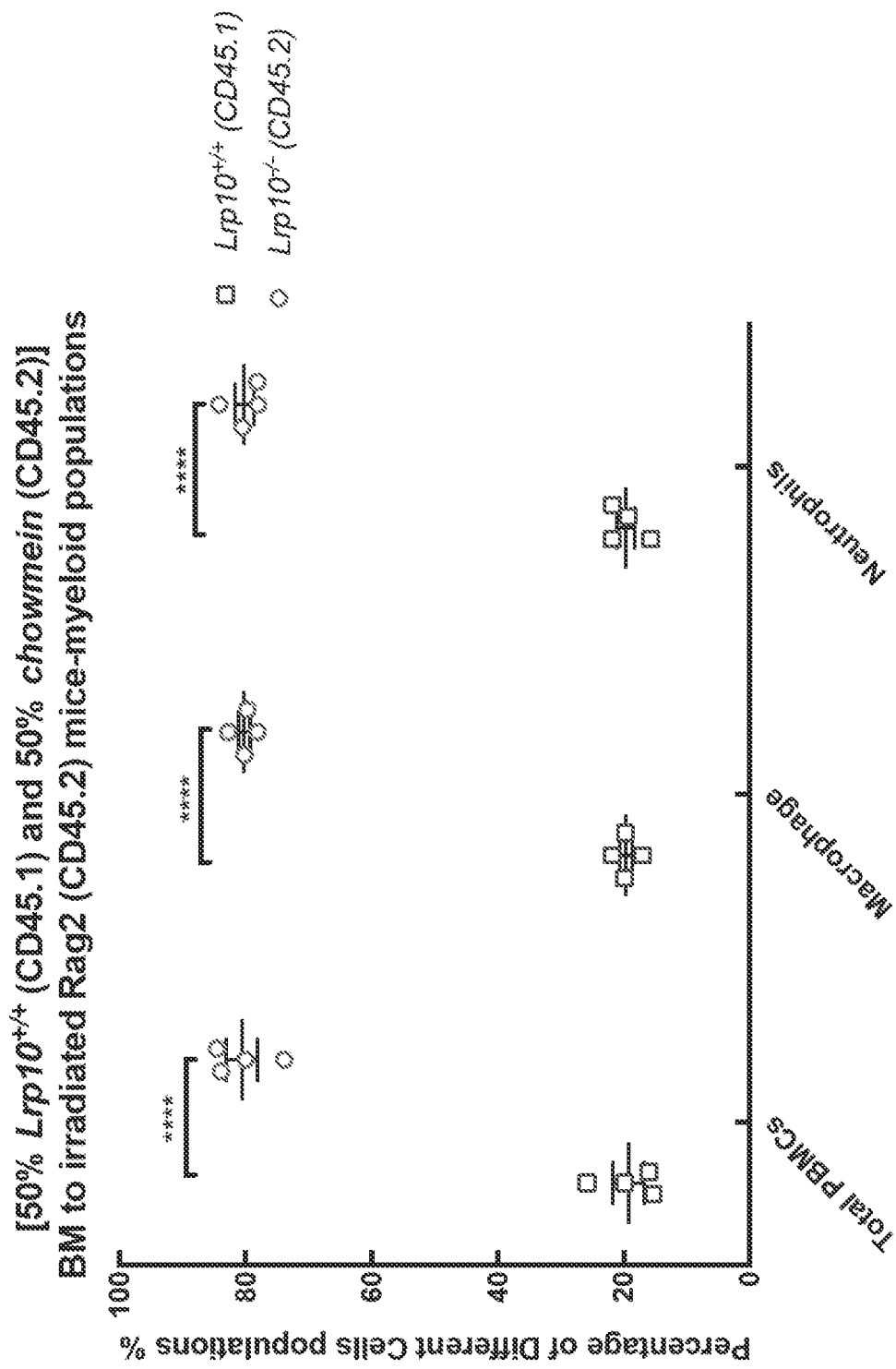
FIG. 4 shows the percentage of different myeloid populations (macrophages and neutrophils cells) in peripheral blood from donor chimeras (1:1 mixture of CD45.1 and CD45.2) in irradiated Rag2$^{-/-}$ mice post-transplantation, suggesting that chowmein homozygotes display an increase in the competitive potential of hematopoietic stem cells.

Femurs from donor C57BL/6 mice (CD45.1), CRISPR-Lrp10 KO (CD45.2) homozygotes were placed in a small dish (on ice) containing medium [RPMI-1640 medium (Life Technologies, #72400-120) supplemented with 10% (v/v) FBS (Life Technologies, #10082-147), 10 units/ml penicillin, and streptomycin (Life Technologies, #15140-122). The femurs were flushed with this medium using a 25 G needle. To remove bits of bone, the marrow was homogenized and the solution was put through a sterile 40-µm nylon cell strainer (BD Biosciences, #352340) and collected in a 50-ml tube. The volume was brought to 50 ml with medium and then centrifuged at 700×g for 5 min at 4° C. The cells were then resuspended in 5 ml of red blood cell lysing buffer (Sigma-Aldrich, #R7757) and incubated for 1 to 2 min. 5 ml of sterile PBS was added to the tube, and 10 µl cells and 10 µl Trypan Blue were mixed to count the total number of cells. Next, the cells were centrifuged at 700×g for 5 min, and the cells were then resuspended in 1 ml PBS and transferred into 1.5 ml Eppendorf tubes and kept on ice. Bone marrow cells from C57BL/6 mice (CD45.1), CRISPR-Lrp10 KO mice (CD45.2), or a 1:1 mixture were transferred into the indicated recipient mice through retro-orbital injection (FIG. 1). Peripheral blood was sampled at time points post-transplantation and the fraction of donor chimeras within the major immune cell populations was assessed with flow cytometry using fluorescence-conjugated antibodies against the CD45 congenic markers (CD45.1 Biolegend, #110732, CD45.2 Biolegend, #109814) and CD3ε (BD Horizon, #553062), CD4 (BD Horizon, #562464), CD8a (Biolegend, #100752), B220 (BD Pharmingen, #557957), CD19 (BD Bioscience, #563557), CD11b (Biolegend, #101237), and NK 1.1 (Biolegend, #564143). Overall, in each experiment, it was observed that mutant cells from the CRISPR-Lrp10 KO mice (CD45.2) significantly outgrew the wild-type C57BL/6 mice (CD45.1) cells, which suggested a much stronger proliferative activity (FIG. 2, FIG. 3, and FIG. 4).

T Cell and HSC Migration Assay

Figure 5:
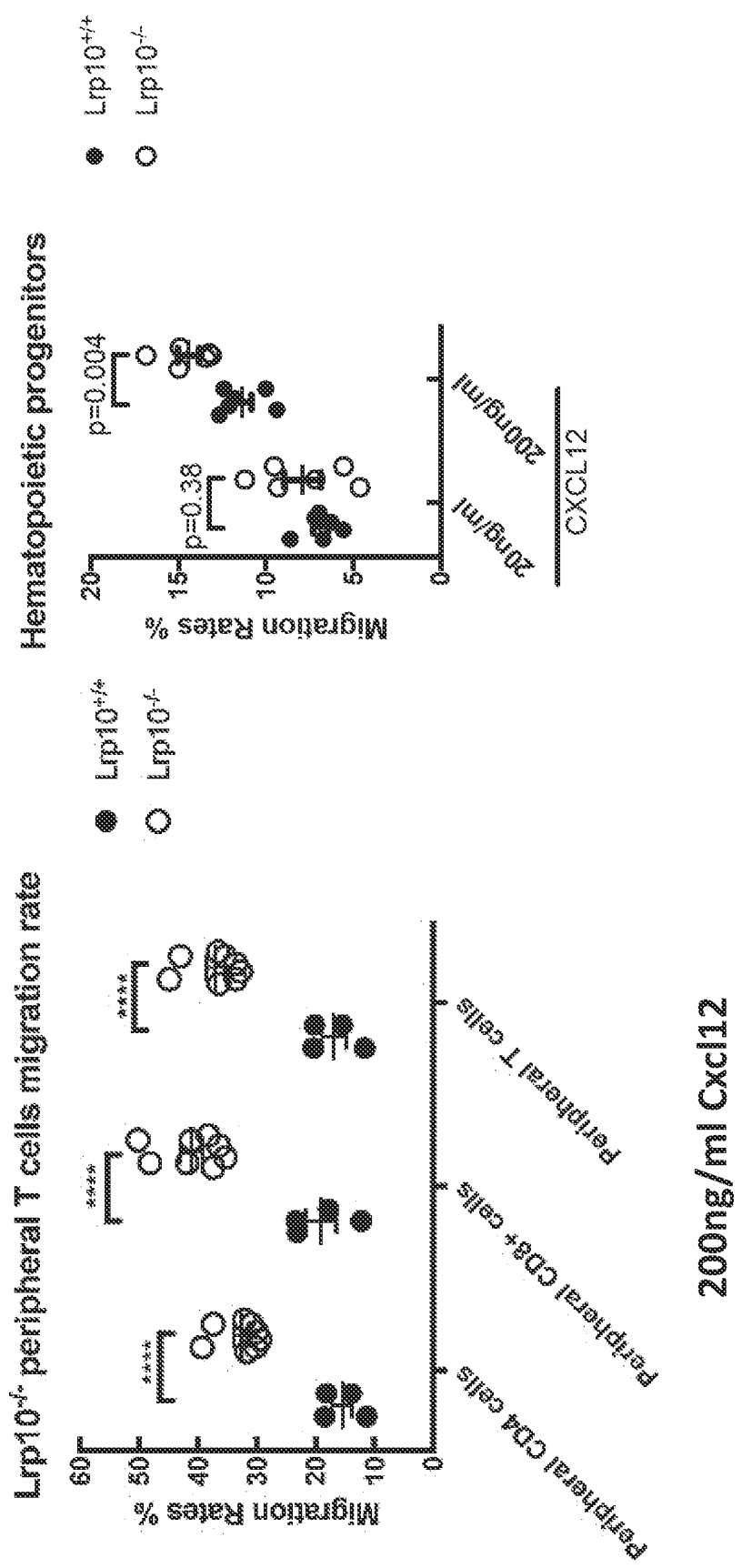
FIG. 5 shows that Lrp10$^{-/-}$ peripheral T lymphocytes (clear circles) migrate at a higher rate than Lrp10$^{+/+}$ (dark circles) in a chemotaxis assay.

Using the CRISPR knockout mice, homozygous mutant T cells were examined for migratory activity in response to stimulation with C-X-C motif chemokine 12 (CXCL12) (FIG. 5). To perform this experiment, total T cells were isolated from the spleens and lymph nodes of C57BL/6 mice and CRISPR-Lrp10 KO homozygotes using a negative selection kit (StemCell Technologies, #19851). Hematopoietic stem cells (HSCs) were then isolated from the bone marrow of these mice using an HSC enrichment kit (StemCell Technologies, #19756). Next, 10 μl of cells and 10 μl of Trypan Blue were mixed together to count the total number of cells. Cells were then resuspended in RPMI containing (w/v) 1% BSA at a density of $10^7$/ml. 100 μl of this suspension ($10^6$ cells) was added to the upper chamber of a 24-well Transwell plate containing 5-micron polycarbonate membrane inserts (Corning, #CLS3421-48EA). 600 μl of RPMI/(w/v) 1% BSA containing 0, 20, or 200 ng/ml of stromal cell-derived factor 1 (SDF-1) (Peprotech, #250-20A), also known as CXCL12, was added to the lower chamber. The Transwell plates were incubated at 37 degrees for 3.5 hours. After incubation, the upper chamber was discarded and the cells that had migrated to the lower chamber were stained with fluorescence-conjugated antibodies to CD4 (BD Horizon, #562464) and CD8a (Biolegend, #100752). Cell counts were assessed by measuring the total events collected in 30 s on an LSR Fortessa. The percentage of migrating cells was calculated by dividing the number of events collected at each chemokine concentration by the number of events collected in 30 s from a 1:6 dilution of the input cell population. Overall, the mutant cells from the CRISPR-Lrp10 KO mice showed greatly enhanced migration toward the CXCL12 chemokine stimulus compared to the wild-type C57BL/6 mouse cells (FIG. 5).

Figure 6:
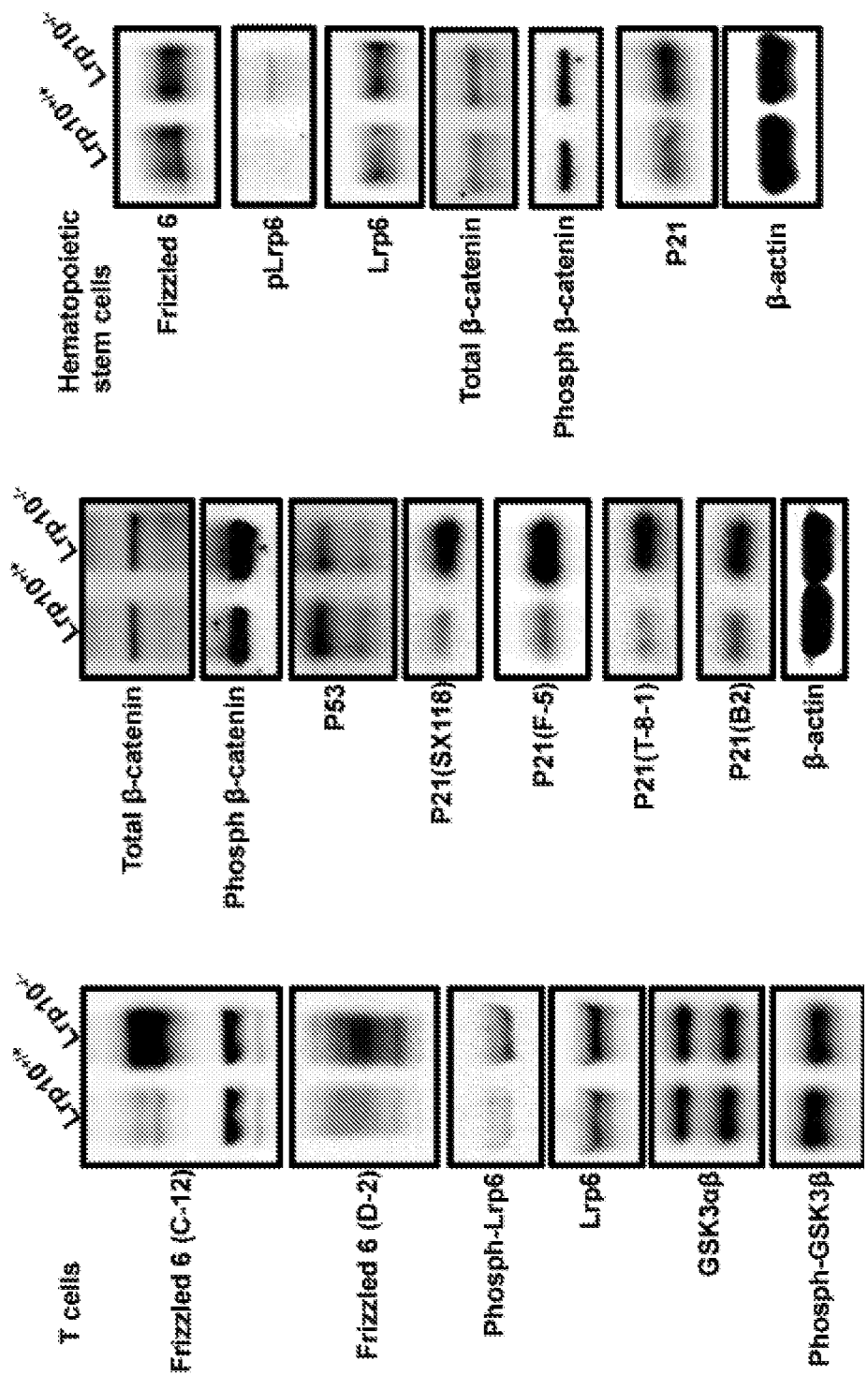
FIG. 6 shows significantly increased expression of Frizzled and P21 in Lrp10$^{-/-}$ T cells and hematopoietic progenitors than Lrp10$^{+/+}$ cells.

Western Blot Assays for p21 and Frizzled-6:

Wnt signaling pathways play fundamental roles in the differentiation, proliferation and functions of many cells as well as developmental, growth, and homeostatic processes in animals. Low-density lipoprotein receptor (LDLR)-related protein (LRP) 5 and LRP6 are co-receptors of Wnt proteins together with Frizzled receptors, triggering activation of canonical Wnt/beta-catenin signaling. To understand how LRP10 regulates Wnt/β-catenin signaling, T cells and HSCs were enriched as described above. Unstimulated cells (~$10^6$) were then lysed in buffer containing 1% SDS (ThermoFisher, #AM9820), 1:10,000 Benzonase (Sigma, #E1014), and 1:100 Protease Inhibitor Cocktail (Cell Signaling Technology, #5871S) in buffer A (50 mM HEPES, 2 mM $MgCl_2$, 10 mM KCl). Protein concentration was measured using the BCA assay (Pierce). The cell extracts (20 μl each; equivalent to ~$1\times10^6$ cells) were separated on NuPAGE™ Novex™ 4-12% Bis-Tris protein gels (Life Technologies, #NP0336BOX) and proteins were transferred to nitrocellulose membranes (Bio-Rad, #162-0115) for 1 hour at 12 voltage. After blocking in Tris-buffered saline containing 0.05% (v/v) Tween-20 (TBS-T) with 5% (w/v) BSA at room temperature for 2 hours, the membrane was incubated overnight with primary antibody anti-P21 (Santa Cruz Bio Tech, #SC-6246), anti-Frizzled (Santa Cruz Bio Tech, #SC-393113), and anti-βActin (Cell Signaling, #3700S) at 4° C. in 5% (w/v) BSA in TBS-T with gentle rocking. The membrane was then incubated with secondary antibody goat anti-mouse IgM-HRP (Southern Biotech, #1021-05), goat anti-rabbit IgG-HRP (Thermo fisher, #A16096), or goat anti-rabbit IgG-HRP (Thermo fisher, #A16096) for 1 hour at room temperature. The Chemiluminescence signal was developed by using SuperSignal West Dura Extended Duration Substrate kit (Fisher Scientific, #PIA34075) and detected by a G:Box Chemi XX6 system (Syngene). As shown in FIG. 6, the $Lrp10^{-/-}$ T cells and the $Lrp10^{-/-}$ hematopoietic cells have higher expression of p21, which is an end product of Wnt signaling. Also, both the $Lrp10^{-/-}$ T cells and the $Lrp10^{-/-}$ hematopoietic cells express the transmembrane spanning receptor, Fizzled 6. Together, this data demonstrates that the increase competitive potential of $Lrp10^{-/-}$ T cells and $Lrp10^{-/-}$ hematopoietic cells is dependent on a non-canonical Wnt/β-catenin signaling pathway.

Flow Cytometry:

Peripheral blood cells were isolated, and red blood cell (RBC) lysis buffer was added to remove the RBCs. Cells were stained at a 1:200 dilution with 15 mouse fluorochrome-conjugated monoclonal antibodies specific for the following murine cell surface markers encompassing the major immune lineages: B220, CD19, IgM, IgD, CD3ε, CD4, CD5, CD11c, CD44, CD43, CD25, CD21, CD23, BP-1 (BD Pharmingen), CD8a, CD11b, NK1.1 (Biolegend), F4/80, CD62L (Tonbo Biosciences) and in the presence of anti-mouse CD16/32 antibody (Tonbo Biosciences) for 1 h at 4° C. After staining, cells were washed twice in PBS and analyzed by flow cytometry.

Figure 7:
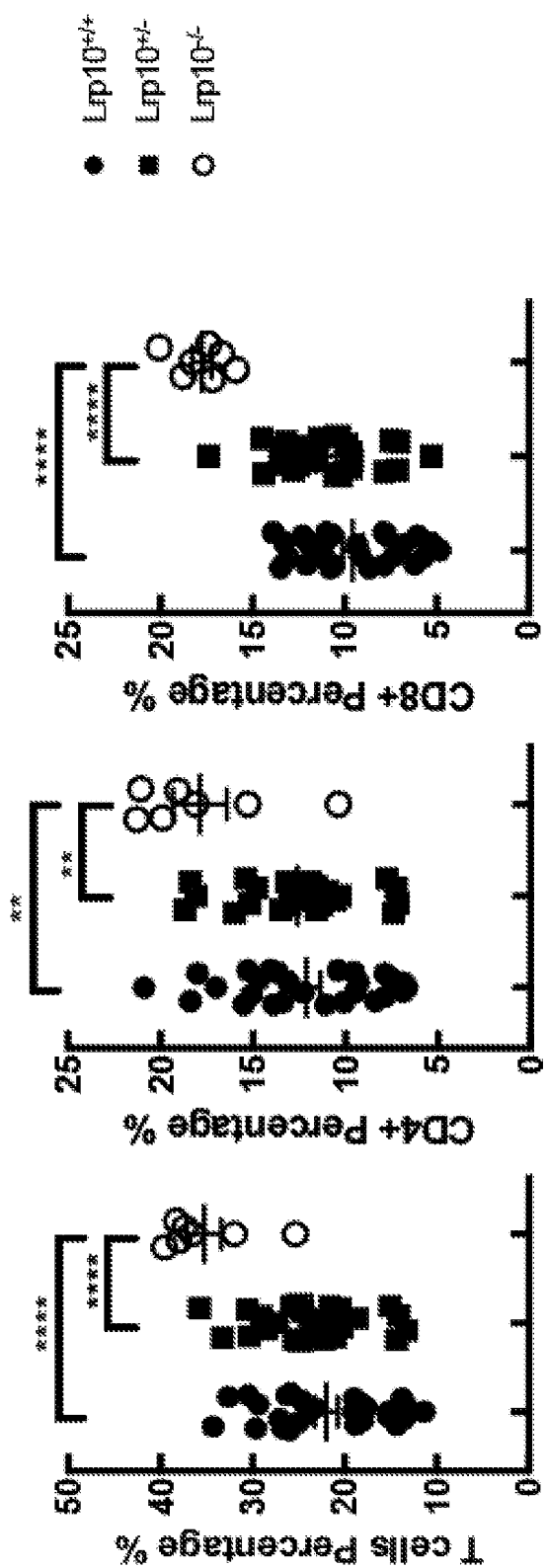
FIG. 7 shows that Lrp10$^{-/-}$ homozygotes showed higher proportion of CD4 and CD8 T cells.

As shown in FIG. 7, a point mutation in the extracellular domain of Lrp10 (D246Y) was created during ENU mutagenesis. Mice homozygous for this mutation showed an increased proportion of CD3+, CD4+, and CD8+ T cells in their peripheral blood and were named chowmein ($Lrp10^{ch/ch}$). This mutation had a recessive mode of inheritance as heterozygotes ($Lrp10^{+/ch}$) and wild-type mice ($Lrp10^{+/+}$) were not affected.

Tumor Inoculation. Anti-PD-1 Treatment and Tumor Measurement:

B16F10 melanoma cells were grown in DMEM containing 10% vol/vol FBS. A total of $2\times10^5$ B16F10 cells in 100 μL DPBS were injected s.c. into the right flank of C57BL/6J mice, wild type, heterozygous and homozygous LRP10 CRISPR KO mice to establish tumors. For anti-PD-1 treatment, 300 μg anti-PD-1 in 200 μL DPBS was injected i.p. into mice on day 5, 8 and 11 after tumor inoculation. Tumors were measured with a digital caliper (Fisher), and the tumor sizes were calculated using the following formula: volume=0.5×length×width$^2$. Mice were killed when the tumor length or width reached 2 cm.

Figure 8:
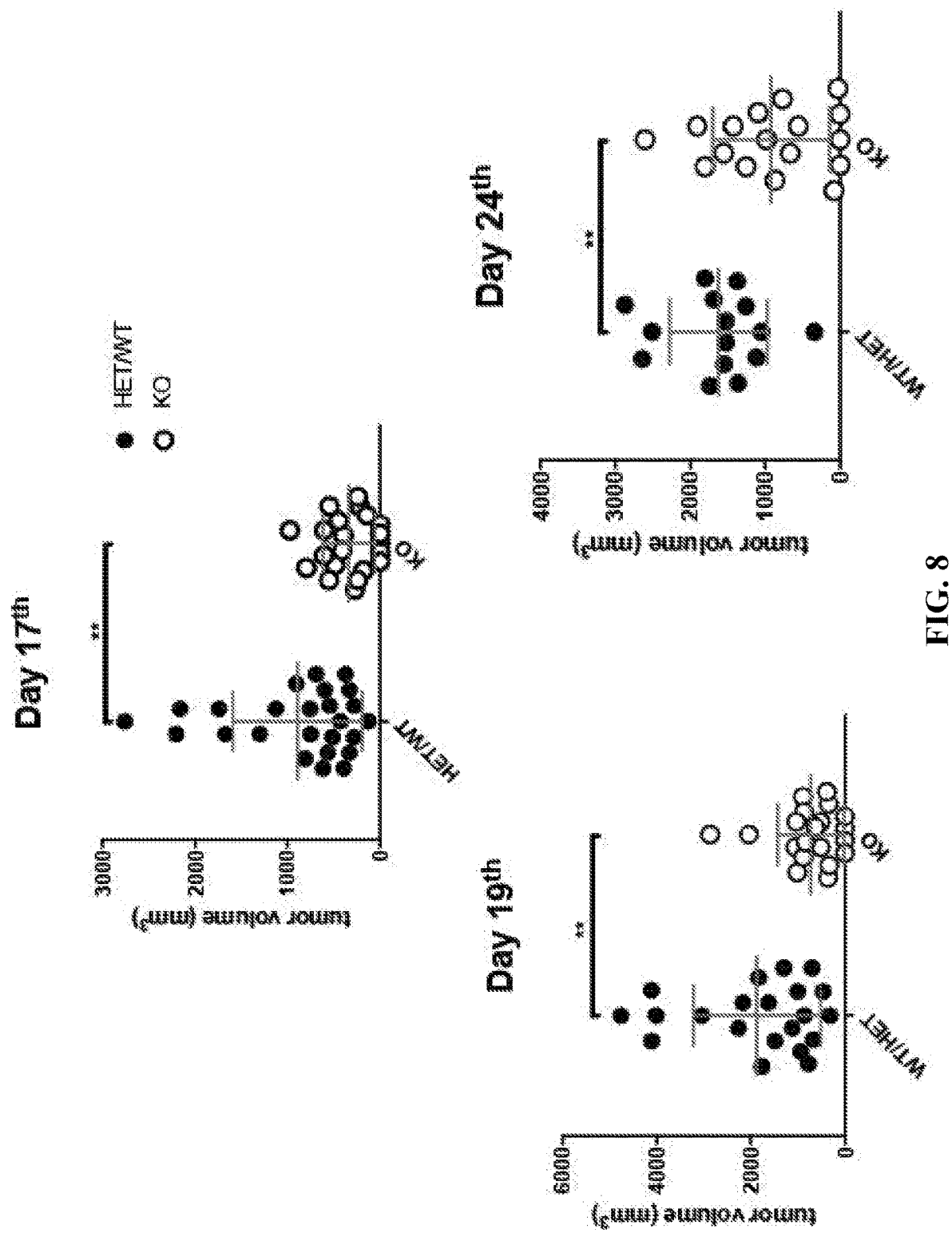
FIG. 8 shows that melanoma growth is retarded or arrested in mice lacking Lrp10.

As shown in FIG. 8, Lrp10 knockout mice ($Lrp10^{-/-}$) were made using CRISPR-Cas9. $Lrp10^{+/+}$ and $Lrp10^{-/-}$ mice were injected subcutaneously with the syngeneic B16 melanoma tumor cell line. 7 days after tumor cell injection, mice were given an intraperitoneal injection with anti-PD1 for checkpoint blockade. Tumor volume was measured on days 17, 19, and 24 post-tumor injection. $Lrp10^{-/-}$ showed significantly lower average tumor volume at these time points.

Figure 9:
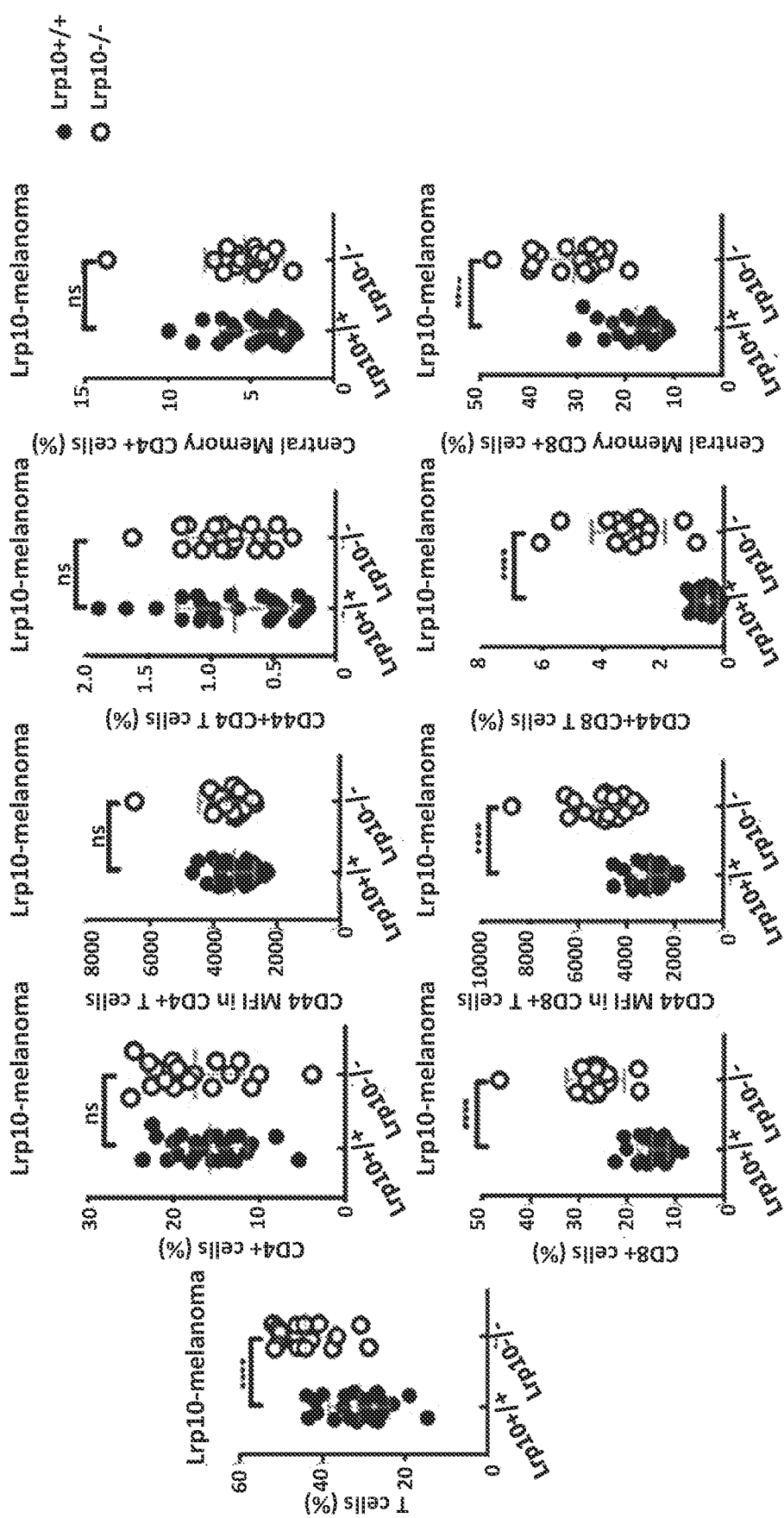
FIG. 9 shows that Lrp10$^{-/-}$ homozygotes challenged with melanoma B16 cells showed higher active CD8+ T cells in the blood.

As shown in FIG. 9, on day 19 post-tumor injection, peripheral blood was harvested from B16-bearing Lrp10$^{+/+}$ and Lrp10$^{-/-}$ mice. Tumor-bearing Lrp10$^{-/-}$ mice had a higher proportion of total T cells in the peripheral blood. In contrast to tumor naïve Lrp10$^{-/-}$, only CD8+ T cells were elevated in tumor-bearing Lrp10$^{-/-}$ mice and these had an activated effector phenotype as measured by CD44 expression.

Example 2: Generation of LRP10 Monoclonal Antibody

Based on analysis of the NCBI *Mus musculus* (www.ncbi.nlm.nih.gov/gene/65107) LRP10, it was determined that two fragments (XP_006519421.1 and NP_075369.2) from *Mus musculus* LRP10 were predicted as alternatively spliced transcripts from Lrp10 EST libraries. Also, based on analysis of *Homo sapiens* (www.ncbi.nlm.nih.gov/gene/26020) LRP10 (also known as LRP9 in *Homo sapiens*), it was determined that three fragments (NP_001316155.1, NP_054764.2, XP_005267567) from *Homo sapiens* LRP10 were predicted as alternatively spliced transcripts from Lrp10 EST libraries. Both human NP_054764.2 and murine NP_075369.2, as canonical LRP10 proteins, are 713-residue long with 17-residue signal peptides, as analyzed by SignalP 4.1 (www.cbs.dtu.dk/services/SignalP/). Human LRP10 protein has 88% identity to the murine LRP10 protein. Three *Homo sapiens* LRP10 protein variants, including the 516-, 713-, or 721-residue variants, were aligned by ClustalW. Comparing to the canonical protein, two isoforms lack residues 135-143, and human LRP10 isoform2 lacks the last 157 residues. Canonical human LRP10 protein has an ectodomain consisting of the first 440 residues, a transmembrane domain consisting of residues 441-463, and an intracellular domain consisting of residues 464-713. In order to target all the isoforms of human LRP10 protein, isoform2 was analyzed by Lasergene/Protean. Based on this analysis, residues $159^{th}$-$192^{th}$, $294^{th}$-$360^{th}$, and $378^{th}$-$434^{th}$ polypeptides are candidates for the anti-human Lrp10 antibodies.

The amino-acid sequence of the first 420 amino acids of the protein, which can be expressed for use as an immunogen, is as follows:

```
>sp|Q7Z4F1|LRP10_HUMAN Low-density lipoprotein
receptor-related protein 10
OS = Homo sapiens GN = LRP10 PE = 1 SV = 2
                                       (SEQ ID NO: 74)
MLLATLLLLLLGGALAHPDRIIFPNHACEDPPAVLLEVQGTLQRPLVRDS

RTSPANCTWLILGSKEQTVTIRFQKLHLACGSERLTLRSPLQPLISLCEA

PPSPLQLPGGNVTITYSYAGARAPMGQGFLLSYSQDWLMCLQEEFQCLNH

RCVSAVQRCDGVDACGDGSDEAGCSSDPFPGLTPRPVPSLPCNVTLEDFY

GVFSSPGYTHLASVSHPQSCHWLLDPHDGRRLAVRFTALDLGFGDAVHVY

DGPGPPESSRLLRSLTHFSNGKAVTVETLSGQAVVSYHTVAWSNGRGFNA

TYHVRGYCLPWDRPCGLGSGLGAGEGLGERCYSEAQRCDGSWDCADGTDE

EDCPGCPPGHFPCGAAGTSGATACYLPADRCNYQTFCADGADERRCRHCQ

PGNFRCRDEKCVYETWVCDGQPDCADGSDEWDCSYVLPRK
```

A portion of the above ectodomain, as opposed to the full length, can also be used as an immunogen. Different methods known in the art, and those that have been disclosed herein, may be used to generate fully human or humanized anti-LRP10 antibodies. For example, as described above, fully human LRP10 antibodies can also be produced from phage-display libraries. Humanized anti-LRP10 antibodies can be prepared by humanizing monoclonal antibodies obtained from hybridomas.

For example, a C-terminal His tag, suitable for purification by affinity chromatography, can be added to the immunogen. Purified protein can be inoculated into mice together with a suitable adjuvant. Monoclonal antibodies produced in hybridomas can be tested for binding to the immunogen, and positive binders can be screened for ability to neutralize T cell migration or to affect Frizzled and/or p21 expression in human lymphoid cells in the assays described above. Thereafter, antibodies can be humanized for preclinical and clinical studies.

Biopanning and Screening:

A typical biopanning includes 3-5 rounds to achieve an acceptable enrichment.

1. Library Biopanning
    1) Coat each well of an ELISA plate with 2 μg target of interest in 50 μL Coating Buffer (0.1 M NaHCO$_3$, pH 9.6) and incubate overnight at 4° C. Discard the coating solution and wash the wells with washing buffer of 0.1% PBST [PBS with 0.1% (v/v) Tween 20] for 3 times and block the wells by adding 300 μL Blocking Buffer [2% PBSM (PBS containing 2% skim milk)]. Seal and incubate overnight at 4° C.
    2) Discard the Blocking Buffer and add 50-100 μL phage library (~$10^{11}$ phage particles) to each well (4 wells). Seal and incubate for 2 h at 37° C.
    3) Remove the spent phage solution. Wash the coated surface 9 times using an ELISA plate washer machine
    4) After removing the final washing solution, add 200 μL Elution Buffer, incubate for 10 min at 37° C. Pipet vigorously up and down for 10 times. Transfer the eluate to a microfuge tube containing 100 μL Neutralizing Buffer.
2. Phage Titration
    1) Make serial dilutions of phages in 2×YT Medium (For the phage input, expect titers of $10^{12-13}$ phage/mL. Make dilutions between $10^{-8}$ and $10^{-10}$. For the phage output, make dilutions between $10^{-1}$ and $10^{-4}$ for Round 1, while make dilutions between $10^{-2}$ and $10^{-6}$ for Round 2 and 3).
    2) Add 500 μL log phase *E. coli* TG1s (OD600≈0.5) (30 min 37° C.).
    3) Plate out 100 μL infected cells onto 2×YT agar containing 2% glucose and 100 μg/mL ampicillin and grow at 37° C. O/N.
3. Rescue of the Selected Phages
    1) Infect *E. coli* TG1 with eluted phage output by adding the total output to 6 mL TG1 (OD$_{600}$≈0.5).
    2) Allow infection to incubate in 37° C. water bath for 30 min.
    3) Add 9 mL 2×YT-AG Medium. Grow overnight at 37° C.
    4) Centrifuge at 5,000 rpm for 15 min at 4° C. Resuspend the pellet in 2×YT Medium containing 15% glycerol and store at −80° C. Master stock to be rescued for future selections.
4. Phage Amplification for Next Round of Biopanning
    1) Inoculate part of the rescued glycerol stock into 25 mL 2×YT-AG Medium.
    2) Grow to exponential phase (OD$_{600}$≈0.5) by shaking at 37° C.
    3) Add ~2×$10^{11}$ pfu M13KO7 Helper Phage.

4) Allow infection to incubate in 37° C. water bath for 30 min.
5) Centrifuge at 5,000 rpm for 15 min.
6) Resuspend the pellet in 25 mL 2×YT-AK Medium.
7) Transfer to a 250 mL flask. Grow shaking (225 rpm) overnight at 30° C.

5. Phage Purification for Next Round of Biopanning
    1) Spin the culture in a 50 mL centrifuge tube at 4,000 g for 20 min to pellet the bacteria.
    2) To the supernatant, add ⅕$^{th}$ of the volume of 5×PEG/NaCl and leave on ice for at least 1 h.
    3) Pellet phages by spinning at 12,000 g for 15 min at 4° C.
    4) Discard the supernatant.
    5) Resuspend the pellet in 1 mL sterile PBS.
    6) Transfer to a 1.5 mL microcentrifuge tube.
    7) Spin in microcentrifuge (2 min, maximum g) to remove the remaining bacteria.
    8) Transfer supernatant to a new tube. The phages are now ready for use in the further screening rounds or selection assays. Phage can be stored at 4° C. without much decrease in titer. For long-term storage, add glycerol to 20% and store at −80° C.

Antibody Expression and Purification:
1. The cDNAs of light chain and heavy chain of the antibody were chemically synthesized with optimization for mammalian expression. The cDNAs were cloned in the expression vector.
2. The encoding genes of light chain and heavy chain were co-transfected with 30 mL 293F cells. The supernatant was harvested on day 6 after transfection.
3. The antibodies were purified by affinity chromatography using immobilized protein A.
    1) Transfer 1 ml of Protein A pure resin to a new disposable plastic gravity flow column. Wash the resin with 10 column volumes (CVs) of ultrapure water, and then equilibrate with 10 CVs of TBS, pH 7.5/8.0 buffer.
    2) Apply the filtered antibody supernatant to the column and allow it to flow through by gravity. Wash the resin twice with 10 CVs of PBS. Collect the flow-throughs from both the supernatant and the washes, and keep them on ice or at 4° C. for further analysis.
    3) For elution of bound antibody, add 4 ml of glycine-HCl elution buffer (pH 2.7) and collect the flow-through into tubes prefilled with 1 ml of Tris-HCl solution (pH 7.6). Collect additional fractions as above. Stop elution when the OD280 nm of the fractions is zero (this is usually after three to five fractions).
    4) After elution, subject the resin to sequential washes with 10 CVs of glycine-HCl (pH 2.7), 10 CVs of PBS, 10 CVs of ultrapure water and 10 CVs of 20% (vol/vol) ethanol. Store the resin in 20% (vol/vol) ethanol at 4° C. for future use.
    5) Analyze all fractions by SDS-PAGE.
    6) Combine the fractions with visible protein bands and dialyze against ≥30 volumes of low-endotoxin PBS buffer for at least 2 h at 4° C. using dialysis tubing.
    7) Concentrate the dialyzed protein using a centrifugal concentrator (≤10 kDa cut-off) prewashed with PBS.
    8) Filter the concentrated sample through a syringe-driven 0.22-μm filter and calculate the protein concentration by BCA method.

ELISA Test:
1) Coat the target protein LR10 (1 μg/ml, 0.1 μg/well) in a certain coating buffer (0.1 M NaHCO$_3$, pH 9.6). Incubate overnight at 4° C.
2) Wash the wells 3 times with 300 μL washing buffer (0.1% PBST) per well.
3) Block the wells with 300 μL blocking buffer (3% BSA) for 1 h at 37° C.
4) Discard the blocking buffer and wash the plate 3 times with the washing buffer, slapping the plate face-down onto a clean section of paper towel each time.
5) Add 100 μL of a serial dilution of antibodies per well. Incubate at 37° C. for 1 h.
6) Wash 3 times with the washing buffer. Dilute HRP-goat anti-human IgG (1:4,000) in the blocking buffer (3% BSA). Add 100 μL of diluted conjugate per well and incubate at 37° C. for 1 h.
7) Wash 3 times with the washing buffer. Dissolve Tetramethylbenzidine (TMB) substrate (Sigma, USA) in 0.1 mmol/L citrate-phosphate buffer and add 1 μL/mL H$_2$O$_2$ to the solution. Add 100 μL of substrate solution per well and incubate at room temperature for 15 minutes.
8) Add 100 μL of 2 mol/L H$_2$SO$_4$ solution to stop the reaction.
9) Read plates using a microplate reader set at 490 nm.

Results:
The Phage Display HuScl-2™ Library from Creative Biolabs Inc. was used for 3 rounds of biopinning. His-tagged recombinant human LRP10 protein, LRP10-516H was used as antigen. Sequencing of the sublibrary from the 3$^{rd}$ round of biopanning identified 9 unique clones having the following VL and VH sequences (both amino acid and nucleotide sequences). Note that for the full antibody sequence, each VL can be linked to alight chain constant region such as Ck (SEQ ID NO: 31) to form a full light chain, and each VH can be linked to a heavy chain constant region such as human IgG1 CH123 (SEQ ID NO: 32) to form a full heavy chain.

---

Clone 1 (AB1)

```
Protein sequence
VL (SEQ ID NO: 1):
TDIQMTQSPSSLSASVGDRVTITCRASQSISSYLNWYQQKPGKAPKLLIYNASDLQ
SGVPSRFSGSGSGTDFTLTISSLQPEDFATYYCQQSSRTPTTFGQGTKVEIK VH (SEQ ID NO: 2):
MAEVQLLESGGGLVQPGGSLRLSCAASGFTFSSQAMSWVRQAPGKGLEWVSSIPP
GGPNTKYADSVKGRFTISRDNSKNTLYLQMNSLRAEDTAVYYCAKSYPSFDYWG
QGTLVTVSS Nucleotide sequence
VL (SEQ ID NO: 3):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATAATGCATCC
GATTTGCAAAGTGGGGTCCCATCAAGGTTCAGTGGCAGTGGATCTGGGACAG
```

```
ATTTCACTCTCACCATCAGCAGTCTGCAACCTGAAGATTTTGCAACTTACTACT
GTCAACAGTCGTCGCGGACGCCTACGACGTTCGGCCAAGGGACCAAGGTGGA
AATCAAA

VH (SEQ ID NO: 4):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTAGGCC
ATGAGCTGGGTCCGCCAGGCTCCAGGGAAGGGGCTGGAGTGGGTCTCATCTA
TTCCTCCGGGTGGTCCTAATACAAAGTACGCAGACTCCGTGAAGGGCCGGTTC
ACCATCTCCAGAGACAATTCCAAGAACACGCTGTATCTGCAAATGAACAGCCT
GAGAGCCGAGGACACGGCCGTATATTACTGTGCGAAAAGTTATCCTTCTTTTG
ACTACTGGGGCCAGGGAACCCTGGTCACCGTCTCGAGC
```

Clone 2 (AB2)

```
Protein sequence
VL (SEQ ID NO: 5):
TDIQMTQSPSSLSASVGDRVTITCRASQSISSYLNWYQQKPGKAPKLLIYAASPLQS
GVPSRFSGSGSGTDFTLTISSLQPEDFATYYCQQVARTPNTFGQGTKVEIK VH (SEQ ID NO: 2):
MAEVQLLESGGGLVQPGGSLRLSCAASGFTFSSQAMSWVRQAPGKGLEWVSSIPP
GGPNTKYADSVKGRFTISRDNSKNTLYLQMNSLRAEDTAVYYCAKSYPSFDYWG
QGTLVTVSS Nucleotide sequence
VL (SEQ ID NO: 6):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATGCGGCATC
CCCGTTGCAAAGTGGGGTCCCATCAAGGTTCAGTGGCAGTGGATCTGGGACA
GATTTCACTCTCACCATCAGCAGTCTGCAACCTGAAGATTTTGCAACTTACTAC
TGTCAACAGGTGGCTCGTACGCCTAATACGTTCGGCCAAGGGACCAAGGTGG
AAATCAAA VH (SEQ ID NO: 4):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTAGGCC
ATGAGCTGGGTCCGCCAGGCTCCAGGGAAGGGGCTGGAGTGGGTCTCATCTA
TTCCTCCGGGTGGTCCTAATACAAAGTACGCAGACTCCGTGAAGGGCCGGTTC
ACCATCTCCAGAGACAATTCCAAGAACACGCTGTATCTGCAAATGAACAGCCT
GAGAGCCGAGGACACGGCCGTATATTACTGTGCGAAAAGTTATCCTTCTTTTG
ACTACTGGGGCCAGGGAACCCTGGTCACCGTCTCGAGC
```

Clone 3 (AB3)

```
Protein sequence
VL (SEQ ID NO: 7):
TDIQMTQSPSSLSASVGDRVTITCRASQSISSYLNWYQQKPGKAPKLLIYRASRLQ
SGVPSRFSGSGSGTDFTLTISSLQPEDFATYYCQQPTSLPLTFGQGTKVEIK VH (SEQ ID NO: 8):
MAEVQLLESGGGLVQPGGSLRLSCAASGFTFSSYAMSWVRQAPGKGLEWVSQIG
TMGRPTTYADSVKGRFTISRDNSKNTLYLQMNSLRAEDTAVYYCAKSGKKFDY
WGQGTLVTVSS Nucleotide sequence
VL (SEQ ID NO: 9):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATAGGGCATC
CCGTTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGCCGACTTCGTTGCCTCTGACGTTCGGCCAAGGGACCAAGGTGGAA
ATCAAA VH (SEQ ID NO: 10):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCATAGAT
TGGGACGATGGGTCGGCCGACAACTTACGCAGACTCCGTGAAGGCCGGTTC
ACCATCTCCAGAGACAATTCCAAGAACACGCTGTATCTGCAAATGAACAGCCT
GAGAGCCGAGGACACGGCCGTATATTACTGTGCGAAAAGTGGGAAGAAGTTT
GACTACTGGGGCCAGGGAACCCTGGTCACCGTCTCGAGC
```

Clone 4 (AB4)

Protein sequence
VL (SEQ ID NO: 11):
TDIQMTQSPSSLSASVGDRVTITCRASQSISSYLNWYQQKPGKAPKLLIYAASALQ
SGVPSRFSGSGSGTDFTLTISSLQPEDFATYYCQQADSYPTTFGQGTKVEIK VH (SEQ ID NO: 12):
MAEVQLLESGGGLVQPGGSLRLSCAASGFTFSSYAMSWVRLAPGKGLEWVSSIST
TGNSTYYADSVKGRFTISRDNSKNTLYLQMNSLRAEDTAVYYCAKDATSFDYWG
QGTLVTVSS Nucleotide sequence
VL (SEQ ID NO: 13):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATGCTGCATCC
GCTTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGGCTGATTCTTATCCTACTACGTTCGGCCAAGGGACCAAGGTGGAA
ATCAAA VH (SEQ ID NO: 14):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCTGGCTCAGGGAAGGGGCTGGAGTGGGTCTCATCTATT
TCTACTACTGGTAATAGTACATATTACGCAGACTCCGTGAAGGGCCGGTTCAC
CATCTCCAGAGACAATTCCAAGAACACGCTGTATCTGCAAATGAACAGCCTGA
GAGCCGAGGACACGGCCGTATATTACTGTGCGAAAGATGCTACTAGTTTTGAC
TACTGGGGCCAGGGAACCCTGGTCACCGTCTCGAGC

Clone 5 (AB5)

Protein sequence
VL (SEQ ID NO: 15):
TDIQMTQSPSSLSASVGDRVTITCRASQSISSYLNWYQQKPGKAPKLLIYRASRLQ
SGVPSRFSGSGSGTDFTLTISSLQPEDFATYYCQQIKTRPTTFGQGTKVEIK VH (SEQ ID NO: 16):
MAEVQLLESGGGLVQPGGSLRLSCAASGFTFSSYAMSWVRQAPGKGLEWVSVIQ
RQGTGTEYADSVKGRFTISRDNSKNTLYLQMNSLRAEDTAVYYCAKNSRTFDYW
GQGTLVTVSS Nucleotide sequence
VL (SEQ ID NO: 17):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATCGTGCATCC
CGTTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGATTAAGACAAGGCCTACGACGTTCGGCCAAGGGACCAAGGTGGA
AATCAAA VH (SEQ ID NO: 18):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCAGTTATT
CAGCGTTAGGGTACTGGTACAGAGTACGCAGACTCCGTGAAGGGCCGGTTCA
CCATCTCCAGAGACAATTCCAAGAACACGCTGTATCTGCAAATGAACAGCCTG
AGAGCCGAGGACACGGCCGTATATTACTGTGCAAAAAATTCGCGGACGTTTG
ACTACTGGGGCCAGGGAACCCTGGTCACCGTCTCGAGC

Clone 6 (AB6)

Protein sequence
VL (SEQ ID NO: 19):
TDIQMTQSPSSLSASVGDRVTITCRASQSISSYLNWYQQKPGKAPKLLIYDASLLQ
SGVPSRFSGSGSGTDFTLTISSLQPEDFATYYCQQTSAGPGTFGQGTKVEIK VH (SEQ ID NO: 20):
MAEVQLLESGGGLVQPGGSLRLSCAASGFTFSSYAMSWVRQAPGKGLEWVSSIPS
RGQATKYADSVKGRFTISRDNSKNTLYLQMNSLRAEDTAVYYCAKSRHTFDYW
GQGTLVTVSS Nucleotide sequence
VL (SEQ ID NO: 21):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT

```
GGTATCAGCAGAAACCAGGGAAAGCCCCTAAGCTCCTGATCTATGATGCATCC
CTTTTGCAAAGTGGGGTCCCATCAAGGTTCAGTGGCAGTGGATCTGGGACAGA
TTTCACTCTCACCATCAGCAGTCTGCAACCTGAAGATTTTGCAACTTACTACTG
TCAACAGACTTCTGCGGGTCCTGGTACGTTCGGCCAAGGGACCAAGGTGGAA
ATCAAA

VH (SEQ ID NO: 22):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCAGGCTCAGGGAAGGGGCTGGAGTGGGTCTCAAGTAT
TCCTAGTCGTGGTTAGGCAACAAAGTACGCAGACTCCGTGAAGGGCCGGTTCA
CCATCTCCAGAGACAATTCCAAGAACACGCTGTATCTGCAAATGAACAGCCTG
AGAGCCGAGGACACGGCCGTATATTACTGCGCGAAATCGCGTCATACTTTTGA
CTACTGGGGCCAGGGAACCCTGGTCACCGTCTCGAGC
```

Clone 7 (AB7)

Protein sequence
VL (SEQ ID NO: 23):
TDIQMTQSPSSLSASVGDRVTITCRASQSISSYLNWYQQKPGKAPKLLIYAASTLQ
SGVPSRFSGSGSGTDFTLTISSLQPEDFATYYCQQNDYYPTTFGQGTKVEIK VH (SEQ ID NO: 24):
MAEVQLLESGGGLVQPGGSLRLSCAASGFTFSSYAMSWVRQAPGKGLEWVSSIA
TTGNTTYYADSVKGRFTISRDNSKNTLYLQMNSLRAEDTAVYYCAKNTATFDYW
GQGTLVTVSS Nucleotide sequence
VL (SEQ ID NO: 25):
```
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATGCTGCATCC
ACTTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGAATGATTATTATCCTACTACGTTCGGCCAAGGGACCAAGGTGGAA
ATCAAA VH (SEQ ID NO: 26):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCAGGCTCAGGGAAGGGGCTGGAGTGGGTCTCATCTATT
GCTACTACTGGTAATACTACATATTACGCAGACTCCGTGAAGGGCCGGTTCAC
CATCTCCAGAGACAATTCCAAGAACACGCTGTATCTGCAAATGAACAGCCTGA
GAGCCGAGGACACGGCCGTATATTACTGTGCGAAAAATACTGCTACTTTTGAC
TACTGGGGCCAGGGAACCCTGGTCACCGTCTCGAGC
```

Clone 8 (AB8)

Protein sequence
VL (SEQ ID NO: 1):
TDIQMTQSPSSLSASVGDRVTITCRASQSISSYLNWYQQKPGKAPKLLIYNASDLQ
SGVPSRFSGSGSGTDFTLTISSLQPEDFATYYCQQSSRTPTTFGQGTKVEIK VH (SEQ ID NO: 27):
MAEVQLLESGGGLVQLGGSLRLSCAASGFTFSSQAMSWVRQAPGKGLEWVSSIP
PGGPNTKYADSVKGRFTISRDNSKNTLYLQMNSLRAEDTAVYYCAKSYPSFDYW
GQGTLVTVSS Nucleotide sequence
VL (SEQ ID NO: 3):
```
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATAATGCATCC
GATTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGTCGTCGCGGACGCCTACGACGTTCGGCCAAGGGACCAAGGTGGA
AATCAAA VH (SEQ ID NO: 28):
ATGGCCGAGGTGCAGCTGTTGGAGTCTGGGGGAGGCTTGGTACAGCTTGGGG
GGTCCCTGAGACTCTCCTGTGCAGCCTCTGGATTCACCTTTAGCAGCTAGGCC
ATGAGCTGGGTCCGCCAGGCTCCAGGGAAGGGGCTGGAGTGGGTCTCATCTA
TTCCTCCGGGTGGTCCTAATACAAAGTACGCAGACTCCGTGAAGGGCCGGTTC
ACCATCTCCAGAGACAATTCCAAGAACACGCTGTATCTGCAAATGAACAGCCT
GAGAGCCGAGGACACGGCCGTATATTACTGTGCGAAAAGTTATCCTTCTTTTG
ACTACTGGGGCCAGGGAACCCTGGTCACCGTCTCGAGC
```

-continued

---
Clone 9 (AB9)
---

Figure 10:
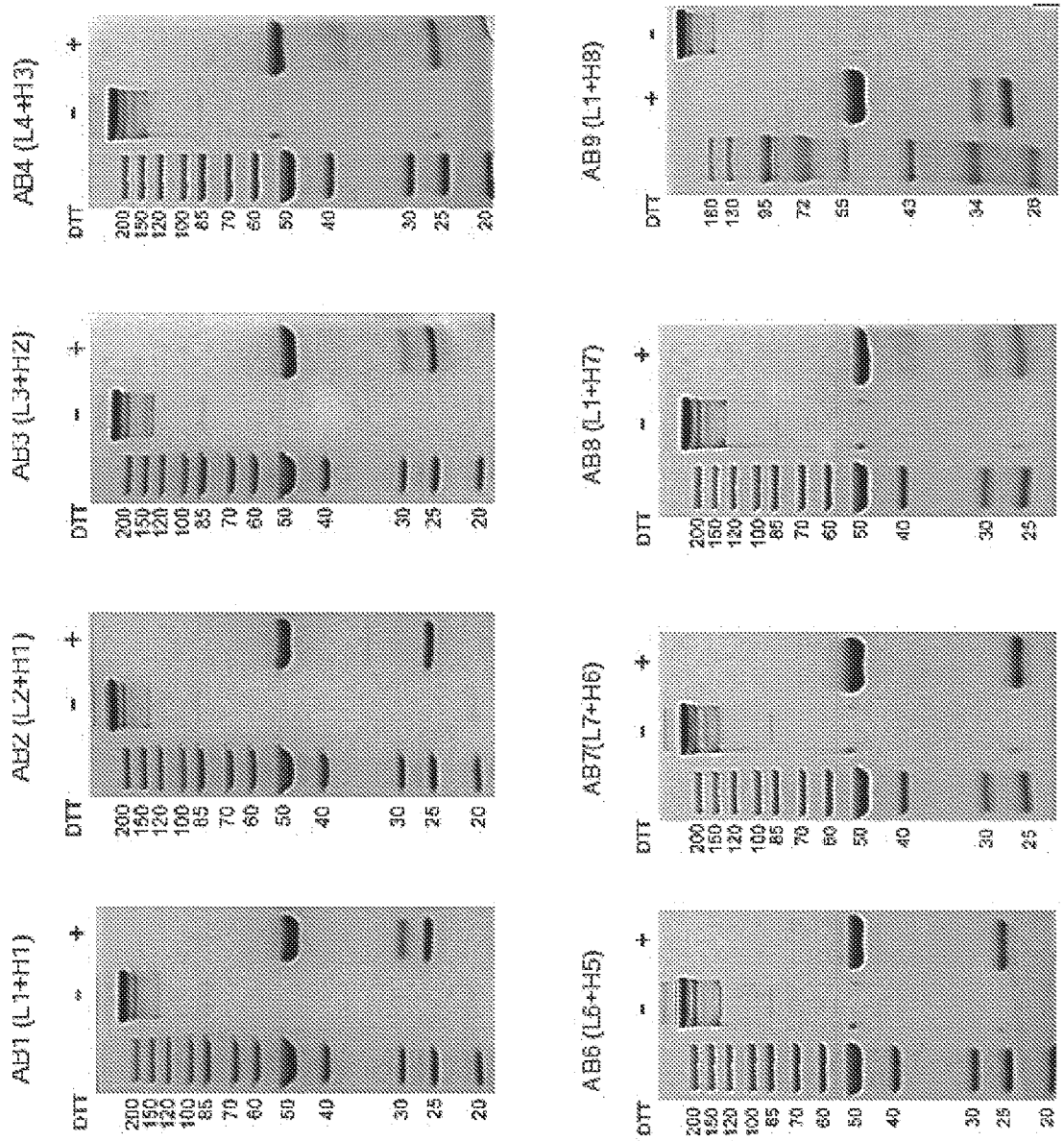
FIG. 10 shows expression and purification of 9 antibodies.

Protein sequence
VL (SEQ ID NO: 1):
TDIQMTQSPSSLSASVGDRVTITCRASQSISSYLNWYQQKPGKAPKLLIYNASDLQ
SGVPSRFSGSGSGTDFTLTISSLQPEDFATYYCQQSSRTPTTFGQGTKVEIK VH (SEQ ID NO: 29):
MAEVQLLESGGGLVQPGGSLRLSCAASGFTFSSYAMSWVRQAPGKGLEWVSSIY
TSGAATTYADSVKGRFTISRDNSKNTLYLQMNSLRAEDTAVYYCAKSYPSFDYW
GQGTLVTVSS Nucleotide sequence
VL (SEQ ID NO: 3):
ACGGACATCCAGATGACCCAGTCTCCATCCTCCCTGTCTGCATCTGTAGGAGA
CAGAGTCACCATCACTTGCCGGGCAAGTCAGAGCATTAGCAGCTATTTAAATT
GGTATCAGCAGAAACCAGGGAAAGCCCCTAAGCTCCTGATCTATAATGCATCC
GATTTGCAAAGTGGGGTCCCATCAAGGTTCAGTGGCAGTGGATCTGGGACAG
ATTTCACTCTCACCATCAGCAGTCTGCAACCTGAAGATTTTGCAACTTACTACT
GTCAACAGTCGTCGCGGACGCCTACGACGTTCGGCCAAGGGACCAAGGTGGA
AATCAAA VH (SEQ ID NO: 30):
ATGGCCGAGGTGCAGCTGTTGGAGTCTGGGGGAGGCTTGGTACAGCCTGGGG
GGTCCCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCATCTATT
TATACTTCTGGTGCTGCTACAACTTACGCAGACTCCGTGAAGGGCCGGTTCAC
CATCTCCAGAGACAATTCCAAGAACACGCTGTATCTGCAAATGAACAGCCTGA
GAGCCGAGGACACGGCCGTATATTACTGTGCGAAAAGTTATCCTTCTTTTGAC
TACTGGGGCCAGGGAACCCTGGTCACCGTCTCGAGC Ck amino acid sequence (SEQ ID NO: 31):
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC IgG1 CH123 amino acid sequence (SEQ ID NO: 32):
ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK We chemically synthesized the cDNAs of these antibodies for mammalian cell expression. The genes of light chain and heavy chain were cloned into the expression vector, respectively, and co-transfected into 293F cells. We first used an 80 mL culture for each clone for the antibody expression test. As shown in FIG. 10, 8 antibodies were expressed successfully, while the expression of AB5 was too low to be detected. After purification by Protein A-based affinity chromatography, all 8 antibodies achieved high purity.

For clone AB5, we also tried the CHO expression system but its expression level was still quite low. This indicates that the poor expressability of this clone is due to the antibody sequence itself.

Figure 11:
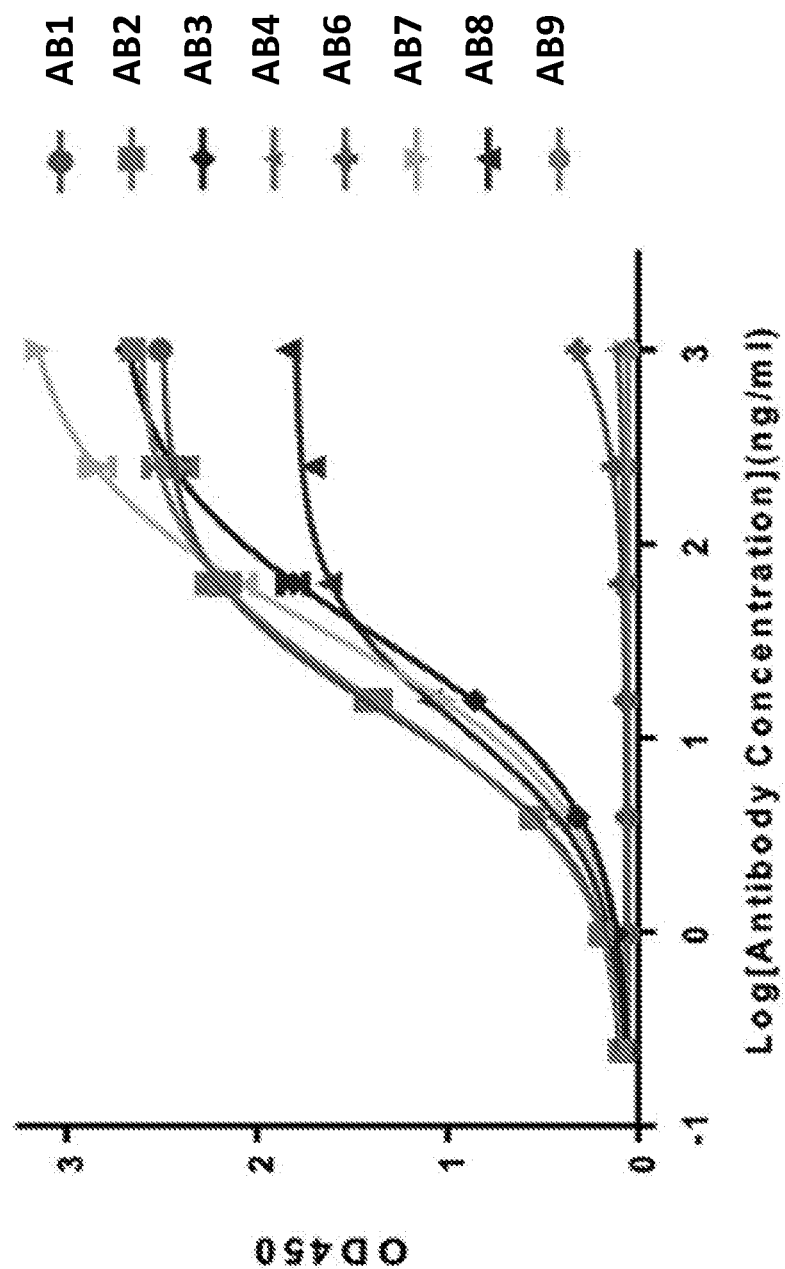
FIG. 11 shows ELISA (enzyme-linked immunosorbent assay) results of antibody binding to LRP10.

For the 8 well-expressed antibodies, we tested their binding activities to the target antigen by ELISA (Table 7 and FIG. 11). Among the 8 clones, 5[AB1 (L1+H1), AB2 (L2+H1), AB3 (L3+H2), AB7(L7+H6), and AB8 (L1+H7)] of them showed high affinity to the antigen, whereas the other 3 antibodies did not exhibit binding activities.

For the 5 high-affinity antibodies, AB1 and AB2 showed the best binding activity, which was consistent with the sequencing results that these two sequences had the highest frequencies.

TABLE 7

| ELISA results | | | | | | | | |
|---|---|---|---|---|---|---|---|---|
| Con. (ng/ml) | AB1 (L1 + H1) | | AB2 (L2 + H1) | | AB3 (L3 + H2) | | AB4 (L4 + H3) | |
| 1000 | 2.4919 | 2.5264 | 2.6404 | 2.6633 | 2.6678 | 2.6894 | 0.1135 | 0.108 |
| 250 | 2.4027 | 2.3947 | 2.3273 | 2.5826 | 2.4178 | 2.4264 | 0.0754 | 0.0744 |
| 62.5 | 2.1695 | 2.2884 | 2.1059 | 2.3035 | 1.878 | 1.7456 | 0.0768 | 0.0789 |
| 15.63 | 1.3403 | 1.4688 | 1.3149 | 1.4561 | 0.8578 | 0.8585 | 0.0612 | 0.0662 |
| 3.91 | 0.527 | 0.5902 | 0.5337 | 0.5752 | 0.318 | 0.3198 | 0.0591 | 0.0582 |
| 0.98 | 0.1853 | 0.1948 | 0.1855 | 0.2099 | 0.1201 | 0.1158 | 0.057 | 0.0598 |
| 0.24 | 0.0871 | 0.0916 | 0.0904 | 0.0906 | 0.0625 | 0.0596 | 0.0533 | 0.0578 |
| 0 | 0.0508 | 0.0592 | 0.0592 | 0.0697 | 0.0393 | 0.0575 | 0.0609 | 0.0664 |
| EC50 | 12.97 | | 14.78 | | 34.87 | | | |

TABLE 7-continued

ELISA results

| Con. (ng/ml) | AB6 (L6 + H5) | | AB7 (L7 + H6) | | AB (L1 + H7) | | AB9 (L1 + H8) | |
|---|---|---|---|---|---|---|---|---|
| 1000 | 0.2887 | 0.3495 | 3.1821 | 3.1195 | 1.872 | 1.8043 | 0.0561 | 0.052 |
| 250 | 0.1284 | 0.1332 | 2.7589 | 2.915 | 1.7051 | 1.7107 | 0.0665 | 0.0619 |
| 62.5 | 0.09 | 0.0989 | 2.168 | 2.0191 | 1.6008 | 1.6468 | 0.066 | 0.0548 |
| 15.63 | 0.0659 | 0.0656 | 0.9558 | 1.072 | 1.0632 | 1.1305 | 0.0619 | 0.0519 |
| 3.91 | 0.0615 | 0.0582 | 0.3916 | 0.3886 | 0.3891 | 0.4484 | 0.0523 | 0.0586 |
| 0.98 | 0.0588 | 0.0556 | 0.1293 | 0.0523 | 0.1585 | 0.1749 | 0.057 | 0.0464 |
| 0.24 | 0.0606 | 0.0573 | 0.0723 | 0.0801 | 0.0851 | 0.0859 | 0.0619 | 0.053 |
| 0 | 0.0595 | 0.0594 | 0.073 | 0.0579 | 0.0546 | 0.0515 | 0.0512 | 0.0452 |
| EC50 | | | 35.68 | | 11.71 | | | |

Example 3. Functional Test of Monoclonal Antibodies

Western Blot

The expression of P21 was examined for the blocking of Lrp10 functions by human antibodies. For direct Western blot analysis in purified splenic pan T cells isolated using a negative selection method (StemCell Technologies, #19851) were cultured with or without 100 ug/ml human anti-Lrp10 antibodies AB1, AB2, AB3, AB4, AB6, AB7, AB8, or AB9 for 4 h, and lysed in buffer (1% (w/v) SDS (Thermo), 0.01% (w/v) Benzonase (Sigma), protease inhibitor cocktail (Cell Signaling Technology) in buffer A (50 mM HEPES, 2 mM MgCl2, 10 mM KCl). Protein concentration was measured using a BCA assay (Pierce). Ten micrograms of protein were separated on 4-12% Bris-Tris protein gels (Life Technologies) and proteins were transferred to nitrocellulose membranes (Bio-Rad) for 45 minutes at 13 volts. After blocking in Tris-buffered saline containing 0.05% (v/v) Tween-20 (TBS-T) with 5% (w/v) non-fat dry milk (NFDM) at room temperature for 1 hour, the membrane was incubated overnight with primary antibodies anti-P21 (Santa Cruz) and anti-PActin (Cell Signaling Technology), at 4° C. in 5% (w/v) BSA in TBS-T with gentle rocking. The membrane was then incubated with secondary antibody goat anti-rabbit or mouse IgG-HRP (Thermo fisher) for 1 hour at room temperature with gentle rocking. The chemiluminescence signal was developed by using SuperSignal West Dura Extended Duration Substrate kit (Thermo Fisher) and detected by a G:Box Chemi XX6 system (Syngene). Overall, AB2 showed greatly enhanced P21 expression in wild-type C57BL/6 mouse cells.

Figure 12:
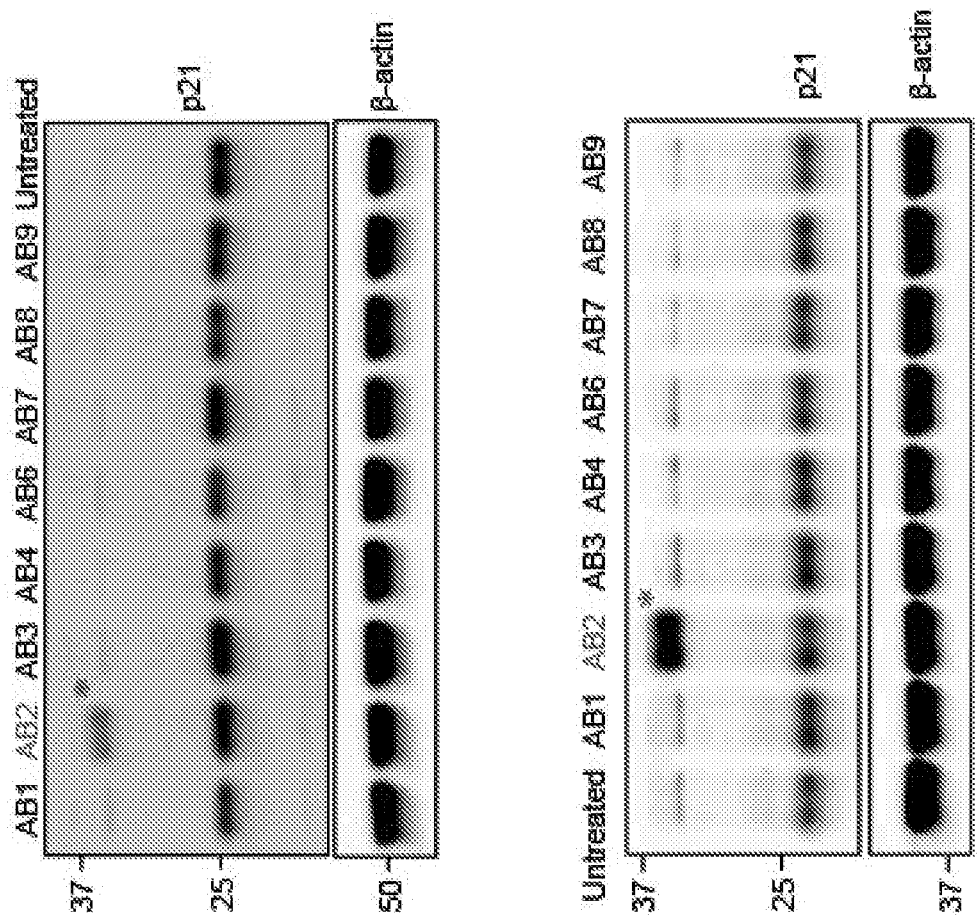
FIG. 12 shows that human anti-Lrp10 monoclonal antibody can activate p21 in mouse T cells.

We had previously observed that T cells purified from Lrp10$^{-/-}$ mice had increased expression of the cell cycle inhibitor p21 compared to Lrp10$^{+/+}$ T cells. T cells were purified from the spleens of Lrp10$^{+/+}$ mice and incubated with different anti-human Lrp10 clones. P21 expression levels were measured with Western blot. As shown in FIG. 12, here was no difference in p21 expression between untreated T cells and T cells treated with anti-Lrp10 antibodies. T cells treated with antibody 2 showed an intense immunoreactive band at ~35 kD which may reflect induction of a post-translational modification (e.g. glycosylation or sumoylation). The left and right panel show two separate experiments.

T Cells Migration Assay

Using the C57BL/6 T cells were examined for migratory activity in response to stimulation with C-X-C motif chemokine 12 (CXCL12). To perform this experiment, total T cells were isolated from the spleens and lymph nodes of C57BL/6 mice using a negative selection kit (StemCell Technologies, #19851). Next, 10 μl of cells and 10 μl of Trypan Blue were mixed together to count the total number of cells. Cells were then resuspended in RPMI containing (w/v) 1% BSA at a density of 10$^7$/ml. 100 μl of this suspension (10 cells) was pre-treated with or without 50 ug/ml Lrp10 antibody for half hours, and then cells were added to the upper chamber of a 24-well Transwell plate containing 5-micron polycarbonate membrane inserts (Corning, #CLS3421-48EA). 600 μl of RPMI/(w/v) 1% BSA containing 200 ng/ml of stromal cell-derived factor 1 (SDF-1) (Peprotech, #250-20A), also known as CXCL12, with or without 50 ug/ml Lrp10 antibody, was added to the lower chamber. The Transwell plates were incubated at 37 degrees for 3.5 hours. After incubation, the upper chamber was discarded and the cells that had migrated to the lower chamber were assessed by measuring the total events collected in 60 s on an LSR Fortessa. The percentage of migrating cells was calculated by dividing the number of events collected at each chemokine concentration by the number of events collected in 60 s from a 1:6 dilution of the input cell population. Overall, AB2 and AB7 showed greatly enhanced migration toward the CXCL12 chemokine stimulus in wild-type C57BL/6 mouse cells.

The statistical significance of differences between groups was analyzed using GraphPad by performing the indicated statistical tests. Differences in the raw values among groups were considered statistically significant when P<0.05. P values are denoted by * P<0.05;  P<0.01; * P<0.001; ns, not significant with P>0.05.

Figure 13:
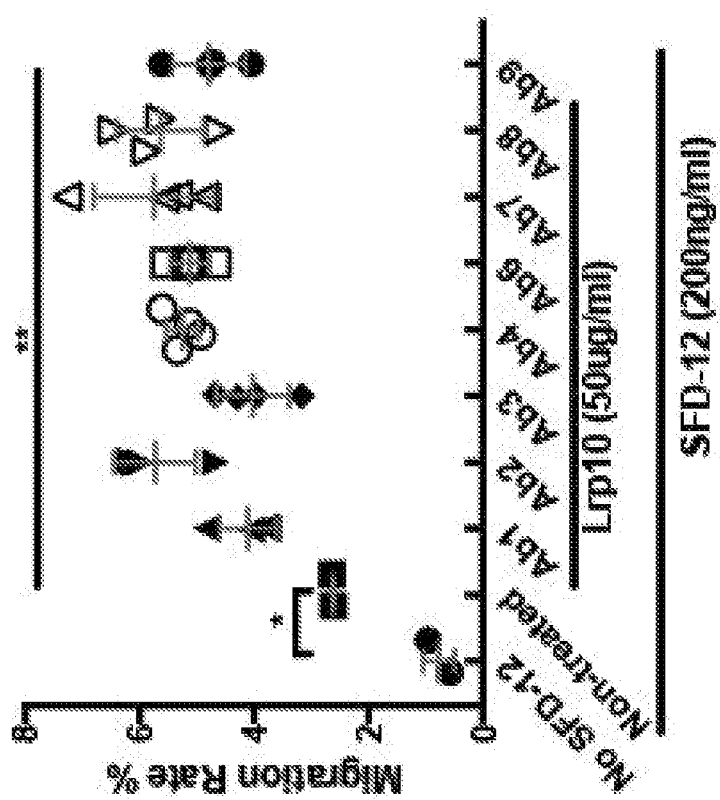
FIG. 13 shows that both AB2 and AB7 enhance T cell migration in response to SDF12.

We had observed previously that Lrp10$^{-/-}$ T cells showed an increased migration rate in response to SDF-1 (Cxcl12, ligand for CXCR4) in a transwell assay. Lrp10$^{+/+}$ splenocytes were incubated with different anti-Lrp10 antibody clones or with vehicle and placed in the upper well of a transwell chamber. The lower chamber contained SDF-1 at 200 ng/ml. Cell were allowed to migrate for 3.5 h. Afterward, the number of migrated T cells in the lower chamber was counted on a flow cytometer. Migration rate is presented as the number of T cells that migrated relative to the input number. As shown in FIG. 13, all anti-Lrp10 antibodies induced a higher migration rate compared to vehicle alone. Antibodies 2, 7, and 8 induced the highest migration rate, about 2 fold higher than vehicle, in response to SDF-1.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

The invention claimed is:

1. A method for cancer immunotherapy and/or hematopoietic recovery, comprising administering to a patient having cancer and/or in need of hematopoietic recovery an LRP10 competitor, wherein said LRP10 competitor comprises a soluble receptor for one or more LRP10 ligands, wherein said soluble receptor competes for binding with endogenous LRP10.

2. The method of claim 1, wherein said soluble receptor comprises an LRP10-Fc chimera.

3. The method of claim 2, wherein the soluble receptor is an LRP10-Fc chimera.

4. The method of claim 1, wherein said LRP10 competitor enhances tumor infiltration of lymphocytes, thereby providing cancer immunotherapy.

5. The method of claim 4, wherein the lymphocytes are CD8+ T cells and cytotoxic T lymphocytes.

6. The method of claim 1, wherein said LRP10 competitor enhances recovery of all hematopoietic lineages, in a patient who has received chemotherapy and/or radiotherapy.

7. The method of claim 6, wherein said LRP10 competitor enhances recovery of lymphoid lineages.

8. A method for cancer immunotherapy and/or hematopoietic recovery, comprising administering to a patient having cancer and/or in need of hematopoietic recovery an LRP10 inhibitor, wherein the LRP10 inhibitor comprises an anti-LRP10 antibody or antigen binding fragment thereof, comprising the following CDRs:

```
VL CDR1 (SEQ ID NO: 33):
RASQSISSYLN;

VL CDR2 (SEQ ID NO: 62):
X1ASX2LQS (X1 = N, A, R, D; X2 = D, P, R, A, L, T)

VL CDR3 (SEQ ID NO: 63):
QQX3X4X5X6PX7T (X3 = S, V, P, A, I, T, N; X4 = S,
A, T, D, K; X5 = R, S, T, A, Y; X6 = T, L, Y, R,
G; X7 = T, N, L, G);

VH CDR1 (SEQ ID NO: 64):
SX8AMS (X8 = Q, Y);

VH CDR2 (SEQ ID NO: 65):
X9IX10X11X12GX13X14TX15YADSVKG (X9 = S, Q, V;
X10 = P, G, S, Q, A, Y; X11 = P, T, R, S; X12 =
G, M, T, Q, R, S; X13 = P, R, N, T, Q, A; X14 =
N, P, S, G, A, T; X15 = K, T, Y, E);
and VH CDR3 (SEQ ID NO: 66):
X16X17X18X19FDY (X16 = S, D, N; X17 = Y, G, A, S,
R, T; X18 = P, K, T, R, H, A; X19 = S, K, T).
```

9. The method of claim 8, wherein the anti-LRP10 antibody or antigen binding fragment thereof of comprises VL CDR1, VL CDR2, VL CDR3, VH CDR1, VH CDR2, and VH CDR3, wherein:

```
VL CDR1 is (SEQ ID NO: 33):
RASQSISSYLN,

VL CDR2 is selected from (SEQ ID NO: 34):
NASDLQS, (SEQ ID NO: 35):
AASPLQS, (SEQ ID NO: 36):
RASRLQS, (SEQ ID NO: 37):
AASALQS, (SEQ ID NO: 38):
DASLLQS,
and (SEQ ID NO: 39):
AASTLQS, VL CDR3 is selected from (SEQ ID NO: 40):
QQSSRTPTT, (SEQ ID NO: 41):
QQVARTPNT, (SEQ ID NO: 42):
QQPTSLPLT, (SEQ ID NO: 43):
QQADSYPTT, (SEQ ID NO: 44):
QQIKTRPTT, (SEQ ID NO: 45):
QQTSAGPGT,
and (SEQ ID NO: 46):
QQNDYYPTT, VH CDR1 is selected from (SEQ ID NO: 47):
SQAMS
and (SEQ ID NO: 48):
SYAMS, VH CDR2 is selected from (SEQ ID NO: 49):
QIGTMGRPTTYADSVKG, (SEQ ID NO: 50):
SISTTGNSTYYADSVKG, (SEQ ID NO: 51):
VIQRQGTGTEYADSVKGVKG,
```

```
(SEQ ID NO: 52):
SIPSRGQATKYADSVKGVKG, (SEQ ID NO: 53):
SIATTGNTTYYADSVKG, (SEQ ID NO: 54):
SIPPGGPNTKYADSVKG,
and (SEQ ID NO: 55):
SIYTSGAATTYADSVKG, VH CDR3 is selected from (SEQ ID NO: 56):
SYPSFDY, (SEQ ID NO: 57):
SGKKFDY, (SEQ ID NO: 58):
DATSFDY, (SEQ ID NO: 59):
NSRTFDY, (SEQ ID NO: 60):
SRHTFDY,
and (SEQ ID NO: 61):
NTATFDY.
```

10. The method of claim 8, wherein the anti-LRP10 antibody or antigen binding fragment thereof of comprises a VL sequence selected from the group consisting of SEQ ID NOS: 1, 5, 7, 11, 15, 19, and 23 and a VH sequence selected from the group consisting of SEQ ID NOS: 2, 8, 12, 16, 20, 24, 27, and 29.

11. The method of claim 8, wherein the anti-LRP10 antibody or fragment thereof enhances cell migration toward a chemotactic stimulus in the patient.

12. The method of claim 11, wherein the chemotactic stimulus is selected from C-X-C motif chemokine 12 (CXCL12), C-X-C motif chemokine 10 (CXCL10), sphingosine-1-phosphate (S1P), C-C motif ligand 2 (CCL2), and/or C-C motif ligand 21 (CCL21).

13. The method of claim 8, wherein the anti-LRP10 antibody or fragment thereof increases expression of Frizzled and/or P21 on a cell in the patient.

14. The method of claim 8, wherein said anti-LRP10 antibody or antigen binding fragment thereof, enhances tumor infiltration of lymphocytes, thereby providing cancer immunotherapy.

15. The method of claim 14, wherein the lymphocytes are CD8+ T cells and cytotoxic T lymphocytes.

16. The method of claim 8, wherein said anti-LRP10 antibody or antigen binding fragment thereof, enhances recovery of all hematopoietic lineages, in a patient who has received chemotherapy and/or radiotherapy.

17. The method of claim 16, wherein said anti-LRP10 antibody or antigen binding fragment thereof, enhances recovery of lymphoid lineages.

* * * * *